United States Patent
Christensen et al.

(10) Patent No.: US 12,163,141 B2
(45) Date of Patent: Dec. 10, 2024

(54) NUCLEOTIDE SEQUENCES AND POLYPEPTIDES ENCODED THEREBY USEFUL FOR MODIFYING PLANT CHARACTERISTICS

(71) Applicant: CERES, INC., Thousand Oaks, CA (US)

(72) Inventors: Cory Christensen, Zionsville, IN (US); Nestor Apuya, Culver City, CA (US); Kenneth A. Feldmann, Tucson, AZ (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 18/499,906

(22) Filed: Nov. 1, 2023

(65) Prior Publication Data
US 2024/0167049 A1    May 23, 2024

Related U.S. Application Data

(60) Division of application No. 17/402,225, filed on Aug. 13, 2021, now Pat. No. 11,859,195, which is a division of application No. 16/793,520, filed on Feb. 18, 2020, now Pat. No. 11,136,590, which is a division of application No. 15/953,264, filed on Apr. 13, 2018, now Pat. No. 10,655,139, which is a continuation of application No. 14/565,186, filed on Dec. 9, 2014, now Pat. No. 9,957,521, which is a division of application No. 13/184,361, filed on Jul. 15, 2011, now Pat. No. 8,962,921, which is a division of application No. 11/140,450, filed on May 27, 2005, now Pat. No. 8,022,273.

(60) Provisional application No. 60/575,253, filed on May 27, 2004.

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01); *C12N 15/8242* (2013.01); *C12N 15/8261* (2013.01); *C12N 15/8271* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 8,022,273 B2 | 9/2011 | Christensen et al. | |
| 8,962,921 B2 | 2/2015 | Christensen et al. | |
| 9,957,521 B2 | 5/2018 | Christensen et al. | |
| 10,655,139 B2 | 5/2020 | Christensen et al. | |
| 11,136,590 B2 | 10/2021 | Christensen et al. | |
| 11,142,773 B2 | 10/2021 | Christensen et al. | |
| 11,708,582 B2 | 7/2023 | Christensen et al. | |
| 11,739,342 B2 | 8/2023 | Christensen et al. | |
| 11,859,195 B2 | 1/2024 | Christensen et al. | |
| 2006/0150283 A1* | 7/2006 | Alexandrov | C07K 14/415 536/23.6 |
| 2013/0042367 A1* | 2/2013 | Nadzan | C12N 15/8261 536/23.6 |
| 2020/0216854 A1 | 7/2020 | Christensen et al. | |
| 2021/0324399 A1 | 10/2021 | Christensen et al. | |
| 2022/0042032 A1 | 2/2022 | Christensen et al. | |

FOREIGN PATENT DOCUMENTS

| | | |
|---|---|---|
| EP | 1033405 A2 | 6/2000 |
| WO | 2002/016655 | 2/2002 |
| WO | 2003/081988 | 10/2003 |

OTHER PUBLICATIONS

Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495, 1994).*
Thornton et al. (Nature structural Biology, structural genomics supplement, Nov. 2000).*
Keskin et al. (Protein Science, 13:1043-1055, 2004).*
Kasuga et al. (Nature Biotechnology, vol. 17, pp. 287-291, Mar. 1999).
Thornton et al. (Nature structural Biology, structural genomics supplement, pp. 991-994; Nov. 2000).
Office Action Issued on Nov. 22, 2011 in Australian Application No. 2005250447.
Office Action Issued on Mar. 22, 2013 in Canadian Patent Application 2,568,367.
GenBank Accession No. AY084231, dated Jun. 13, 2002.
GenBank Accession No. AY084504, dated Jun. 13, 2002.
GenBank Accession No. AY084803, dated Jun. 13, 2002.
GenBank Accession No. AY085031, dated Jun. 13, 2002.
GenBank Accession No. AY085703, dated Jun. 13, 2002.
GenBank Accession No. AY086590, dated Jun. 13, 2002.
GenBank Accession No. NM_104688, dated Jan. 29, 2002.
GenBank Accession No. NM_106061, dated Jan. 29, 2002.
USPTO: Non-Final Office Action regarding U.S. Appl. No. 16/793,481, dated Mar. 25, 2021.
USPTO: Response to Non-Final Office Action regarding U.S. Appl. No. 16/793,481, filed Apr. 26, 2021.
USPTO: Supplemental Response to Non-Final Office Action regarding U.S. Appl. No. 16/793,481, filed May 3, 2021.
USPTO: Notice of Allowance regarding U.S. Appl. No. 16/793,481, dated Jun. 10, 2021.
Dai et al., The Rice YABBY1 Gene Is Involved in the Feedback Regulation of Gibberellin Metabolism, Plant Physiol. 144:121-133, 2007.

(Continued)

*Primary Examiner* — Vinod Kumar
(74) *Attorney, Agent, or Firm* — Dentons US LLP

(57) ABSTRACT

Isolated polynucleotides and polypeptides encoded thereby are described, together with the use of those products for making transgenic plants with increased tolerance to abiotic stress (e.g., high or low temperature, drought, flood).

8 Claims, 31 Drawing Sheets

Specification includes a Sequence Listing.

(56) References Cited

OTHER PUBLICATIONS

GenBank Accession No. AB011485, dated Feb. 14, 2004.
Sivamani et al., Improved biomass productivity and water use efficiency under water deficit conditions in transgenic wheat constitutively expressing the barley HVA1 gene, Plant Science 155:1-9, 2000.

* cited by examiner

```
Lead-clone11830      MSTFLIRILL  PLLLLAMTLP  RRSEAESE--  ------QWCIA  DEQTPDDELQ   43
CeresClone:1058242   MATFMLKLVL  PLLFLFMFPP  KTAYAEFE--  ------QWCVA  DEQTTESELQ   43
CeresClone:1602924   MTIVTTPHFL  TVLFFELLTS  CCTFCHAKAQ  APCCCTWCVA   KPAISDEDLQ   50
gi|29465664          MRCTAGVPDQ  PVPTPTPSVP  TSSSPVPKPP  TQCNKKWCVP   KAEATDADLQ   50

Consensus            M-TP------L P-LF-FM---P ---S-AE---  ---C---QWCVA -EQTTD-ELQ   50

Lead-clone11830      AALDWACGKG  GADCSKMQDE  NQPCFLPNTI  RDHASFAFNS   YYQTYKNKGG   93
CeresClone:1058242   AALDWACGKG  GADCSKIQV-  NQPCYLPNTL  KDHASYAFNS   YYQRFKHSGG   92
CeresClone:1602924   NNINYACTY-  -VDCRTIRP-  GSVCFEPQKL  VNRASWAMNL   YYQTNCRNYW   97
gi|29465664          SNIDYMCSDS  GMDCGPLQA-  NGACFNPNTV  RAHASYAMNS   WYQSKCRNDF   99

Consensus            A---D-AC-KG G-DCSKI Q--  NQPCFLPNTI  RDHASYA-NS  YYQT---NG-   100

Lead-clone11830      SCYFKCAAMI  TELDPSHGSC  QYEYNP      119
CeresClone:1058242   SCYFRCAAIE  LEVDPSHGSC  HYDFIP      118
CeresClone:1602924   NCDFKCSCIT  AVTDPSYGDC  KYSYKQ      123
gi|29465664          DCDFSCTCAL  TSSDPSNGSC  --SFLS      123

Consensus            SC-FKGA-I1  TE-DPSHGSC  -Y---P      126
```

FIG. 1

```
CeresClone:584111    ---MRSMTTR R------GYER CGKESATHAL CHEGFKRSTS CPSMGSNSSR   43
Leod-clone35743      MQMLRNLSTR TRSRRGGYER V-SDDSTFSL LGAKLRRSTS VPYYAPS---   46
gi|38603980          MQMLRNLSTR TRSRRGGYER V-SDDSTFSL LGAKLRRSTS VPYYAPS---   46
CeresClone:963524    MQMLRSFSTR TRSRRGGYER V-HDQSTFSL LGAKLRRSTS VPYYAPS---   46

Consensus            MQMLR-LSTR TRSRRGGYER V-SDDSTFSL LGAKLRRSTS VPYYAPS---   50

CeresClone:584111    KMALGSTYGE NMCKRNPTKK GNNN--SDKK SHPLLSFLAL ----RKKKTT   88
Leod-clone35743      -IRLG-GDFP VILEKLPROK PTKTVVTSKL SHPIFSLFDG YRRRSKKKAT   94
gi|38603980          -IRLG-GDFP VILEKLPROK PTKTVVTSKL SHPIFSLFDG YRRFNKKKAT   94
CeresClone:963524    -IKLGAQGVP TILEELPROK SKKVKPISKF SHPIFSFLMG ----KKKSIT   92

Consensus            -IRLG-GDFP VILEKLPROK PTKTVVTSKL SHPIFS---DG YRRR-KKK-T  100

CeresClone:584111    ARPEFARYLE YLKEGGMWDF NSNKPVMYYE    118
Leod-clone35743      AKPEFSRYHE YLKESGMWDL RSNSPVIYFK    124
gi|38603980          AKPEFSRYHE YLKESGMWDL RSNSPVIYFK    124
CeresClone:963524    RKPEFSRYLE YLKEGGMWDA RINTPV----    118

Consensus            AKPEFSRY-E YLKE-GMWDL RSNSPVIYFK    130
```

FIG. 2

| | | | | | | |
|---|---|---|---|---|---|---|
| gi\|15866583 | | MCGDGCAEQP | VI HFVF VHGA | SHGAWCWYKL | TSLLETACFR | TSVDLTGAG | 50 |
| gi\|2780225 | | ---------MA | VVDFVL HTT | CHGAW WYKL | KPVLEA GHK | VTALDLAASG | 42 |
| gi\|50513520 | | ---------MA | FAHFVLI HTI | CHGAW WHKL | KPLLEAL GHK | VTALDLAASG | 42 |
| gi\|6435646 | | ---------MA | FAHFVLI HTI | CHGAW MHKL | KPLLEAL GHK | VTALDLAASG | 42 |
| gi\|57899620 | | ----MEGSSSS | SKHFI LVHGL | CHGAWCWYKV | VTMLRSEGHR | VTALDLAASG | 47 |
| CeresClone:93606B | | -----MEGSSS | GKHFI LI HGL | CHGAWCWYKL | VPMLRAAGHR | VTALDMAASG | 46 |
| gi\|34907176 | | ----MEI SSSS | KKHFI LVHGL | CHGAWCWYRV | VAAL RAAGHR | ATALDMAASG | 47 |
| gi\|56393011 | | -MEKSMSPFV | KKHFVLVHTA | FHGAWCWYKI | VAEMRSSGHN | VTALDLKASG | 49 |
| gi\|41814856 | | -------MEKGD | KNHFVLVHGA | CHGAWCWYKV | VTI LRSEGHK | VSVLDMAASG | 45 |
| gi\|56392765 | | ------MEKGN | KNHFVLVHGA | CHGAWCWYKV | VTL LRSEGHK | VSVLDMAASG | 45 |
| CeresClone:644331 | | -MEACAGDAS | SAHFVLVHGI | CLGCWSWFKV | ATRLRGAGHR | VSTPDLAASG | 49 |
| gi\|53830670 | | --------MEV | MKHFVTVHGV | GHGAWVTYKL | KPSI EAAGHR | CTAVNLAASG | 43 |
| Lead-clone26006 | | -----MSEEKR | KQHFVLVHGA | CHGAWCWYKV | KPLLEAL GHR | VTALDLAASG | 46 |
| CeresClone:1010900 | | -----MSEEKR | KQHFVLVHGS | CHGAWCWYKV | KPLLEAVGHR | VTAVDLAASG | 46 |
| gi\|20195998 | | -----MSEEKR | KQHFVLVHGS | CHGAWCWYKV | KPLLEAVGHR | VTAVDLAASG | 46 |
| gi\|27754457 | | -----MSEEKR | KQHFVLVHGS | CHGAWCWYKV | KPLLEAVGHR | VTAVDLAASG | 46 |
| gi\|6651393 | | -MHSAANAKQ | DKHFVLVHGG | CLGAWI MYKL | KPLLESAGHK | VTAVDLSAAG | 49 |
| gi\|14279437 | | --MEEVYGME | EKHFVLVHGV | NHGAWCWYKL | KARLVAGGHR | VTAVDLAASG | 48 |
| gi\|40549303 | | --------MKE | GKHFVLVHGA | CHGCWSWYKL | KPLLEAAGHK | VTALDLAASG | 43 |
| | | | | | | | |
| Consensus | | ---------- | KKHFVLVHGA | CHGAWCWYK- | KPLLEA-GHR | VTALDLAASG | 50 |

FIG. 3

```
gi|15866583      S-VTDSNTV LESDQYNRPL FSLLSDLPP- SHKVILVGHS ISGQSVLDAL  98
gi|2780225       VD-PRQIEQI NSFDEYSEPL LTFMESLPQ- GEKVILVGES CGGLNIAIAA  90
gi|50513520      VD-PRQIEEI GSFDEYSEPL LTFLEALPP- GEKVILVGES CGGLNIAIAA  90
gi|6435645       VD-PRQIEEI GSFDEYSEPL LTFLEALPP- GEKVILVGES CGGLNIAIAA  90
gi|57899620      VH-PARVDEV HSFEEYSQPL LDAVAEAPAI- GERLILVGHS FGGLSIALAM  95
CeresClone:936068 AH-PARMDEV PSFEDYSWPL LDAVAAAPAI- GERLVLVGHS LGGLNIALAM  94
gi|34907176      AH-PARVDEV GIFEEYSRPL LDAVAAAAAP GERLVLVGHS HGGLSVALAM  96
gi|56393011      IN-PKQALQI PNESDYLSPL MEFMASLPAI- NEKIILVGHA LGCLAISKAM  97
gi|41814856      IN-PKHVDDL NSMADYNEPL MEFMNSLPQ- LERVVLVGHS MGGINISLAM  93
gi|56392765      IN-PKHVEDL NSMADYNEPL MEFMNSLPQ- QERVVLVGHS MGGINISLAM  93
CeresClone:644331 VD-PRPLREV PIFRDYTKPL LDLLESLPS- GEKVVLVGHS LGGVNVALAC  97
gi|53830670      IN-EKKLEEV RSSIDYAAPL LEVLDSVPE- NEKVILVGHS GGGMIAAVGM  91
Lead-clone26006  IDTTRSITDI SICEQYSEPL MQLMTSLPN- DEKVVLVGHS FGGLSLALAM  95
CeresClone:1010900 IDTTPSITDI PICEQYSEPL TKLLTSLPN- DEKVVLVGHS FGGLNLAIAM  95
gi|20196998      IDTTRSITDI PICEQYSEPL TKLLTSLPN- DEKVVLVGHS FSGLNLAIAM  85
gi|27754457      IDTIRSITDI PICEQYSEPL TKLLTSLPN- DEKVVLVGHS FCGLNLAIAM  95
gi|6651393       N-PRRLDEI HIFRDYSEPL MEVMASIPP- DEKVVLLGHS FGGMSLGLAM  97
gi|14279437      N-MKRIEDV HIFHAYSEPL MEVLASLPAI- EEKVILVGHS LGGVILALAC  96
gi|40549303      TD-LRKIEEL RILYDYTLPL MELMESLSAI- DEKVILVGHS LGGMNLGLAM  91

Consensus        I ---PRQI-EI --FE-YSEPL MELM-SLP--- -EKVVLVGHS -GGLNIALAM  100
```

FIG. 3, continued

|  |  |  |  |  |  |  |
|---|---|---|---|---|---|---|
| gi\|15866583 | QRFLDKISMA | YLAASMVKP | GSVPSPHMSD | MHADAREEN- | M----CYIYG | 144 |
| gi\|2780225 | DKYPEKIAAA | VFQNSLLPDT | KHKPSYVVDK | LMEVFPD---- | -WKDTEYFEF | 136 |
| gi\|50513520 | DKYCEKIAAA | VFHNSVLPDT | EHCPSYVVDK | LMEVFPD---- | -WKDTIYFTN | 136 |
| gi\|6435645 | DKYCEKIAAA | VFHNSVLPDT | EHCPSYVVDK | LMEVFPD---- | -WKDTIYFTY | 136 |
| gi\|57899620 | ERFPEKIAVA | VFVAAAVPCV | GKR---TLPEL | IREKAPKDM- | -LLDSKMIPI | 141 |
| CeresClone:936068 | ERFPDKVAAA | VFLAACMPCV | GRHMGATTEE | IMRRIKPDF- | -FMDMKRMVL | 142 |
| gi\|34907176 | ERFPDKVAAA | VFVAAAMPCV | CKHMGVPTEE | FMRRTAPEG- | LLMDCEMVAI | 145 |
| gi\|56393011 | ETFPEKISVA | VFLSGLMPGP | NIDATINCTK | AGSAVLG---- | -QLDNCVTYE | 143 |
| gi\|41814855 | EKFPQKIVVA | VFVTAFMPGP | DLNLVALGDQ | FNDQVES---- | -HMDTEFVYN | 139 |
| gi\|56392765 | EKFPRKIAVA | VFVSASMPCP | DLNLVAMIDQ | YSQDVET---- | -PMDTEFVYN | 139 |
| CeresClone:644331 | ECFPEKIARA | VFVAAFMPDH | RSPPSYVLEK | FVEGRTLD-- | -WMDTEFKPQ | 144 |
| gi\|53830670 | EKFPNKISLA | VFLNAIMPDT | ENRPSYVLEE | MTAKTPPEA- | -WKDCQFSAM | 139 |
| Lead-clone26006 | DKFPDKISVS | VFVTAFMPDT | KHSPSFVEEK | FASSMTPIG- | -HMGSELETY | 143 |
| CeresClone:1010900 | EKFPEKISVA | VFLTAFMPDT | EHSPSFVLDK | FCSNMPQEA- | -WMGTEFEPY | 143 |
| gi\|20196998 | EKFPEKISVA | VFLTAFMPDT | EHSPSFVLDK | FCSNMPQEA- | -WMGTEFEPY | 143 |
| gi\|27754457 | EKFPKKISVA | VFLTAFMPDT | EHSPSFVLDK | FGSNMPQEA- | -WMGTEFEPY | 143 |
| gi\|6651393 | ETYPEKISVA | VFMSAMMPDF | NHSLTYPEEK | YNEKCPADM- | -MDSQFSIM | 145 |
| gi\|14279437 | DKFPEKISVA | VFVTAFMPDT | THRPSFVLEQ | YSEKMGKEDD | SWLDTQFSQC | 146 |
| gi\|40549303 | EKYPDKIYAA | VFLAAFMPDS | VHNSSFVLEQ | YNERTEAEN- | -WLDTQFLPY | 139 |
| Consensus | EKFPEKISVA | VFL-A-MPDT | EH-PS-VLEK | ------P-E--- | -WMDTEF---Y | 150 |

| | | | | | | |
|---|---|---|---|---|---|---|
| gi\|15866583 | KSPP---NPE | VEKPRVYIK | TGKDNLFSSV | -RDDLLVKNW | PPSDFYVLEE | 239 |
| gi\|2780225 | QREK-FTEKG | YGSIKKIYVW | TGDDKFLPE | -FQLWQIENY | KPDLVRVMG | 233 |
| gi\|50513520 | KRPF-FTKEG | YGSIKKIYVW | TQQDEFLPE | -FQLWQIENY | KPDKVYKVEG | 232 |
| gi\|6436646 | KRPF-FTKEG | YGSIKKIYVW | TQQDEFLPE | -FQLWQIENY | KPDKVYKVEG | 232 |
| gi\|57899620 | KDDRLLISAN | YGSVKRVQLM | AMEDDL--KE | -VHRYMITLS | PGVEVEEIAG | 237 |
| CeresClone:936068 | KDEALLTEAK | YGSVKKVYVV | AMADASNSEE | -MDRWMVDMS | PGTEAEEIAG | 240 |
| gi\|34907176 | KDESLLTNGN | YGSVKKVYVI | AKADSSSTEE | -MDRWMVAMS | PGTDVEEIAG | 243 |
| gi\|56393011 | KEVV-LGSKR | YGSVKRVFIV | ATENDALKKE | -FLKEMIEKN | PPDEVKEIEG | 240 |
| gi\|41814856 | ANTT-LSKEK | YGSVFRVYVV | CDKDNVLKEQ | QFQKWLINNN | PPDEVQIHN | 237 |
| gi\|56392765 | TNTT-LSKEK | YGSVFRVYVV | CDKDKVLKEE | QFQRWLIKNN | PPNEVDMHD | 237 |
| CeresClone:644331 | LQPP-HTEAR | YGSVRKAYVV | FKDDHAIVEQ | -FQRWMVENY | PVDEVMEIDQ | 240 |
| gi\|53830670 | KAEK-FTEEG | FGSVPRVYVI | AAEDKIPPE | -FQRWMIENN | PVKEVKEIKG | 233 |
| Lead-clone26006 | KMEN-FSEKG | YGSVPRAYIV | CKEDNISED | -RDRWMIBNY | PANLVEMEE | 238 |
| CeresClone:1010900 | KMKN-FSDEG | YGSVPRVFIV | CKEDKAIPEE | -RDRWMIDNF | PVNLVMEMEE | 238 |
| gi\|20196998 | KMKN-FSDEG | YGSVPRVFIV | CKEDKAIPEE | -RDRWMIDNF | PVNLVMEMEE | 238 |
| gi\|27754457 | KMKN-FSDEG | YGSVPRVFIV | CKEDKAIPEE | -RDRWMIDNF | PVNLVMEMEE | 238 |
| gi\|6651393 | KAKK-FSDER | YGSVKRAYIF | CNEDKSFPVE | -FQKWFVESV | GADKVKEIKE | 241 |
| gi\|14279437 | KESK-FSDEG | YGSVKRVYLV | CEEDFGDPKQ | -FQRWMIQNYI | PVNEVMEIKG | 242 |
| gi\|40549303 | KAKY-FTDER | FGSVKRVYIV | CTEDKCIPEE | -FQRWQLDN | GVTEAIEIKG | 235 |
| Consensus | K-----F---E-- | YGSVKRVYIV | ---ED---I-EE | -FQRWMIENY | P---EV-EIEG | 250 |

FIG. 3, continued

| | | | | |
|---|---|---|---|---|
| gi\|15866583 | SDHSAFFSVP | TTLFVYLLRA | VSFLHK | 265 |
| gi\|2780225 | GDHKLQLTKT | NEIAGILDKV | ADIYA- | 258 |
| gi\|50513520 | GDHLLQLTKT | KEIAEILDEV | ADTYN- | 257 |
| gi\|6435646 | GDHKLQLTKT | KEIAEILDEV | ADTYN- | 257 |
| gi\|57899620 | ADHAVMCSRP | RELSDLLAKI | GSKYD- | 262 |
| CeresClone:936068 | ADHMAMCSKP | RELCDVLLRI | ADKYE- | 265 |
| gi\|34907176 | ADHAVMNSKP | RELCDLLIKI | ANKYE- | 268 |
| gi\|56393011 | SDHVTMMSKP | QQLFTTLLSI | ANKYK- | 265 |
| gi\|41814856 | ADHMVMFSKP | RDLSSCLVMI | SDKYY- | 262 |
| gi\|56392765 | ACHMVMFSKP | RELCSCLVMI | SQKYH- | 262 |
| CeresClone:644331 | ADHMALLSDP | TELARCLADI | AMKYAA | 266 |
| gi\|53830670 | ADHMPMFSKP | DELSQCLLDI | AKKHA- | 258 |
| Lead-clone26006 | TDHMPMFCKP | QVLSDHLLAI | ADNFS- | 263 |
| CeresClone:1010900 | TDHMPMFCKP | QQLSDYFLKI | ADKFV- | 263 |
| gi\|20196998 | TDHMPMFCKP | QQLSDYFLKI | ADKFV- | 263 |
| gi\|27754457 | TDHMPMFCKP | QQLSDYFLKI | ADKFV- | 263 |
| gi\|6651393 | ADHMGMLSQP | REVCKCLLDI | SDS--- | 264 |
| gi\|14279437 | GDHMAMLSDP | DKLCDCLSQI | SLKYA- | 267 |
| gi\|40549303 | ADHMAMLCEP | DKLCASLLEI | AHKYN- | 260 |
| Consensus | -DHM-M-SKP | QELS--LL-I | A-KY-- | 276 |

| | | | | | | |
|---|---|---|---|---|---|---|
| gi\|3329471 | RGKMTALLDG | DNVRHGLNSN | LTFIAEDRIE | HPPFPRSEQA | LCRRMRPPLR | 140 |
| CeresClone:300011 | RGELTYVLDG | DNLRHGLNRD | LSFIAEDRAE | ---NIRRVGE | VAKLFADAGL | 171 |
| gi\|50938537 | RGKLSYVLDG | DNLRHGLNKD | LSFKAEDRAE | ---NIRRVGE | VAKLFADAGL | 241 |
| gi\|2832300 | KGKLTYILDG | DNVRHGLNSD | LSFKAEDRAE | ---NIRRIGE | VAKLFADAGV | 208 |
| Lead-clone125039 | RGKLSYILDG | DNVRHGLNSD | LSFEADDRAE | ---NIRRVGE | VAKLFADSGI | 183 |
| gi\|9757873 | RGKLSYILDG | DNVRHGLNSD | LSFEADDRAE | ---NIRRVGE | VAKLFADSGI | 177 |
| Consensus | RGKL-YILDG | DNVRHGLNSD | LSF-AEDRAE | ---NIRRVGE | VAKLFADAG- | 250 |

| | | | | | | |
|---|---|---|---|---|---|---|
| gi\|3329471 | ELHLRPIAPL | RPVPERCL--- | ---AGDFVECR | MKIPIELCTQ | RDPKGLYKKA | 186 |
| CeresClone:300011 | VCIASLISPY | RSDREACRDE | LPKHSFIEVF | LDVPLQVCEA | RDPKGLYKLA | 221 |
| gi\|50938537 | VCIASDISPY | RPDRESCRAL | LEDGSFIEVF | LNMPLELCES | RDPKGLYKLA | 291 |
| gi\|2832300 | ICIASLISPY | RKPPDACRSL | LPEGDFIEVF | MDVPLKVCEA | RDPKGLYKLA | 258 |
| Lead-clone125039 | ICIASLISPY | RIERAACRAL | LPQGDFIEVF | MDVPLHVCEA | RDPKGLYKPA | 232 |
| gi\|9757873 | ICIASLISPY | RIERAACRAL | LPQGDFIEVF | MDVPLHVCEA | RDPKGLYKPA | 227 |
| Consensus | VCIASLISPY | R---R-ACRAL | LP-GDFIEVF | MDVPLEVCEA | RDPKGLYK-A | 300 |

| | | | | | | |
|---|---|---|---|---|---|---|
| gi\|3329471 | RAGLMKGFTG | IDDPYELPLE | PELLIVREE | GSDMNSP--- | ----------- | 222 |
| CeresClone:300011 | RAGKIKGFTG | IDDPYELPSD | CEIVIDCKI--- | VGDCPSP--- | ----------- | 256 |
| gi\|50938537 | RAGKIKGFTG | IDDPYESPLN | SEIDKEV--- | DGVCPSP--- | ----------- | 328 |
| gi\|2832300 | RAGKIKGFTG | IDDPYEPPLR | SEIVLRQR--- | LGMCDSP--- | ----------- | 293 |
| Lead-clone125039 | RAGKIKGFTG | VDDPYEAPLD | CEIVIQNSRG | KGLSSSSSSS | SSPSSSSSSSL | 282 |
| gi\|9757873 | RAGKIKGFTG | VDDPYEAPLD | CEVRISN--- | FSSSSSL--- | ----------- | 262 |
| Consensus | RAGKIKGFTG | IDDPYEAPLD | CEIVIQ-K--- | -G-C-SP--- | ----------- | 350 |

| | | | | | | |
|---|---|---|---|---|---|---|
| gi\|3329471 | EAMAKQFDM | LEAKGFLKGP | AVASSGGSCA | RVARWGGHGR | RRGRQRLAW | 271 |
| CeresClone:300011 | ESMACHVVSY | LEDNCFLQD- | ----------- | ----------- | ----------- | 275 |
| gi\|50938537 | SDMAGQVVTY | LEEKGFLHD- | ----------- | ----------- | ----------- | 345 |
| gi\|2832300 | CDLADIVISY | LEENGYLKA- | ----------- | ----------- | ----------- | 312 |
| Lead-clone125039 | CEMADIVVSY | LDQNGYLKKH | SITKSRDCM-- | ----------- | ----------- | 310 |
| gi\|9757873 | CEMADIVVSY | LDQNGYLKKH | SITKSRNCM-- | ----------- | ----------- | 290 |
| Consensus | C-MADIVVSY | LE-NG-LK-- | S---S------ | ----------- | ----------- | 399 |

FIG. 6, continued

```
CeresClone:584111    MFRSMTTRR- --GYERLGKE SAITALLHEG FKRGTSLPSW GSNSBRKMAL  47
CeresClone:1068483   MFRAMSTRKV HGGYEKLVEQ EPK------- LKRVTSVPAS VYGNSRNPV-  42
Lead-clone10044      MFRAMSTRKV HGGYEKLGDE EAR------- LKRVSSVPAS VYGHSRNPV-  42
gi|4835241           MFRAMSTRKI HGGYEKLGDE EAR------- LKRVSSVPAS VYGHSRNPV-  42

Consensus            MFRAMSTRKV HGGYEKLGDE EAR------- LKRV-SVPAS VYGHSRNPV- 50

CeresClone:584111    GSTYCELNLK RNPTMRGNNN SDKKSHPLLS FLAL---RPK KKT------- 87
CeresClone:1068483   -----QEVK KTPTVKPTGG S---VHPLLS FFDVRFQKKK KKT--KKSLA 82
Lead-clone10044      -----QEVK KTPTAKPTGG S---VHPLFS FFDVHFQRKK KKT-RKKSLA 83
gi|4835241           -----QEVK KTPTAKPTGG S---VHPLFS FFDVHFQRKK KKTAKKKSLA 83

Consensus            -----QEVK KTPTAKPTGG S---YHPL-S FFDVHFQRKK KKT--KKKSLA 100

CeresClone:584111    TARPEFARYL EYLKEGGMWD FNSNKPVMYY E  118
CeresClone:1068483   TAKPEFARYM AYVKEGGVWD PNSNAPVIHY R  113
Lead-clone10044      TAKPEFARYM EYVREGGVWD PSSNAPVIHY R  114
gi|4835241           TAKPEFARYM EYVREGGVWD PSSNAPVIHY R  114

Consensus            TAKPEFARYM EYV-EGGVWD P-SNAPVIHY R  131
```

FIG. 7

```
CeresClone:621848      ----------  ----MKLSTL  FLFLEHSAHA  ALSDEAT---  ---F--IRDG  28
gi|50899872            MRKGAAGMAC  TCSAAAAASA  LVKLLVLVAA  VAATTSAGGG  DEPTYETKSI  50
CeresClone:316544      ---------M  AAAATRSLHS  FLALLLLLAA  AAAAAAL---  ----SYETKSI  35
Lead-clone17206        ----------  -------MASPV  FVISLLLLSF  SSAVFSD---  ----------  22
CeresClone:124660      ----------  -MTSFCSMIS  QLLLLLLSL   SSAVSD---   ----------  26
gi|17104523            ----------  ----MTSFCS  MSLLLLLSL   SSAVFSD---  ----------  23
gi|1754985             ----------  ----MTSFCS  MSLLLLLSL   SSFVFSD---  ----------  23
gi|13928598            ----------  MHSSEAMVVS  LLCALFL-S   SLSLVSS---  ----------  25
gi|62903513            ----------  --MA KLSDSQTMAL  FTVFLLFLSS  SLALS-----  ----------  27
gi|18220               -----MANF   SESKSMMAVF  FMFFLLLLSS  SSSSSSS---  ----------  31
gi|18222               ----------  -----MMAVF  FMFFLLLLSS  SSSSSSS---  ----------  22

Consensus              ----------  ----S---S--S FL-LLLLLSA  SSAV-S----  ----------  50

CeresClone:621848      LKSYSQLDLP  HSVFCSESVA  FDCHSKGPIV  CVSDGRILKW  HETKREWIDF  78
gi|50899872            DPSLAVMLP   APVTGPESLA  FDGRGDGPYT  CCSDGRILRW  RCGRLGWIEF  100
CeresClone:316544      DPGLVVMLP   EEVSGPESLA  FDGRSKGPYS  GVSDGRVLRW  QGPLRGWIEF  85
Lead-clone17206        DASFQKLPVP  DKRSGPESFA  FDSTCL-FYT  GVSGCKILKY  V--PGKGYVDF  70
CeresClone:124660      DASFQKLPVP  ETRSGPEAFA  FDSTGKGFYT  GVSGGKILKY  L--PETGYVDF  75
gi|17104523            DASFQKLPVP  ETRSGPEAFA  FDSTGKGFYT  GVSGGKILKY  L--PETGYVDF  72
gi|1754985             DASFQKLPVP  ETRSGPEAFA  FDSTGKGFYT  GVSGGKILKY  L--PETGYVDF  72
gi|13928598            SPEEFEL-FLE APSYGPNAYA  FDSDGFELYA  SVFDGRIIKY  DKPSNKFLER  73
gi|62903513            SPILKETLE   APSYAPNSFT  FDSTNKGFYT  SVQDGRVIKY  EGPNSGFVDF  77
gi|18220               SPILKKIFIE  SPSYAPNAFT  FDSTDKGFYT  SVQDGRVIKY  EGPNSGFTDF  81
gi|18222               SPILKKLFLE  SPSYAPNAFT  FDSTDKGFYT  SVQDGRVIKY  EGPNSGFTDF  72

Consensus              DPSFQKL--P  --P-SGPEAFA FDSTGKGFYT  GVSDGRILKY  ---P---G--VDF 100
```

| | | | | | | | |
|---|---|---|---|---|---|---|---|
| CeresClone:621848 | YYISITLSGD | RTGRLLKYVE | STQSVHVLVK | GLAFPNGVAL | SKDNSFTTVA | 226 |
| gi|50899872 | DYLLVVAMGD | ETGRLLRYDA | RRRRVTVLHS | GLPYPNGVAV | SDDGTHVVVA | 248 |
| CeresClone:316544 | DYLLVVAMGD | ETGRLLRYER | RFGRVGVLDA | GLSYPNGVAV | SADGTHVVVA | 233 |
| Lead-clone 17206 | EVLIAMGLKD | ASGKLFKYDP | ATKAVTELME | GLSGAAGCAV | SSDGSFVLVS | 217 |
| CeresClone:124660 | QVLIALGLKD | ATGKLMKYDP | STKVVTVLME | GLSGSAGCAV | SSDGSFVLVS | 222 |
| gi|17104523 | QVLIALGLKD | ATGKLYKYDP | STKVVTVLME | GLSGSAGCAV | SSDGSFVLVS | 219 |
| gi|1754985 | QVLIALGLKD | ATGKLLKYDP | STKVVTVLME | GLSGSAGCAV | SSDGSFVLVS | 218 |
| gi|13928598 | QVGDTIRLND | TTGRLIKYDP | STEEVTVLMK | GLNPGGTEV | SKUGSFVLVG | 220 |
| gi|62903513 | GVDQIMDTSD | KTGRLIKYDP | STKETTLLLK | ELFVPGGAEV | SADGSFVLVA | 224 |
| gi|18220 | GVEEIMNTSD | RTGRLMKYDP | STKETTLLLK | ELHVPGGAEI | SADGSFVVVA | 230 |
| gi|18222 | GVEELMNTSD | RTGRLMKYDP | STKETTLLLK | ELHVPGGAEI | SADGSFVVVA | 221 |
| Consensus | -VLIV--L-D | -TGRLLKYDP | STK-VTVLMK | GL---P-G-AV | S-DGSFVLVA | 250 |

| | | | | | | | |
|---|---|---|---|---|---|---|---|
| CeresClone:621848 | ESTTFKTLRI | QVRDSKTNNN | NIEFFAQVPR | SPDNIKR-NA | KCEFWVALNS | 274 |
| gi|50899872 | HTGLCELRRY | WLRGPRAGHS | ---ETFAEVPG | YPDNVRR-DC | DGGYWVALSR | 295 |
| CeresClone:316544 | HTALCELRRY | WIRGARAGTS | ---DTFAELPG | YPDNLRA-DC | RGGYWVALSS | 280 |
| Lead-clone 17206 | EFIKSNKKY | WIKGPKAGTE | --EDFSSLVS | NPDNIRRVGS | TGNFWVAS-- | 263 |
| CeresClone:124660 | QFTKSNKRY | WIKGPKAGSS | --EDFTNSVS | NPDNIKRICS | TGNFWVAS-- | 268 |
| gi|17104523 | QFTKSNKRY | WIKGPKAGSS | --EDFTNSVS | NPDNIKRGS | TGNFWVAS-- | 265 |
| gi|1754985 | QFTKSNKRY | WIKGPKAGSS | --EDFTNSVS | NPDNIKRGS | TGNFWVAS-- | 265 |
| gi|13928598 | EFASHRILKY | WLKGPKANTS | --E-FLKVR | GPDNIKR-TK | DCDFWVAS-- | 264 |
| gi|62903513 | EFLSHQIVKY | WLEGPKKGTA | --E-VLVKIP | NPGNIKR-NA | DGHFWVSSSE | 270 |
| gi|18220 | EFLSNRIVKY | WLEGPKKGSA | --E-FLVTIP | NPGNIKR-NS | DGHFWVSSSE | 276 |
| gi|18222 | EFLSNRIVKY | WLEGPKKGSA | --E-FLVTIP | NPGNIKR-NS | DGHFWVSSSE | 267 |
| Consensus | EF----I KKY | W-KGPKAGSS | --E-F----V- | NPDNIKR-NS | -GNFWVASS- | 300 |

```
gi|13928598        NASFKEFSSF    351
gi|62903513        ----------    344
gi|21097           ----------    342
gi|18222           ----------    347
gi|18220           ----------    352
gi|30698979        ----------    328
gi|12325143        ----------    329
Lead-clone104691   ----------    335
CeresClone:17206   ----------    325
gi|30984544        ----------    325
CeresClone:621848  ----------    347
CeresClone:316544  ----------    343
gi|50899872        ----------    364

Consensus          ----------    410
```

FIG. 9, continued

NUCLEOTIDE SEQUENCES AND POLYPEPTIDES ENCODED THEREBY USEFUL FOR MODIFYING PLANT CHARACTERISTICS

This application is a divisional of U.S. patent application Ser. No. 17/402,225, filed Aug. 13, 2021, which is a divisional of U.S. patent application Ser. No. 16/793,520, filed on Feb. 18, 2020, now U.S. Pat. No. 11,136,590, which is a divisional of U.S. patent application Ser. No. 15/953,264, filed on Apr. 13, 2018, now U.S. Pat. No. 10,655,139, which is a continuation of U.S. patent application Ser. No. 14/565,186, filed on Dec. 9, 2014, now U.S. Pat. No. 9,957,521, which is a divisional of U.S. patent application Ser. No. 13/184,361, filed on Jul. 15, 2011, now U.S. Pat. No. 8,962,921, which is a divisional of U.S. patent application Ser. No. 11/140,450, filed on May 27, 2005, now U.S. Pat. No. 8,022,273, which claims priority under 35 U.S.C. § 119(e) of U.S. Provisional Application No. 60/575,253, filed on May 27, 2004. The entirety of each of the above-mentioned patent applications is hereby incorporated by reference.

INCORPORATION OF SEQUENCE LISTING

The sequence listing that is contained in the XML file named "CRES008USC1D6_ST26," which is 371 kilobytes as measured in Microsoft Windows operating system and was created on Sep. 27, 2023, is filed electronically herewith and incorporated herein by reference.

FIELD OF THE INVENTION

The present invention relates to isolated polynucleotides, polypeptides encoded thereby, and the use of those sequences for making transgenic plants with modulated water use efficiency.

BACKGROUND OF THE INVENTION

Plants are constantly exposed to a variety of biotic (e.g., pathogen infection and insect herbivory) and abiotic (e.g., high or low temperature, drought, flood, anaerobic conditions and salinity) stresses. To survive these challenges, plants have developed elaborate mechanisms to perceive external signals and to manifest adaptive responses with proper physiological and morphological changes (Bohnert et al., 1995). Plants exposed to heat and/or low water or drought conditions typically have low yields of plant material, seeds, fruit and other edible products. Some countries of the world consistently have very low rainfall and therefore have problems growing sufficient food crops for their population. Yet it has been observed that some plants survive and thrive in low water environments. It would, therefore, be of great interest and importance to be able to identify genes that confer improved water efficiency characteristics to thereby enable one to create transformed plants (such as crop plants) with modulated water efficiency characteristics to, thereby, better survive high and/or low heat, high and/or low water, and drought or flood conditions. Exogenous application to plants of high concentrations of PEG and mannitol are known to produce osmotic stress resulting in the retardation of growth and vigor and are used to assess drought responses. Exogenous application of ABA stimulates drought-responses in plants and can, therefore, be an important screen to identify genes that confer improved water efficiency.

In the field of agriculture and forestry efforts are constantly being made to produce plants with an increased growth potential in order to feed the ever-increasing world population and to guarantee the supply of reproducible raw materials. This is done conventionally through plant breeding. The breeding process is, however, both time-consuming and labor-intensive. Furthermore, appropriate breeding programs must be performed for each relevant plant species.

Progress has been made in part by the genetic manipulation of plants; that is by introducing and expressing recombinant nucleic acid molecules in plants. Such approaches have the advantage of not usually being limited to one plant species, but instead being transferable among plant species. (Zhang et al. (2004) *Plant Physiol.* 135:615). There is a need for generally applicable processes that improve forest or agricultural plant growth potential. Therefore, the present invention relates to a process for increasing the abiotic stress tolerance and consequently the growth potential in plants, characterized by expression of recombinant DNA molecules stably integrated into the plant genome.

SUMMARY OF THE INVENTION

The present invention, therefore, relates to isolated polynucleotides, polypeptides encoded thereby, and the use of those sequences for making transgenic plants with modulated water use efficiency.

The present invention also relates to processes for increasing the growth potential in plants under abnormal water conditions, recombinant nucleic acid molecules and polypeptides used for these processes and their uses, as well as to plants themselves.

Unless otherwise defined, all technical and scientific terms used herein have the same meaning as commonly understood by one of ordinary skill in the art to which this invention belongs.

BRIEF DESCRIPTION OF THE DRAWINGS

FIG. 1 provides the results of a consensus sequence (SEQ ID NOs: 112-120) analysis based on Ceres cDNA 12331850.

FIG. 2 provides the results of a consensus sequence (SEQ ID NOs: 121-129) analysis based on Ceres cDNA 12334963.

FIG. 3 provides the results of a consensus sequence (SEQ ID NOs: 130-146) analysis based on Ceres cDNA 12333678.

FIG. 4 provides the results of a consensus sequence (SEQ ID NOs: 147-177) analysis based on Ceres cDNA 12659859.

FIG. 5 provides the results of a consensus sequence (SEQ ID NOs: 178-200) analysis based on Ceres cDNA 12723147.

FIG. 6 provides the results of a consensus sequence (SEQ ID NOs: 201-214) analysis based on Ceres cDNA 13488750.

FIG. 7 provides the results of a consensus sequence (SEQ ID NOs: 215-222) analysis based on Ceres cDNA 13489782.

FIG. 8 provides the results of a consensus sequence (SEQ ID NOs: 223-240) analysis based on Ceres cDNA 13500101.

FIG. 9 provides the results of a consensus sequence (SEQ ID NOs: 241-262) analysis based on Ceres cDNA 13509011 (12357529).

DETAILED DESCRIPTION OF THE INVENTION

1. Definitions

The following terms are utilized throughout this application:

Constitutive Promoter: Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region and the 1' or 2' promoter derived from T-DNA of *Agrobacterium tumefaciens*, and other transcription initiation regions from various plant genes, such as the maize ubiquitin-1 promoter, known to those of skill.

Domain: Domains are fingerprints or signatures that can be used to characterize protein families and/or parts of proteins. Such fingerprints or signatures can comprise conserved (1) primary sequence, (2) secondary structure, and/or (3) three-dimensional conformation. Generally, each domain has been associated with either a family of proteins or motifs. Typically, these families and/or motifs have been correlated with specific in-vitro and/or in-vivo activities. A domain can be any length, including the entirety of the sequence of a protein. Detailed descriptions of the domains, associated families and motifs, and correlated activities of the polypeptides of the instant invention are described below. Usually, the polypeptides with designated domain(s) can exhibit at least one activity that is exhibited by any polypeptide that comprises the same domain(s).

Drought: Plant species vary in their capacity to tolerate drought conditions. For each species, optimal growth can be achieved if a certain level of water is always available. Other factors such as temperature and soil conditions have a significant impact on the availability of water to the plant. "Drought" can be defined as the set of environmental conditions under which a plant will begin to suffer the effects of water deprivation, such as decreased photosynthesis, loss of turgor (wilting) and decreased stomatal conductance. This drought condition results in a significant reduction in yield. Water deprivation may be caused by lack of rainfall or limited irrigation. Alternatively, water deficit may also be caused by high temperatures, low humidity, saline soils, freezing temperatures or water-logged soils that damage roots and limit water uptake to the shoot. Since plant species vary in their capacity to tolerate water deficit, the precise environmental conditions that cause drought stress can not be generalized. However, drought tolerant plants produce higher biomass and yield than plants that are not drought tolerant. Differences in physical appearance, recovery and yield can be quantified and statistically analyzed using well known measurement and analysis methods.

Endogenous: The term "endogenous," within the context of the current invention refers to any polynucleotide, polypeptide or protein sequence which is a natural part of a cell or organisms regenerated from said cell.

Exogenous: "Exogenous," as referred to within, is any polynucleotide, polypeptide or protein sequence, whether chimeric or not, that is initially or subsequently introduced into the genome of an individual host cell or the organism regenerated from said host cell by any means other than by a sexual cross. Examples of means by which this can be accomplished are described below, and include *Agrobacterium*-mediated transformation (of dicots—e.g. Salomon et al. *EMBO J.* 3:141 (1984); Herrera-Estrella et al. *EMBO J.* 2:987 (1983); of monocots, representative papers are those by Escudero et al., *Plant J.* 10:355 (1996), Ishida et al., *Nature Biotechnology* 14:745 (1996), May et al., *Bio/Technology* 13:486 (1995)), biolistic methods (Armaleo et al., *Current Genetics* 17:97 1990)), electroporation, in planta techniques, and the like. Such a plant containing the exogenous nucleic acid is referred to here as a $T_0$ for the primary transgenic plant and $T_1$ for the first generation. The term "exogenous" as used herein is also intended to encompass inserting a naturally found element into a non-naturally found location.

Flood: Plant species vary in their capacity to tolerate flooding. Some plants, such as rice, are cultivated in water while plants such as corn do not tolerate flooding.

"Flood," as referred to within, is the state of water saturation at which soils become hypoxic or anoxic, thus limiting respiration in the root. Reduced respiration damages roots and can limit the permeability of roots to water, resulting in decreased leaf water potential and wilting. Since plant species vary in their capacity to tolerate flooding, the precise environmental conditions that cause flood stress can not be generalized. However, flood tolerant plants are characterized by their ability to retain their normal appearance or recover quickly from flood. Such flood tolerant plants produce higher biomass and yield than plants that are not flood tolerant. Differences in physical appearance, recovery and yield can be quantified and statistically analyzed using well known measurement and analysis methods.

Functionally Comparable Proteins: This phrase describes those proteins that have at least one characteristic in common. Such characteristics include sequence similarity, biochemical activity, transcriptional pattern similarity and phenotypic activity. Typically, the functionally comparable proteins share some sequence similarity or at least one biochemical and within this definition, homologs, orthologs and analogs are considered to be functionally comparable. In addition, functionally comparable proteins generally share at least one biochemical and/or phenotypic activity.

Functionally comparable proteins will give rise to the same characteristic to a similar, but not necessarily to the same degree. Typically, comparable proteins give the same characteristics where the quantitative measurement due to one of the comparables is at least 20% of the other; more typically, between 30 to 40%; even more typically, between 50-60%; even more typically, 70 to 80%; even more typically between 90 to 100%.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence originates from, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

High Temperature: Plant species vary in their capacity to tolerate high temperatures. Very few plant species can survive temperatures higher than 45° C. The effects of high temperatures on plants, however, can begin at lower temperatures depending on the species and other environmental conditions such as humidity and soil moisture. "High temperature" can be defined as the temperature at which a given plant species will be adversely affected as evidenced by symptoms such as decreased photosynthesis. Since plant species vary in their capacity to tolerate high temperature, the precise environmental conditions that cause high temperature stress can not be generalized. However, high temperature tolerant plants are characterized by their ability to retain their normal appearance or recover quickly from high temperature conditions. Such high temperature tolerant plants produce higher biomass and yield than plants that are not high temperature tolerant. Differences in physical appearance, recovery and yield can be quantified and statistically analyzed using well know measurement and analysis methods.

Inducible Promoter: An "inducible promoter" in the context of the current invention refers to a promoter which is regulated under certain conditions, such as light, chemical concentration, protein concentration, conditions in an organism, cell, or organelle, etc. A typical example of an inducible promoter, which can be utilized with the polynucleotides of the present invention, is PARSK1, the promoter from the *Arabidopsis* gene encoding a serine-threonine kinase enzyme, and which promoter is induced by dehydration, abscissic acid and sodium chloride (Wang and Goodman, *Plant J.* 8:37 (1995)). Examples of environmental conditions that may affect transcription by inducible promoters include anaerobic conditions, elevated temperature, or the presence of light.

Low Temperature: Plant species vary in their capacity to tolerate low temperatures. Chilling-sensitive plant species, including may agronomically important species, can be injured by cold, above-freezing temperatures. At temperatures below the freezing-point of water most plant species will be damaged. Thus, "low temperature" can be defined as the temperature at which a given plant species will be adversely affected as evidenced by symptoms such as decreased photosynthesis and membrane damage (measured by electrolyte leakage). Since plant species vary in their capacity to tolerate low temperature, the precise environmental conditions that cause low temperature stress can not be generalized. However, low temperature tolerant plants are characterized by their ability to retain their normal appearance or recover quickly from low temperature conditions. Such low temperature tolerant plants produce higher biomass and yield than plants that are not low temperature tolerant. Differences in physical appearance, recovery and yield can be quantified and statistically analyzed using well known measurement and analysis methods.

Plant seeds vary considerably in their ability to germinate under low temperature conditions. Seeds of most plant species will not germinate at temperatures less than 10° C. Once seeds have imbibed water they become very susceptible to disease, water and chemical damage. Seeds that are tolerant to low temperature stress during germination can survive for relatively long periods under which the temperature is too low to germinate. Since plant species vary in their capacity to tolerate low temperature during germination, the precise environmental conditions that cause low temperature stress during germination can not be generalized. However, plants that tolerate low temperature during germination are characterized by their ability to remain viable or recover quickly from low temperature conditions. Such low temperature tolerant plants produce, germinate, become established, grow more quickly and ultimately produce more biomass and yield than plants that are not low temperature tolerant. Differences in germination rate, appearance, recovery and yield can be quantified and statistically analyzed using well known measurement and analysis methods.

Masterpool: The "master pools" discussed in these experiments are a pool of seeds from five different transgenic plants transformed with the same exogenous gene.

Misexpression: The term "misexpression" refers to an increase or a decrease in the transcription of a coding region into a complementary RNA sequence as compared to the wild-type. This term also encompasses expression of a gene or coding region for a different time period as compared to the wild-type and/or from a non-natural location within the plant genome.

Percentage of sequence identity: "Percentage of sequence identity," as used herein, is determined by comparing two optimally aligned sequences over a comparison window, where the fragment of the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman *Add. APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*USA*) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, WI), or by inspection. Given that two sequences have been identified for comparison, GAP and BESTFIT are preferably employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Query nucleic acid and amino acid sequences were searched against subject nucleic acid or amino acid sequences residing in public or proprietary databases. Such searches were done using the Washington University Basic Local Alignment Search Tool Version 1.83 (WU-Blast2) program. The WU-Blast2 program is available on the internet from Washington University. A WU-Blast2 service for *Arabidopsis* can also be found on the internet. Typically the following parameters of WU-Blast2 were used: Filter options were set to "default," Output format was set to "gapped alignments," the Comparison Matrix was set to "BLOSUM62," Cutoff Score (S value) was set to "default," the Expect (E threshold) was set to "default," the Number of best alignments to show was set to "100," and the "Sort output" option was set to sort the output by "pvalue."

Plant Promoter: A "plant promoter" is a promoter capable of initiating transcription in plant cells and can drive or facilitate transcription of a nucleotide sequence or fragment thereof of the instant invention. Such promoters need not be of plant origin. For example, promoters derived from plant viruses, such as the CaMV35S promoter or from *Agrobacterium tumefaciens* such as the T-DNA promoters, can be plant promoters. A typical example of a plant promoter of plant origin is the maize ubiquitin-1 (ubi-1) promoter known to those of skill.

Specific Promoter: In the context of the current invention, "specific promoters" refers to promoters that have a high preference for being active in a specific tissue or cell and/or at a specific time during development of an organism. By "high preference" is meant at least 3-fold, preferably 5-fold, more preferably at least 10-fold still more preferably at least 20-fold, 50-fold or 100-fold increase in transcription in the desired tissue over the transcription in any other tissue. Typical examples of temporal and/or tissue specific promoters of plant origin that can be used with the polynucleotides of the present invention, are: SH-EP from *Vigna mungo* and EP-C1 from *Phaseolus vulgaris* (Yamauchi et al. (1996) *Plant Mol Biol.* 30(2):321-9.); RCc2 and RCc3, promoters that direct root-specific gene transcription in rice (Xu et al., *Plant Mol. Biol.* 27:237 (1995) and TobRB27, a root-specific promoter from tobacco (Yamamoto et al. (1991) *Plant Cell* 3:371).

Stringency: "Stringency" as used herein is a function of probe length, probe composition (G+C content), and salt concentration, organic solvent concentration, and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m-5°$ C. to $T_m-10°$ C. Medium or moderate stringency conditions are those providing $T_m-20°$ C. to $T_m-29°$ C. Low stringency conditions are those providing a condition of $T_m-40°$ C. to $T_m-48°$ C. The relationship of hybridization conditions to $T_m$ (in $°$ C.) is expressed in the mathematical equation $$T_m = 81.5 - 16.6(\log_{10}[Na^+]) + 0.41(\% \, G+C) - (600/N) \quad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m = 81.5 + 16.6 \log \{[Na^+]/(1+0.7[Na^+])\} + 0.41(\% \, G+C) - 500/L \; 0.63(\% \text{ formamide}) \quad (2)$$

where L is the length of the probe in the hybrid. (P. Tijessen, "Hybridization with Nucleic Acid Probes" in Laboratory Techniques in Biochemistry and Molecular Biology, P.C. vand der Vliet, ed., c. 1993 by Elsevier, Amsterdam.) The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al., *J. Mol. Biol.* 81:123 (1973)), stringency conditions can be adjusted to favor detection of identical genes or related family members.

Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

Superpool: As used in the context of the current invention, a "superpool" refers to a mixture of seed from 100 different "master pools". Thus, the superpool contains an equal amount of seed from 500 different events, but only represents 100 transgenic plants with a distinct exogenous nucleotide sequence transformed into them, because the master pools are of 5 different events with the same exogenous nucleotide sequence transformed into them.

$T_0$: As used in the current application, the term "$T_0$" refers to the whole plant, explant or callus tissue inoculated with the transformation medium.

$T_1$: As used in the current application, the term $T_1$ refers to either the progeny of the $T_0$ plant, in the case of whole-plant transformation, or the regenerated seedling in the case of explant or callous tissue transformation.

$T_2$: As used in the current application, the term $T_2$ refers to the progeny of the $T_1$ plant. $T_2$ progeny are the result of self-fertilization or cross pollination of a $T_1$ plant.

$T_3$: As used in the current application, the term $T_3$ refers to second generation progeny of the plant that is the direct result of a transformation experiment. $T_3$ progeny are the result of self-fertilization or cross pollination of a $T_2$ plant.

2. Important Characteristics of the Polynucleotides and Polypeptides of the Invention The polynucleotides and polypeptides of the present invention are of interest because when they are misexpressed (i.e. when expressed at a non-natural location or in an increased or decreased amount) they produce plants with modified water use efficiency. "Water use efficiency" is a term that includes various responses to environmental conditions that affect the amount of water available to the plant. For example, under high heat conditions water is rapidly evaporated from both the soil and from the plant itself, resulting in a decrease of available water for maintaining or initiating physiological processes. Likewise, water availability is limited during cold or drought conditions or when there is low water content in the soil. Interestingly, flood conditions also affect the amount of water available to the plant because it damages the roots and thus limits the plant's ability to transport water to the shoot. As used herein, modulating water use efficiency is intended to encompass all of these situations as well as other environmental situations that affect the plant's ability to use and/or maintain water effectively (e.g. osmotic stress, salinity, etc.).

The polynucleotides and polypeptides of the invention, as discussed below and as evidenced by the results of various experiments, are useful for modulating water use efficiency. These traits can be used to exploit or maximize plant products for agricultural, ornamental or forestry purposes in different environment conditions of water supply. Modulating the expression of the nucleotides and polypeptides of the present invention leads to transgenic plants that will require less water and result in better yield in high heat and/or drought conditions, or that have increased tolerance levels for an excess of water and result in better yield in wet conditions. Both categories of transgenic plants lead to reduced costs for the farmer and better yield in their respective environmental conditions.

3. The Polynucleotides and Polypeptides of the Invention

The polynucleotides of the invention, and the proteins expressed thereby, are set forth in the Sequence Listing. Some of these sequences are functionally comparable proteins.

Functionally comparable proteins are those proteins that have at least one characteristic in common. Such characteristics can include sequence similarity, biochemical activity and phenotypic activity. Typically, the functionally comparable proteins share some sequence similarity and generally share at least one biochemical and/or phenotypic activity. For example, biochemical functionally comparable proteins are proteins that act on the same reactant to give the same product.

Another class of functionally comparable proteins is phenotypic functionally comparable proteins. The members of this class regulate the same physical characteristic, such as increased drought tolerance. Proteins can be considered phenotypic functionally comparable proteins even if the proteins give rise to the same physical characteristic, but to a different degree.

The polypeptides of the invention also include those comprising the consensus sequences described in Tables 1-4, 2-8, 3-9, 5-8, 6-8, 7-6, 8-7, 10-6 and 11-6. A consensus sequence defines the important conserved amino acids and/or domains within a polypeptide. Thus, all those sequences that conform to the consensus sequence are suitable for the same purpose. Polypeptides comprised of a sequence within and defined by one of the consensus sequences can be utilized for the purposes of the invention namely to make transgenic plants with improved water use efficiency, including improved tolerance to heat or high or low water conditions.

4. Use of the Polynucleotides and Polypeptides to Make Transgenic Plants

To use the sequences of the present invention or a combination of them or parts and/or mutants and/or fusions and/or variants of them, recombinant DNA constructs are prepared which comprise the polynucleotide sequences of the invention inserted into a vector, and which are suitable for transformation of plant cells. The construct can be made using standard recombinant DNA techniques (Sambrook et al. 1989) and can be introduced to the species of interest by *Agrobacterium*-mediated transformation or by other means of transformation as referenced below.

The vector backbone can be any of those typical in the art such as plasmids, viruses, artificial chromosomes, BACs, YACs and PACs and vectors of the sort described by (a) BAC: Shizuya et al., Proc. Natl. Acad. Sci. USA 89: 8794-8797 (1992); Hamilton et al., Proc. Natl. Acad. Sci. USA 93: 9975-9979 (1996);
(b) YAC: Burke et al., Science 236:806-812 (1987);
(c) PAC: Sternberg N. et al., Proc Natl Acad Sci USA. January; 87(1):103-7 (1990);
(d) Bacteria-Yeast Shuttle Vectors: Bradshaw et al., Nucl Acids Res 23: 4850-4856 (1995);
(e) Lambda Phage Vectors: Replacement Vector, e.g., Frischauf et al., J. Mol Biol 170: 827-842 (1983); or Insertion vector, e.g., Huynh et al., In: Glover NM (ed) DNA Cloning: A practical Approach, Vol. 1 Oxford: IRL Press (1985); T-DNA gene fusion vectors:Walden et al., Mol Cell Biol 1: 175-194 (1990); and
(g) Plasmid vectors: Sambrook et al., infra.

Typically, the construct comprises a vector containing a sequence of the present invention with any desired transcriptional and/or translational regulatory sequences, such as promoters, UTRs, and 3' end termination sequences. Vectors can also include origins of replication, scaffold attachment regions (SARs), markers, homologous sequences, introns, etc. The vector may also comprise a marker gene that confers a selectable phenotype on plant cells. The marker typically encodes biocide resistance, particularly antibiotic resistance, such as resistance to kanamycin, bleomycin, hygromycin, or herbicide resistance, such as resistance to glyphosate, chlorosulfuron or phosphinotricin.

A plant promoter is used that directs transcription of the gene in all tissues of a regenerated plant and may be a constitutive promoter, such as p326 or CaMV35S. Alternatively, the plant promoter directs transcription of a sequence of the invention in a specific tissue manner (tissue-specific promoter) or is otherwise under more precise environmental control (inducible promoter). Various plant promoters, including constitutive, tissue-specific and inducible, are known to those skilled in the art and can be utilized in the present invention. Typically, preferred promoters to use in the present invention are those that are induced by heat or low water conditions Such as the RD29a promoter (Kasuga et al., *Plant Cell Physiol.* 45:346 (2004) and Yamaguchi-Shinozaki and Shinozaki, *Mol Gen Genet.* 236: 331 (1993)) or other DRE-containing (dehydration-responsive elements) promoters (Liu et al, Cell 10: 1391 (1998)). Another preferred embodiment of the present invention is the use of root specific promoters such as those present in the AtXTH17, AtXTH18, AtXTH19 and AtXTH20 genes of *Arabidopsis* (Vissenberg et al. (2005) *Plant Cell Physiol* 46:192) or guard cell specific promoters such as TGG1 or KST1 (Husebye et al. (2002) *Plant Physiol* 128:1180; Plesch et al. (2001) *Plant J* 28:455).

Alternatively, misexpression can be accomplished using a two component system, whereby the first component comprises a transgenic plant comprising a transcriptional activator operatively linked to a promoter and the second component comprises a transgenic plant comprising a sequence of the invention operatively linked to the target binding sequence/region of the transcriptional activator. The two transgenic plants are crossed and the sequence of the invention is expressed in their progeny. In another alternative, the misexpression can be accomplished by transforming the sequences of the two component system into one transgenic plant line.

Any promoter that functions in plants can be used in the first component, such as those discussed above. Suitable transcriptional activator polypeptides include, but are not limited to, those encoding HAP1 and GAL4. The binding sequence recognized and targeted by the selected transcriptional activator protein (e.g. a UAS element) is used in the second component.

Transformation

Nucleotide sequences of the invention are introduced into the genome or the cell of the appropriate host plant by a variety of techniques. These techniques for transforming a wide variety of higher plant species are well known and described in the technical and scientific literature. See, e.g.

Weising et al., *Ann. Rev. Genet.* 22:421 (1988); and Christou, Euphytica, v. 85, n.1-3:13-27, (1995).

Processes for the transformation and regeneration of monocotyledonous and dicotyledonous plants are known to the person skilled in the art. For the introduction of DNA into a plant host cell a variety of techniques is available. These techniques include transformation of plant cells by injection (e.g. Newell, 2000), microinjection (e.g. Griesbach (1987) *Plant Sci.* 50 69-77), electroporation of DNA (e.g. Fromm et al. (1985) *Proc. Natl Acad. Sci. USA* 82:5824 and Wan and Lemaux, Plant Physiol. 104 (1994), 37-48), PEG (e.g. Paszkowski et al. (1984) *EMBO J.* 3:2717), use of biolistics (e.g. Klein et al. (1987) *Nature* 327:773), fusion of cells or protoplasts (Willmitzer, L., 1993 Transgenic plants. In: Biotechnology, A Multi-Volume Comprehensive Treatise (H. J. Rehm, G. Reed, A. Pühler, P. Stadler, eds., Vol. 2, 627-659, VCH Weinheim-New York-Basel-Cambridge), via T-DNA using *Agrobacterium tumefaciens* (e.g. Fraley et al. (Crit. Rev. Plant. Sci. 4, 1-46 and Fromm et al., Biotechnology 8 (1990), 833-844) or *Agrobacterium rhizogenes* (e.g. Cho et al. (2000) *Planta* 210:195-204) or other bacterial hosts (e.g. Brootghaerts et al. (2005) Nature 433:629-633), as well as further possibilities.

In addition, a number of non-stable transformation methods well known to those skilled in the art may be desirable for the present invention. Such methods include, but are not limited to, transient expression (e.g. Lincoln et al. (1998) *Plant Mol. Biol. Rep.* 16:1-4) and viral transfection (e.g. Lacomme et al. (2001) In "Genetically Engineered Viruses" (C. J. A. Ring and E. D. Blair, Eds). Pp. 59-99, BIOS Scientific Publishers, Ltd. Oxford, UK).

Seeds are obtained from the transformed plants and used for testing stability and inheritance. Generally, two or more generations are cultivated to ensure that the phenotypic feature is stably maintained and transmitted.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The nucleic acids of the invention can be used to confer the trait of increased tolerance to heat and/or low water conditions, without reduction in fertility, on essentially any plant.

The nucleotide sequences according to the invention encode appropriate proteins from any organism, in particular from plants, fungi, bacteria or animals.

The process according to the invention can be applied to any plant, preferably higher plants, pertaining to the classes of Angiospermae and Gymnospermae. Plants of the subclasses of the Dicotylodenae and the Monocotyledonae are particularly suitable. Dicotyledonous plants belong to the orders of the Magniolales, Illiciales, Laurales, Piperales Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales. Monocotyledonous plants belong to the orders of the Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales. Plants belonging to the class of the Gymnospermae are Pinales, Ginkgoales, Cycadales and Gnetales.

The method of the invention is preferably used with plants that are interesting for agriculture, horticulture, biomass for bioconversion and/or forestry. Examples are tobacco, oilseed rape, sugar beet, potato, tomato, cucumber, pepper, bean, pea, citrus fruit, apple, pear, berries, plum, melon, eggplant, cotton, soybean, sunflower, rose, poinsettia, petunia, guayule, cabbage, spinach, alfalfa, artichoke, corn, wheat, rye, barley, grasses such as switch grass or turf grass, millet, hemp, banana, poplar, eucalyptus trees, conifers.

Homologs Encompassed by the Invention

Sequences of the invention include proteins comprising at least about a contiguous 10 amino acid region preferably comprising at least about a contiguous 20 amino acid region, even more preferably comprising at least about a contiguous 25, 35, 50, 75 or 100 amino acid region of a protein of the present invention. In another preferred embodiment, the proteins of the present invention include between about 10 and about 25 contiguous amino acid region, more preferably between about 20 and about 50 contiguous amino acid region, and even more preferably between about 40 and about 80 contiguous amino acid region.

Due to the degeneracy of the genetic code, different nucleotide codons may be used to code for a particular amino acid. A host cell often displays a preferred pattern of codon usage. Nucleic acid sequences are preferably constructed to utilize the codon usage pattern of the particular host cell. This generally enhances the expression of the nucleic acid sequence in a transformed host cell. Any of the above described nucleic acid and amino acid sequences may be modified to reflect the preferred codon usage of a host cell or organism in which they are contained. Modification of a nucleic acid sequence for optimal codon usage in plants is described in U.S. Pat. No. 5,689,052. Additional variations in the nucleic acid sequences may encode proteins having equivalent or superior characteristics when compared to the proteins from which they are engineered.

It is understood that certain amino acids may be substituted for other amino acids in a protein or peptide structure (and the nucleic acid sequence that codes for it) without appreciable change or loss of its biological utility or activity. The amino acid changes may be achieved by changing the codons of the nucleic acid sequence.

It is well known in the art that one or more amino acids in a native sequence can be substituted with other amino acid(s), the charge and polarity of which are similar to that of the native amino acid, i.e., a conservative amino acid substitution, resulting in a silent change. Conservative substitutes for an amino acid within the native polypeptide sequence can be selected from other members of the class to which the amino acid belongs (see below). Amino acids can be divided into the following four groups: (1) acidic (negatively charged) amino acids, such as aspartic acid and glutamic acid; (2) basic (positively charged) amino acids, such as arginine, histidine, and lysine; (3) neutral polar amino acids, such as glycine, serine, threonine, cysteine, cystine, tyrosine, asparagine, and glutamine; and (4) neutral nonpolar (hydrophobic) amino acids such as alanine, leucine, isoleucine, valine, proline, phenylalanine, tryptophan, and methionine.

In a further aspect of the present invention, nucleic acid molecules of the present invention can comprise sequences that differ from those encoding a protein or fragment thereof selected from the group consisting of the sequences present in the Sequence Listing due to the fact that the different nucleic acid sequence encodes a protein having one or more conservative amino acid changes.

In another aspect, biologically functional equivalents of the proteins or fragments thereof of the present invention can have about 10 or fewer conservative amino acid changes, more preferably about 7 or fewer conservative amino acid changes, and most preferably about 5 or fewer conservative amino acid changes. In a preferred embodiment, the protein has between about 5 and about 500 conservative changes, more preferably between about 10 and about 300 conservative changes, even more preferably between about 25 and about 150 conservative changes, and most preferably between about 5 and about 25 conservative changes or between 1 and about 5 conservative changes.

5. Experiments Confirming the Usefulness of the Polynucleotides and Polypeptides of the Invention 5.1 Procedures The nucleotide sequences of the invention were identified by use of a variety of screens for modified water conditions, including heat and/or low water conditions. These screens are recognized by those skilled in the art to be predictive of nucleotide sequences that provide plants with improved water use efficiency including improved tolerance to heat and/or low water conditions because they emulate the different environmental conditions that can result from increased heat and/or low water conditions. These screens generally fall into two categories (1) soil screens and (2) in vitro screens.

Soil screens have the advantage of assaying the response of the entire plant to particular conditions, such as drought or high heat. On the other hand, in vitro screens have the advantage of relying on defined media and so allow more defined manipulation of growth conditions. "Surrogate" in vitro screens use particular chemicals to alter the water available to the plant by manipulating the concentrations and/or components of the growth media. For example, the ability of the plant to maintain the water concentration within its cells, which can occur during times of low water in the soil, can be tested by growing plants on high sucrose media. Such a screen thus allows one to separate the effects of water loss from roots from, for example, the water loss from leaves during high heat conditions. Each of the screens used is described in more detail below.

In general, the screens used to identify the polynucleotides and polypeptides of the invention were conducted using superpools of *Arabidopsis* $T_2$ transformed plants. The $T_1$ plants were transformed with a Ti plasmid containing a particular SEQ ID NO in the sense orientation relative to a constitutive promoter and harboring the plant-selectable marker gene phosphinothricin acetyltransferase (PAT), which confers herbicide resistance to transformed plants. For surrogate screens, seed from multiple superpools (1,200 $T_2$ seeds from each superpool) were tested. $T_3$ seed were collected from the resistant plants and retested on all other surrogate screens. The results of the screens conducted for each SEQ ID NO can be found in the Examples below.

5.1.1. Mannitol

Screens for mannitol resistant seedlings are surrogate screens for drought (see Quesada et al., Genetic analysis of salt-tolerant mutants in *Arabidopsis thaliana*. Genetics. 2000 154:421-36).

Seeds are sterilized in 30% household bleach for 5 minutes and then washed with double distilled deionized water three times. Sterilized seed is stored in the dark at 4° C. for a minimum of 3 days before use.

Manitol media is prepared by mixing 375 ml sterile 1 mM mannitol with 375 ml sterile 1×MS. Approximately 1200 seeds are evenly spaced per PEG plate before incubating at 22° C. for 14 days.

Putative mannitol-resistant seedlings are transferred to MS with 3% sucrose for recovery. Approximately one week later, resistant seedlings are transferred to soil and sprayed with Finale. Finale resistant plants are genotyped as described below.

DNA is isolated from each plant and used in PCR reactions using the following cycling conditions 95° C. for 30 sec, five cycles of 51° C. for 30 sec, 72° C. for 1.15 min, 95° C. for 30 sec, 25 cycles of 48° C. for 30 sec, 72° C. for 1.15 min, 72° C. for 7 min and 4° C. hold. Aliquots of the reaction product are analyzed on a 1.2% agarose gel stained with ethidium bromide.

$T_3$ Seed from those plants containing the expected PCR product are collected and retested on 375 mM mannitol media.

5.1.2. Polyethylene Glycol (PEG)

Screens for PEG resistant seedlings are surrogate screens for drought (see van der Weele et al., Growth of *Arabidopsis thaliana* seedlings under water deficit studied by control of water potential in nutrient-agar media. *J Exp Bot.* 2000 51(350):1555-62).

Seeds are sterilized in 30% household bleach for 5 minutes and then washed with double distilled deionized water three times. Sterilized seed is stored in the dark at 4° C. for a minimum of 3 days before use.

18% PEG media is prepared by mixing 360 ml of hot sterile 50% PEG with 400 ml of hot sterile 0.5×MS media. Approximately 1200 seeds are evenly spaced per PEG plate before incubating at 22° C. for 14 days.

Putative PEG-resistant seedlings are transferred to MS with 0.01% Finale. One week later, resistant seedlings are transferred to soil. Three days later the seedlings are genotyped as described below.

DNA is isolated from each plant and used in PCR reactions using the following cycling conditions 95° C. for 30 sec, five cycles of 51° C. for 30 sec, 72° C. for 1.15 min, 95° C. for 30 sec, 25 cycles of 48° C. for 30 sec, 72° C. for 1.15 min, 72° C. for 7 min and 4° C. hold. Aliquots of the reaction product are analyzed on a 1.2% agarose gel stained with ethidium bromide.

$T_3$ Seed from those plants containing the expected PCR product are collected and retested using 20% PEG media.

5.1.3. Soil Drought

Soil drought screens identify plants with enhanced tolerance to drought and enhanced recovery after drought.

Seeds are planted in holed flats containing Zonolite vermiculite that are placed in no-holed flats. Flats are watered with 3 L of Hoagland's solution and covered with a plastic dome before being placed at 4° C. After 4 days, the flats are moved to the Greenhouse (22° C.) and grown 2 weeks, with 1.5 L Hoagland's solution being added every 4 days, or when top of vermiculite is dry. The final application of Hoagland's solution is 4 days prior to the end of the 2 weeks. After 2 weeks, 1 L Hoagland's solution is added to the no-holed flat. After 10 days plants are wilted but still green.

Green, turgid plants are transplanted to 4" square pots containing 60% sunshine mix #5 and 40% thermo-o-rock vermiculite, with Osmocote (1 tbsp/8 L) and Marathon (1 tbsp/8 L). The soil is moistened and the pots sub-irrigated with water. They are grown under a plastic dome for one day, then the plastic dome is removed for the remaining growth period.

To assess plants for enhanced recovery after drought the green wilted plants remaining in the flats are sub-irrigated with 2.5 L Hoagland's solution and cover with cleared with a plastic dome. The following day, the dome is removed and green survivors transplanted to 4" square pots containing 60% sunshine mix #5, 40% Therm-o-rock vermiculite, Osmocote (1 tbsp/8 L) and marathon (1 tbsp/8 L). The soil is moistened and the pots sub-irrigated with water. They are grown under a plastic dome for one day, then the plastic dome is removed for the remaining growth period.

DNA from a leaf from each plant is transferred to FTA paper via pressure and an aliquot of the DNA containing paper used in PCR reactions using the following cycling conditions 94° C. for 10 min, five cycles of 94° C. for 30 sec, 60° C. for 30 sec, 72° C. for 3 min, five cycles of 94° C. for 30 sec, 60° C. for 30 sec, 72° C. for 3 min, 30 cycles of 94° C. for 30 sec, 53° C. for 30 sec, 72° C. for 3 min, 72° C. for 7 min and 4° C. hold. Aliquots of the reaction product are analyzed on a 1% agarose gel stained with ethidium bromide.

$T_3$ Seed from those plants containing the expected PCR product are collected and retested using 50 seeds from each line.

5.1.4. Heat

High heat screens identify plants with enhanced tolerance to heat and enhanced recovery after heat.

Seeds are sterilized in 30% household bleach for 5 minutes and then washed with double distilled deionized water three times. Sterilized seed is stored in the dark at 4° C. for a minimum of 3 days before use.

MS media, pH 5.7 is prepared. Approximately 12 seeds are evenly spaced per MS plate before incubating in the vertical position at 22° C. for 14 days. Under these conditions, the plates are exposed to 12,030 LUX from above and 3,190 LUX from the bottom.

On day 15 the plates are transferred to a 22° C. oven, which increased temperature in 5° C. increments to 45° C. The duration of treatment at 45° C. was based on complete and homogenous wilting of 100 wild-type seedlings (~10 plates). After exposure to 45° C., seedlings were placed in the horizontal position at 23° C. for recovery, where they remained for 4-11 days. Heat recovery was assessed based on vigor and greenness and continued growth after treatment.

Leaves of control and non-resistant plants become wilted and yellowed after only 2 days, completely bleaching after an additional 4 days. All wild type (WS) and non-heat resistant plants die by day 6.

DNA is isolated from each plant and used in PCR reactions using the following cycling conditions 95° C. for 30 sec, five cycles of 51° C. for 30 sec, 72° C. for 1.15 min, 95° C. for 30 sec, 25 cycles of 48° C. for 30 sec, 72° C. for 1.15 min, 72° C. for 7 min and 4° C. hold. Aliquots of the reaction product are analyzed on a 1.2% agarose gel stained with ethidium bromide.

$T_3$ Seed from those plants containing the expected PCR product are collected and retested.

To differentiate between natural acquired thermo tolerance of recovered $T_3$ events, seeds were sterilized and stratified in parallel to wildtype seed that was never heat treated and wild-type controls previously heat treated with the $T_2$ events. 15 day old seedlings were heat shocked in the dark at 45° C. for 5 hours, as described above. Duration of treatment at 45° C. was based on complete and homogenous wilting of pre-heat treated wild-type seed and un-pretreated wild-type controls. After exposure to 45° C., seedlings were returned to the permissive temperature of 23° C. for recovery where they remained for another 7 days. Thermo tolerance was assessed based on prolonged greenness and continued growth after treatment.

5.1.5 Heat (Soil)

Seeds are sown in pots containing soil of the following composition: 60% autoclaved Sunshine Mix #5, 40% vermiculite with 2.5 Tbsp Osmocote and 2.5 Tbsp 1% granular Marathon per 25 L of soil. After sowing, pots are covered with plastic propagation domes and seed is placed at 4° C. in the dark for at least 3 days. Pots are then returned to the greenhouse (long day light conditions of 16 hours), covered with 55% shade cloth and provided a normal watering regime.

After 7 days, seedlings were transferred to a 36° C. growth chamber under continuous light and allowed to grow until harvest. Plants were watered minimally so as to allow for some drying of the top soil similar to that in heat-induced drought conditions in the field.

Plants are sprayed with a mixture of 3 ml Finale in 48 oz of water. Spraying is repeated every 3-4 days until only transformants remain. The remaining transformants were weeded to a maximum of 5 evenly spaced transformants per pot.

T3 seed was recovered and tested for thermotolerance and recovery as described above.

5.1.6 High Sucrose

Screens for germination and growth on limited nutrients and 9% sucrose are surrogate screens for the altered carbon/nitrogen balance frequently associated with drought (see Laby et al., The *Arabidopsis* sugar-insensitive mutants sis4 and sis5 are defective in abscisic acid synthesis and response. *Plant Journal* 23: 587-596).

Seeds are sterilized in 30% household bleach for 5 minutes and then washed with double distilled deionized water three times. Sterilized seed is stored in the dark at 4° C. for a minimum of 3 days before use.

MS media containing 9% sucrose is prepared. Approximately 1200 seeds are evenly spaced per MS-sucrose plate before incubating at 22° C. for 9 days.

Putative sucrose-resistant green seedlings are transferred to MS plates. After one week of recovery, resistant the seedlings are genotyped as described below.

DNA from a leaf from each plant is transferred to FTA paper via pressure and an aliquot of the DNA containing paper used in PCR reactions using the following cycling conditions 94° C. for 10 min, five cycles of 94° C. for 30 sec, 60° C. for 30 sec, 72° C. for 3 min, five cycles of 94° C. for 30 sec, 60° C. for 30 sec, 72° C. for 3 min, 30 cycles of 94° C. for 30 sec, 53° C. for 30 sec, 72° C. for 3 min, 72° C. for 7 min and 4° C. hold. Aliquots of the reaction product are analyzed on a 1% agarose gel stained with ethidium bromide.

$T_3$ Seed from those plants containing the expected PCR product are collected and retested using 9% sucrose MS media.

5.1.7. ABA

Screens for ABA resistant seedlings are surrogate screens for drought.

Seeds are sterilized in 30% household bleach for 5 minutes and then washed with double distilled deionized water three times. Sterilized seed is stored in the dark at 4° C. for a minimum of 3 days before use.

MS media containing 1.5 μM ABA is prepared. Approximately 1200 seeds are evenly spaced per PEG plate before incubating at 22° C. for 14 days.

Putative ABA-resistant seedlings are transferred to MS with 0.01% Finale. One week later, resistant seedlings are transferred to soil. Three days later the seedlings are genotyped as described below.

DNA is isolated from each plant and used in PCR reactions using the following cycling conditions 95° C. for 30 sec, five cycles of 51° C. for 30 sec, 72° C. for 1.15 min, 95° C. for 30 sec, 25 cycles of 48° C. for 30 sec, 72° C. for 1.15 min, 72° C. for 7 min and 4° C. hold. Aliquots of the reaction product are analyzed on a 1.2% agarose gel stained with ethidium bromide.

$T_3$ Seed from those plants containing the expected PCR product are collected and retested using 1.5 μM ABA MS media.

5.1.8. Procedure for Identifying Functional Homologs and Consensus Sequences

The isolated sequence of the invention was compared to the sequences present in the various gene banks. Pairwise comparisons were conducted and those sequences having the highest percent identity to the query sequence identified as functional homologs.

A multi-pairwise alignment was generated using the amino acid query sequence and the amino acid sequence of the functional homologs. This allowed identification of the conserved regions or domains of the polypeptide. Using the conserved regions as a guide, a consensus sequence was generated. This consensus sequence indicates the critical amino acid residues and those can be either substituted and/or deleted without impacting the biological function of the protein.

5.2 Results

The results of the above experiments are set forth below wherein each individual example relates to all of the experimental results for a particular polynucleotide/polypeptide of the invention.

Example 1—Ceres cDNA 12331850

Clone 11830, Ceres cDNA 12331850, encodes a full-length glycosyl hydrolase family 17 protein, which has similarity to elicitor inducible chitinase Nt-SubE76 GI:11071974 from (*Nicotiana tabacum* (C-terminal homology only) and β-1,3-glucanase.

Ectopic expression of Ceres cDNA 12331850 under the control of the CaMV35S or 32449 promoter induces the following phenotypes:

Germination on high concentrations of polyethylene glycol (PEG), mannitol, and abscissic acid (ABA).

Continued growth on high concentration of PEG, mannitol, and ABA.

Generation and Phenotypic Evaluation of $T_1$ Lines Containing 35S::cDNA 12331850.

Wild-type *Arabidopsis* Wassilewskija (WS) plants were transformed with a Ti plasmid containing cDNA 12331850 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol, and ABA as Surrogate Screens for Drought Tolerance.

Seeds from 13 superpools (1,200 $T_2$ seeds from each superpool) from the CaMV35S or 32449 over-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 12331850 was identified in resistant plants from each of the three surrogate drought screens, the five individual $T_2$ events containing this cDNA (ME01297) were screened on high PEG, mannitol, and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the 18$^{th}$ plant isolated from a mannitol screen of Superpool 1.

Results:

Qualitative Analysis of 13 Superpools on PEG, Mannitol, and ABA

Resistant candidates were selected based on increased size compared to the largest wild-type control. All three screens resulted in a decrease in germination for both wildtype and superpools as compared to seeds on control media. Wild-type seeds that germinated on any of the screens were small and never developed any first leaves even after 40 days. To ensure that even slightly tolerant individuals were not omitted, seedlings that showed any growth and greening whatsoever were recovered and transferred to soil for assessment in the $T_3$ generation. All recovered candidates showed signs of vigorous re-growth on soil, although the development was slightly delayed as compared to unstressed plants, presumably because of the transient exposure to stress. The plants transferred to soil were sprayed with Basta$^R$ to eliminate any false-positives, or any lines where the Basta$^R$ marker was suppressed. All of the Basta$^R$-resistant candidates flowered and set seed. Resistant seedlings were recovered from Superpools 1, 7 and 11 on all screens (Table 1-1).

TABLE 1-1

Number of Basta$^R$ seedlings identified on several screens.

| Superpool | Promoter | 18% PEG | 375 mM Mannitol | 1.5 uM ABA |
|---|---|---|---|---|
| SP1 | 35S | 10 | 13 | 11 |
| SP2 | 35S | 0 | 6 | 5 |
| SP3 | 35S | 0 | 2 | 10 |
| SP4 | 35S | 0 | 4 | 0 |
| SP5 | 35S | 0 | 0 | 5 |
| SP6 | 35S | 0 | 0 | 4 |
| SP7 | 35S | 1 | 4 | 8 |
| SP8 | 35S | 0 | 4 | 1 |
| SP9 | 32449 | 0 | 0 | 12 |
| SP10 | 32449 | 0 | 0 | 14 |
| SP11 | 32449 | 15 | 3 | 13 |
| SP12 | 32449 | 3 | 0 | 6 |
| SP13 | 32449 | 0 | 2 | 1 |

Qualitative and Quantitative Analysis of 5 Independent Events Representing 35S::cDNA 12331850 on PEG, Mannitol, and ABA Screens.

Seedlings that survived transfer to soil and which were Basta$^R$-resistant were subjected to PCR and sequencing. At least one resistant plant in each of the three screens contained 35S::cDNA 12331850 (ME01297) making this a good candidate for further testing. $T_2$ seeds from the 5 independent transformants that contain this clone and that were used in the pooling process were tested for Basta$^R$ resistance and for stress tolerance in the 3 surrogate drought screens.

To identify two independent events of 35S::cDNA 12331850 showing PEG, mannitol and ABA resistance, 36 seedlings from each of five events, ME01297-01, 02, 03, 04, and 05 were screened as previously described. Simultaneously, Basta$^R$ segregation was assessed to identify events containing a single insert segregating in a 3:1 (R:S) ratio as calculated by a chi-square test (Table 1-2). All of the events segregated for a single functional insert.

TABLE 1-2

Basta segregation for ME01297 individual events

| Event | Resistant | Sensitive | Total | Probability of Chi-test* |
|---|---|---|---|---|
| ME01297-01 | 22 | 14 | 36 | 0.05429 |
| ME01297-02 | 26 | 10 | 36 | 0.70031 |
| ME01297-03 | 25 | 11 | 36 | 0.44142 |
| ME01297-04 | 22 | 14 | 36 | 0.05429 |
| ME01297-05 | 24 | 12 | 36 | 0.24821 |

*Chi-test to determine whether actual ratio of resistant to sensitive differs from the expected 3:1 ratio Events ME01297-02 and 03 were chosen as the two events because they had the strongest and most consistent resistance to PEG, mannitol and ABA. Resistance was observed for ME01297-01, 04, and 05 although not in expected ratios in all three screens (data not shown). The controls were sown the same day and on the same plate as the individual events. The transgenic control in each of these plates is a segregant, from this ME line or another ME line being tested, that failed to show resistance to the particular stress. The PEG, mannitol and ABA (Table 1-3) segregation ratios observed for ME01297-02 and 03 are consistent with the presence of a single insert, similar to what we observed for Basta resistance (Table 1-1).

On 18% PEG, the resistant seedlings from these two events show some root growth and they are green with new leaves emerging. The mannitol resistant seedlings also showed more root and shoot growth than the sensitive seedlings. The ABA resistant seedlings showed a slight increase in growth. The phenotype of the resistant seedlings is unique to each of the screens.

TABLE 1-3

Segregation of Resistance to PEG, mannitol and ABA in ME01297-02 and ME01297-03 Progeny.

| | PEG | | | mannitol | | | ABA | | |
|---|---|---|---|---|---|---|---|---|---|
| | R | S | Probability of Chi-test | R | S | Probability of Chi-test | R | S | Probability of Chi-test |
| ME01297-02 | 49 | 23 | 0.174 | 47 | 25 | 0.057 | 50 | 22 | 0.276 |
| ME01297-03 | 58 | 14 | 0.276 | 51 | 21 | 0.414 | 56 | 16 | 0.586 |
| Expected (3:1 segregation) | 54 | 18 | | 54 | 18 | | 54 | 18 | |

Qualitative and Quantitative Analysis of Progeny of $T_2$ Plants Isolated on High Concentrations of PEG, Mannitol, and ABA Screens.

Progeny from $T_2$ plants that were recovered from the three screens and which contained cDNA 12331850 (SP1-A1, SP1-P1, and SP1-M18) were analyzed and also found to be resistant to PEG, mannitol and ABA indicating that resistance is transmitted to the next generation. Taken together, 1) the isolation of resistant seedlings containing cDNA 12331850 from all three screens, 2) the inheritance of this resistance in a subsequent generation, and 3) the fact that the progeny from two or more events from the original transformation also segregated for resistance to the stresses, provide strong evidence that cDNA 12331850 when overexpressed can provide tolerance to osmotic stress.

This gene is annotated as a glycosyl hydrolase family 17, which has similarity to elicitor inducible chitinase Nt-SubE76 GI: 11071974 from *Nicotiana tabacum* (C-terminal homology only). TIGR also notes that the protein contains similarity to beta-1,3-glucanase.

FIG. 1 provides the results of the consensus sequence (SEQ ID NOs: 112-120) analysis based on Ceres cDNA 12331850.

Example 2—Ceres cDNA 12334963

Clone 35743, Ceres cDNA 12334963, encodes a full-length putative hypothetical protein. Ectopic expression of Ceres cDNA 12334963 under the control of the 35S promoter induces the following phenotypes:

Germination on high concentrations of polyethylene glycol (PEG), mannitol, and abscissic acid (ABA).

Continued growth on high PEG, mannitol, and ABA.

Generation and Phenotypic Evaluation of $T_1$ Lines Containing 35S::cDNA 12334963.

Wild-type *Arabidopsis* Wassilewskija (WS) plants were transformed with a Ti plasmid containing cDNA 12334963 in the sense orientation relative to the CaMV35S constitutive promoter. The $T_1$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol, and ABA as Surrogate Screens for Drought Tolerance.

Seeds from 13 superpools (1,200 $T_2$ seeds from each superpool) from the CaMV35S or 32449 over-expression lines were tested on 3 drought surrogate screens (high concentrations of PEG, mannitol and ABA) as described above. $T_3$ seeds were collected from the resistant plants and analyzed for resistance on all three surrogate drought screens.

Once cDNA 12334963 was identified in resistant plants from each of the three surrogate drought screens, the five individual $T_2$ events containing this cDNA (ME01467) were screened on high PEG, mannitol and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the 18$^{th}$ plant isolated from a mannitol screen of Superpool 1.

Results:

Qualitative Analysis of 13 Superpools on PEG, Mannitol, and ABA.

Resistant candidates were selected based on increased size when compared to the largest wild-type control seedlings. All three screens resulted in a decrease in germination for both wildtype and superpools compared to seeds on control media. Wild-type seeds that germinated on any of the screens were small and never developed any first leaves even after 40 days. To ensure that even slightly tolerant individuals were not omitted, seedlings that showed any growth and greening whatsoever were recovered and transferred to soil for assessment in the $T_3$ generation. All recovered candidates showed signs of vigorous re-growth on soil, although the development was slightly delayed as compared to unstressed plants, presumably because of the transient exposure to stress. The plants transferred to soil were sprayed with Basta$^R$ to eliminate any false-positives, or any lines where the Basta$^R$ marker was suppressed. All of the Basta$^R$-resistant candidates flowered and set seed. Resistant seedlings were recovered from Superpools 1, 7 and 11 on all screens (Table 2-1).

TABLE 2-1

Number of stress-tolerant and Basta$^R$ seedlings identified on drought surrogate screens.

| Superpool | Promoter | 18% PEG | 375 mM Mannitol | 1.5 uM ABA |
|---|---|---|---|---|
| SP1 | 35S | 10 | 13 | 11 |
| SP2 | 35S | 0 | 6 | 5 |
| SP3 | 35S | 0 | 2 | 10 |
| SP4 | 35S | 0 | 4 | 0 |
| SP5 | 35S | 0 | 0 | 5 |
| SP6 | 35S | 0 | 0 | 4 |
| SP7 | 35S | 1 | 4 | 8 |
| SP8 | 35S | 0 | 4 | 1 |
| SP9 | 32449 | 0 | 0 | 12 |
| SP10 | 32449 | 0 | 0 | 14 |
| SP11 | 32449 | 15 | 3 | 13 |
| SP12 | 32449 | 3 | 0 | 6 |
| SP13 | 32449 | 0 | 2 | 1 |

Qualitative and Quantitative Analysis of 5 Independent Events Representing 35S::cDNA 12334963 on PEG, Mannitol, and ABA Seedlings that survived transfer to soil and which were Basta$^R$-resistant were subjected to PCR and sequencing. At least one resistant plant in each of the three osmotic screens contained 35S::cDNA 12334963 (ME01467) making this a good candidate for further testing. $T_2$ seeds from the 5 independent transformants that contain this clone and that were used in the pooling process were tested for Basta$^R$ resistance and for stress tolerance in the 3 surrogate drought screens.

To identify two independent events of 35S::cDNA 12334963 showing PEG, mannitol and ABA resistance, 36 seedlings from each of five events, ME01467-0l, 02, 03, 04, and 05 were screened as previously described. Simultaneously, Basta segregation was assessed to identify events containing a single insert segregating in a 3:1 (R:S) ratio as calculated by a Chi-square test (Table 2-2). All of the lines segregated for a single functional insert.

TABLE 2-2

Basta$^R$ segregation for ME01467 individual events

| Event | Resistant | Sensitive | Total | Probability of Chi-test* |
|---|---|---|---|---|
| ME01467-01 | 28 | 8 | 36 | 0.70031 |
| ME01467-02 | 29 | 7 | 36 | 0.44142 |
| ME01467-03 | 24 | 12 | 36 | 0.24821 |

TABLE 2-2-continued

Basta$^R$ segregation for ME01467 individual events

| Event | Resistant | Sensitive | Total | Probability of Chi-test* |
|---|---|---|---|---|
| ME01467-04 | 28 | 8 | 36 | 0.70031 |
| ME01467-05 | 27 | 9 | 36 | 1 |

*Chi-test to determine whether actual ratio of resistant to sensitive differs from the expected 3:1 ratio.

Events ME01467-03 and 05 were chosen as the two events because had the strongest and most consistent resistance to PEG, mannitol and ABA. Resistance was observed for ME01467-01, 02, and 04, although not in expected ratios in all three screens (data not shown). The controls were sown the same day and in the same plate as the individual events. The transgenic control in each of these plates is a segregant, from this ME line or another ME line being tested, that failed to show resistance to the particular osmotic stress. The PEG (Tables 2-3 and 2-4), mannitol (Tables 2-5 and 2-6) and ABA (Tables 2-7 and 2-8) segregation ratios observed for ME01467-03 and 05 are consistent with the presence of a single insert as demonstrated by Chi-Square. This result is similar to the observation for Basta$^R$ resistance (Table 2-2).

On 18% PEG, the resistant seedlings from these two events showed some root growth but they were also green with emergence of new leaves at day 14. The mannitol-resistant seedlings showed more root and shoot growth than the PEG resistant seedlings. The resistant seedlings on ABA show the least amount of growth, and very little root growth relative to the mannitol and PEG screens. The phenotype

TABLE 2-3

Chi-square analysis assuming a 3:1 (R:S) ratio for progeny of ME01467-03 containing 35S::cDNA 12334963 on PEG.

| Event | Observed | Expected | $\chi^2$ | Probability of Chi-Test |
|---|---|---|---|---|
| PEG Resistant | 24 | 24 | 0 | 1.0 |
| PEG Sensitive | 8 | 8 | 0 | |
| | 32 | 32 | 0 | |

TABLE 2-4

Chi-square analysis assuming a 3:1 (R:S) ratio for progeny of ME01467-05 containing 35S::cDNA 12334963 on PEG.

| Event | Observed | Expected | $\chi^2$ | Probability of Chi-Test |
|---|---|---|---|---|
| PEG Resistant | 26 | 27 | 0.037 | 0.7 |
| PEG Sensitive | 10 | 9 | 0.111 | |
| | 36 | 36 | 0.148 | |

TABLE 2-5

Chi-square analysis assuming a 3:1 (R:S) ratio for progeny of ME01467-03 containing 35S::cDNA 12334963 on mannitol.

| Event | Observed | Expected | $\chi^2$ | Probability of Chi-Test |
|---|---|---|---|---|
| Mannitol Resistant | 29 | 27 | 0.148 | 0.4 |
| Mannitol Sensitive | 7 | 9 | 0.444 | |
| | 36 | 36 | 0.592 | |

TABLE 2-6

Chi-square analysis assuming a 3:1 (R:S) ratio for progeny
of ME01467-05 containing 35S::cDNA 12334963 on mannitol.

| Event | Observed | Expected | $\chi^2$ | Probability of Chi-Test |
|---|---|---|---|---|
| Mannitol Resistant | 18 | 27 | 3 | 0.0005 |
| Mannitol Sensitive | 18 | 9 | 9 | |
| | 36 | 36 | 12 | |

TABLE 2-7

Chi-square analysis assuming a 3:1 (R:S) ratio for progeny
of ME01467-03 containing 35S::cDNA 12334963 on ABA.

| Event | Observed | Expected | $\chi^2$ | Probability of Chi-Test |
|---|---|---|---|---|
| ABA Resistant | 25 | 26.25 | 0.0595 | 0.626 |
| ABA Sensitive | 10 | 8.75 | 0.179 | |
| | 35 | 35 | 0.239 | |

TABLE 2-8

Chi-square analysis assuming a 3:1 (R:S) ratio for progeny
of ME01467-05 containing 35S::cDNA 12334963 on ABA.

| Event | Observed | Expected | $\chi^2$ | Probability of Chi-Test |
|---|---|---|---|---|
| ABA Resistant | 22 | 27 | 0.926 | 0.054 |
| ABA Sensitive | 14 | 9 | 2.78 | |
| | 36 | 36 | 3.706 | |

Qualitative and Quantitative Analysis of Progeny of $T_2$ Plants Isolated on PEG, Mannitol and ABA Progeny of the $T_2$ plants that were recovered from the three screens and which contained cDNA 12334963 (SP1-A12, SP1-P9, and SP1-M4) were analyzed and found to be resistant to PEG, mannitol and ABA, indicating that resistance is transmitted to the next generation.

Taken together, 1) the isolation of resistant seedlings containing cDNA 12334963 from all three surrogate screens for drought, 2) the inheritance of this resistance in the next generation, and 3) the fact that the progeny from two or more events from the original transformation also segregated for resistance to these osmotic stresses, provides strong evidence that cDNA 12334963, when over-expressed, can provide tolerance to drought, freezing and other osmotic stresses.

FIG. 2 provides the results of the consensus sequence (SEQ ID NOs: 121-129) analysis based on Ceres cDNA 12334963.

Example 3—Ceres cDNA 12333678

Clone 26006, Ceres cDNA 12333678, encodes a full-length glycosyl hydrolase. Ectopic expression of Ceres cDNA 12333678 under the control of the CaMV35S promoter induces the following phenotypes:

Germination on high concentrations of polyethylene glycol (PEG), mannitol and abscissic acid (ABA).

Continued growth on high PEG, mannitol and ABA.

Generation and Phenotypic Evaluation of $T_1$ Lines Containing 35S::cDNA 12333678.

Wild-type *Arabidopsis* Wassilewskija (WS) plants were transformed with a Ti plasmid containing cDNA 12333678 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol and ABA as Surrogate Screens for Drought Tolerance.

Seeds from 13 superpools (1,200 $T_2$ seeds from each superpool) from the CaMV35S or 32449 over-expression lines were tested on 3 drought surrogate screens (high concentrations of PEG, mannitol and ABA) as described above. $T_3$ seeds were collected from the resistant plants and analyzed for resistance on all three surrogate drought screens.

Once cDNA 12333678 was identified in resistant plants from each of the three surrogate drought screens, the five individual $T_2$ events containing this cDNA (ME01334) were screened on high PEG, mannitol and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the 18$^{th}$ plant isolated from a mannitol screen of Superpool 1.

Results:

Qualitative Analysis of 13 Superpools on PEG, Mannitol and ABA.

Resistant candidates were selected based on increased size when compared to the largest wild-type control seedlings. All three screens resulted in a decrease in germination for both wildtype and superpools as compared to seeds on control media. Wild-type seeds that germinated on any of the screens were small and never developed any first leaves even after 40 days. To ensure that even slightly tolerant individuals were not omitted, seedlings that showed any growth and greening whatsoever were recovered and transferred to soil for assessment in the $T_3$ generation. All recovered candidates showed signs of vigorous re-growth on soil, although the development was slightly delayed compared to unstressed plants, presumably because of the transient exposure to stress. The plants transferred to soil were sprayed with B Basta$^R$ to eliminate any false-positives, or any lines where the Basta$^R$ marker was suppressed. All of the Basta$^R$-resistant candidates flowered and set seed. Resistant seedlings were recovered from Superpools 1, 7 and 11 on all screens (Table 3-1).

TABLE 3-1

Number of stress-tolerant and Basta$^R$ seedlings
identified on drought surrogate screens.

| Superpool | Promoter | 18% PEG | 375 mM Mannitol | 1.5 uM ABA |
|---|---|---|---|---|
| SP1 | 35S | 10 | 13 | 11 |
| SP2 | 35S | 0 | 6 | 5 |
| SP3 | 35S | 0 | 2 | 10 |
| SP4 | 35S | 0 | 4 | 0 |
| SP5 | 35S | 0 | 0 | 5 |
| SP6 | 35S | 0 | 0 | 4 |
| SP7 | 35S | 1 | 4 | 8 |
| SP8 | 35S | 0 | 4 | 1 |
| SP9 | 32449 | 0 | 0 | 12 |

TABLE 3-1-continued

Number of stress-tolerant and Basta$^R$ seedlings identified on drought surrogate screens.

| Superpool | Promoter | 18% PEG | 375 mM Mannitol | 1.5 uM ABA |
|---|---|---|---|---|
| SP10 | 32449 | 0 | 0 | 14 |
| SP11 | 32449 | 15 | 3 | 13 |
| SP12 | 32449 | 3 | 0 | 6 |
| SP13 | 32449 | 0 | 2 | 1 |

Qualitative and Quantitative Analysis of 5 Independent Events Representing 35S::cDNA 12333678 on PEG, Mannitol and ABA Seedlings that survived transfer to soil and which were Basta$^R$-resistant were subjected to PCR and sequencing. At least one resistant plant in each of the three osmotic screens contained 35S::cDNA 12333678 (ME01334). T$_2$ seeds from the 5 independent transformants that contain this clone and that were used in the pooling process were tested for Basta$^R$ resistance and for stress tolerance in the 3 surrogate drought screens.

To identify two independent events of 35S::cDNA 12333678 showing PEG, mannitol, and ABA resistance, 36 seedlings from each of four events, ME01334-01, 02, 03, and 04 were screened as previously described. Simultaneously, Basta$^R$ segregation was assessed to identify events containing a single insert segregating in a 3:1 (R:S) ratio as calculated by a Chi-square test (Table 3-2). All of the events tested segregated for a single functional insert.

TABLE 3-2

Basta$^R$ segregation for ME01334 individual events

| Event | Resistant | Sensitive | Total | Probability of Chi-test* |
|---|---|---|---|---|
| ME01334-01 | 28 | 8 | 36 | 0.70031 |
| ME01334-02 | 22 | 14 | 36 | 0.05429 |
| ME01334-03 | 31 | 5 | 36 | 0.12366 |
| ME01334-04 | 24 | 12 | 36 | 0.24821 |
| ME01334-5 | | | Insufficient seeds to test | |

*Chi-test to determine whether actual ratio of resistant to sensitive differs from the expected 3:1 ratio.

Events ME01334-01 and 04 were chosen as the two events because they had the strongest and most consistent resistance to PEG, mannitol and ABA. Resistance was observed for ME01334-02 and 03 although not in expected ratios in all three screens (data not shown). The controls were sown the same day and in the same plate as the individual events. The transgenic control in each of these plates is a segregant, from this ME line or another ME line being tested, that failed to show resistance to the particular stress. The PEG (Tables 3-3 and 3-4), mannitol (Tables 3-5 and 3-6) and ABA (Tables 3-7 and 3-8) segregation ratios observed for ME01334-01 and 01 are consistent with the presence of a single insert as demonstrated by Chi-Square. This is similar to that observed for Basta$^R$ resistance (Table 3-2).

On 18% PEG, the resistant seedlings from these two events show some root growth but they are also green with new leaves emerging at day 14. The mannitol-resistant seedlings showed more root and shoot growth than the PEG resistant seedlings. The resistant seedlings on ABA show the least amount of growth, and very little root growth relative to the mannitol and PEG screens. The phenotype of the resistant seedlings is unique on each of the screens.

TABLE 3-3

Chi-square analysis assuming a 3:1 (R:S) ratio for progeny of ME01334-01 containing 35S::cDNA 12333678 on PEG.

| Event | Observed | Expected | $\chi^2$ | Probability of Chi-Test |
|---|---|---|---|---|
| PEG Resistant | 26 | 26.25 | 0.002 | 0.922 |
| PEG Sensitive | 9 | 8.75 | 0.007 | |
| | 35 | 35 | 0.009 | |

TABLE 3-4

Chi-square analysis assuming a 3:1 (R:S) ratio for progeny of ME01334-04 containing 35S::cDNA 12333678 on PEG.

| Event | Observed | Expected | $\chi^2$ | Probability of Chi-Test |
|---|---|---|---|---|
| PEG Resistant | 27 | 27 | 0 | 1.0 |
| PEG Sensitive | 9 | 9 | 0 | |
| | 36 | 36 | 0 | |

TABLE 3-5

Chi-square analysis assuming a 3:1 (R:S) ratio for progeny of ME01334-01 containing 35S::cDNA 12333678 on mannitol.

| Event | Observed | Expected | $\chi^2$ | Probability of Chi-Test |
|---|---|---|---|---|
| Mannitol Resistant | 14 | 23.25 | 3.68 | 0.0001 |
| Mannitol Sensitive | 17 | 7.75 | 11.04 | |
| | 31 | 31 | 14.72 | |

TABLE 3-6

Chi-square analysis assuming a 3:1 (R:S) ratio for progeny of ME01334-04 containing 35S::cDNA 12333678 on mannitol.

| Event | Observed | Expected | $\chi^2$ | Probability of Chi-Test |
|---|---|---|---|---|
| Mannitol Resistant | 16 | 22.5 | 1.88 | 0.006 |
| Mannitol Sensitive | 14 | 7.5 | 5.63 | |
| | 30 | 30 | 7.51 | |

TABLE 3-7

Chi-square analysis assuming a 3:1 (R:S) ratio for progeny of ME01334-01 containing 35S::cDNA 12333678 on ABA.

| Event | Observed | Expected | $\chi^2$ | Probability of Chi-Test |
|---|---|---|---|---|
| ABA Resistant | 24 | 24 | 0 | 1.0 |
| ABA Sensitive | 8 | 8 | 0 | |
| | 32 | 32 | 0 | |

TABLE 3-8

Chi-square analysis assuming a 3:1 (R:S) ratio for progeny of ME01334-04 containing 35S::cDNA 12333678 on ABA.

| Event | Observed | Expected | $\chi^2$ | Probability of Chi-Test |
|---|---|---|---|---|
| ABA Resistant | 19 | 25.5 | 1.657 | 0.01 |
| ABA Sensitive | 15 | 8.5 | 4.97 | |
| | 34 | 34 | 6.627 | |

Qualitative and Quantitative Analysis of Progeny of $T_2$ Plants Isolated on PEG, Mannitol and ABA Progeny from $T_2$ plants that were recovered from the three screens and contained cDNA 12333678 (SP1-A2, SP1-P3, and SP1-M19) were analyzed and also found to be resistant to PEG, mannitol and ABA indicating that resistance is transmitted to the next generation. Taken together, 1) the isolation of resistant seedlings containing cDNA 12333678 from all three surrogate screens for drought, 2) the inheritance of this resistance in the next generation, and 3) the fact that the progeny from two or more events from the original transformation also segregated for resistance to these osmotic stresses, provides strong evidence that cDNA 12333678 when over-expressed provides tolerance to osmotic stress.

This gene is annotated as an alpha/beta hydrolase, a probable acetone-cyanohydrin lyase. Acetone-cyanohydrin lyase is involved in the catabolism of cyanogenic glycosides.

Figure 3:
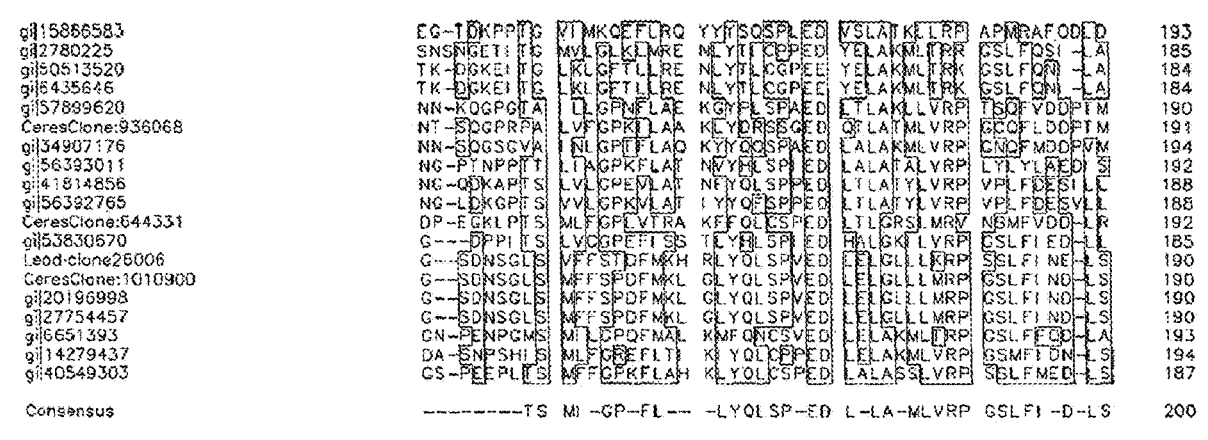

FIG. 3 provides the results of the consensus sequence (SEQ ID NOs: 130-146) analysis based on Ceres cDNA 12333678.

Example 4—Ceres cDNA 12384873

Clone 34419, Ceres cDNA 12384873, encodes a full-length strictosidine synthase. Ectopic expression of Ceres cDNA 12384873 under the control of the CaMV35S promoter induces the following phenotypes:

Germination on high concentrations of polyethylene glycol (PEG), mannitol, and abscissic acid (ABA).

Continued growth on high PEG, mannitol, and ABA.

Generation and Phenotypic Evaluation of $T_1$ Lines Containing 35S::cDNA 12384873

Wild-type *Arabidopsis* Wassilewskija (WS) plants were transformed with a $T_i$ plasmid containing cDNA 12384873 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol, and ABA as Surrogate Screens for Drought Tolerance.

Seeds from 13 superpools (1,200 $T_2$ seeds from each superpool) from the CaMV35S or 32449 over-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 12384873 was identified in resistant plants from each of the three surrogate drought screens, the five individual $T_2$ events containing this cDNA (ME01490) were screened on high PEG, mannitol and ABA to identify events with the resistance phenotype.

Superpools (SP) are referred to as SP1, SP2 and so on. The letter following the hyphen refers to the screen (P=PEG, M=mannitol and A=ABA) and the number following the letter refers to a number assigned to each plant obtained from that screen on that superpool. For example, SP1-M18 is the 18$^{th}$ plant isolated from a mannitol screen of Superpool 1.

Qualitative Analysis of 13 Superpools on PEG, Mannitol, and ABA.

Resistant candidates were selected based on increased size when compared to the largest wild-type control seedlings. All three screens resulted in a decrease in germination for both wildtype and superpools as compared to seeds on control media. Wild-type seeds that germinated on any of the screens were small and never developed any first leaves even after 40 days. To ensure that even slightly tolerant individuals were not omitted, seedlings that showed any growth and greening whatsoever were recovered and transferred to soil for assessment in the $T_3$ generation. All recovered candidates showed signs of vigorous re-growth on soil, although the development was slightly delayed as compared to unstressed plants, presumably because of the transient exposure to stress. The plants transferred to soil were sprayed with Basta$^R$ to eliminate any false-positives, or any lines where the Basta$^R$ marker was suppressed. All of the Basta$^R$-resistant candidates flowered and set seed. Resistant seedlings were recovered from Superpools 1, 7 and 11 on all screens (Table 4-1).

TABLE 4-1

Number of stress-tolerant and Basta$^R$ seedlings identified on drought surrogate screens.

| Superpool | Promoter | 18% PEG | 375 mM Mannitol | 1.5 uM ABA |
|---|---|---|---|---|
| SP1 | 35S | 10 | 13 | 11 |
| SP2 | 35S | 0 | 6 | 5 |
| SP3 | 35S | 0 | 2 | 10 |
| SP4 | 35S | 0 | 4 | 0 |
| SP5 | 35S | 0 | 0 | 5 |
| SP6 | 35S | 0 | 0 | 4 |
| SP7 | 35S | 1 | 4 | 8 |
| SP8 | 35S | 0 | 4 | 1 |
| SP9 | 32449 | 0 | 0 | 12 |
| SP10 | 32449 | 0 | 0 | 14 |
| SP11 | 32449 | 15 | 3 | 13 |
| SP12 | 32449 | 3 | 0 | 6 |
| SP13 | 32449 | 0 | 2 | 1 |

Qualitative and Quantitative Analysis of 5 Independent Events Representing 35S::cDNA 12384873 on PEG, Mannitol and ABA Seedlings that survived transfer to soil and which were Basta$^R$-resistant were subjected to PCR and sequencing. At least one resistant plant in each of the three osmotic screens contained 35S::cDNA 12384873 (ME01490 g. $T_2$ seeds from the 5 independent transformants that contain this clone and that were used in the pooling process were tested for Basta$^R$ resistance and for stress tolerance in the 3 surrogate drought screens.

To identify two independent events of 35S::cDNA 12384873 showing PEG, mannitol and ABA resistance, 36 seedlings from each of five events, ME01490-01, 02, 03, 04, and 05 were screened as previously described. Simultaneously, Basta$^R$ segregation was assessed to identify events containing a single insert segregating in a 3:1 (R:S) ratio as calculated by a Chi-square test (Table 4-2). Three of the events segregated for a single functional insert (-01, -02 and -04). For the other two events one segregated for two independent inserts (-03) and one segregated for a deficiency of Basta$^R$ seedlings (-05).

TABLE 4-2

Basta$^R$ segregation for ME01490 individual events

| Event | Resistant | Sensitive | Total | Probability of Chi-test* |
|---|---|---|---|---|
| ME01490-01* | 24 | 12 | 36 | 0.24821 |
| ME01490-02* | 26 | 10 | 36 | 0.70031 |
| ME01490-03 | 35 | 1 | 36 | 0.00208** |
| ME01490-04 | 28 | 8 | 36 | 0.70031 |
| ME01490-05 | 21 | 15 | 36 | 0.02092** |

*Chi-test to determine whether actual ratio of resistant to sensitive differs from the expected 3:1 ratio.
**Significantly different than a 3:1 (R:S) ratio Events ME01490-01 and -02 were chosen as the two events because they had the strongest and most consistent resistance to PEG, mannitol and ABA. Resistance was observed for ME01490-03, -04, and -05 although not in expected ratios in all three screens (data not shown). The controls were sown the same day and in the same plate as the individual lines. The transgenic control in each of these plates is a segregant, from this ME line or another ME line being tested, that failed to show resistance to the particular stress. The PEG (Tables 4-3 and 4-4), mannitol (Tables 4-5 and 4-6) and ABA (Tables 4-7 and 4-8) segregation ratios observed for ME01490-01 and -02 are consistent with the presence of single insert, as demonstrated by Chi-square. This result is similar to that observed for Basta$^R$ resistance (Table 4-2).

TABLE 4-3

Chi-square analysis assuming a 3:1 (R:S) ratio for progeny of ME01490-01 containing 35S::cDNA 12384873 on PEG.

| Event | Observed | Expected | $\chi^2$ | Probability of Chi-Test |
|---|---|---|---|---|
| PEG Resistant | 29 | 27 | 0.148 | 0.441 |
| PEG Sensitive | 7 | 9 | 0.444 | |
| | 36 | 36 | 0.592 | |

TABLE 4-4

Chi-square analysis assuming a 3:1 (R:S) ratio for progeny of ME01490-02 containing 35S::cDNA 12384873 on PEG.

| Event | Observed | Expected | $\chi^2$ | Probability of Chi-Test |
|---|---|---|---|---|
| PEG Resistant | 24 | 24.75 | 0.0227 | 0.763 |
| PEG Sensitive | 9 | 8.25 | 0.068 | |
| | 33 | 33 | 0.0907 | |

TABLE 4-5

Chi-square analysis assuming a 3:1 (R:S) ratio for progeny of ME01490-01 containing 35S::cDNA 12384873 on mannitol.

| Event | Observed | Expected | $\chi^2$ | Probability of Chi-Test |
|---|---|---|---|---|
| Mannitol Resistant | 22 | 26.25 | 0.688 | 0.097 |
| Mannitol Sensitive | 13 | 8.75 | 2.06 | |
| | 35 | 35 | 2.748 | |

TABLE 4-6

Chi-square analysis assuming a 3:1 (R:S) ratio for progeny of ME01490-02 containing 35S::cDNA 12384873 on mannitol.

| Event | Observed | Expected | $\chi^2$ | Probability of Chi-Test |
|---|---|---|---|---|
| Mannitol Resistant | 20 | 23.25 | 0.454 | 0.178 |
| Mannitol Sensitive | 11 | 7.75 | 1.363 | |
| | 31 | 31 | 1.817 | |

TABLE 4-7

Chi-square analysis assuming a 3:1 (R:S) ratio for progeny of ME01490-01 containing 35S::cDNA 12384873 on ABA.

| Event | Observed | Expected | $\chi^2$ | Probability of Chi-Test |
|---|---|---|---|---|
| ABA Resistant | 28 | 27 | 0.037 | 0.7 |
| ABA Sensitive | 8 | 9 | 0.148 | |
| | 36 | 36 | 1.85 | |

TABLE 4-8

Chi-square analysis assuming a 3:1 (R:S) ratio for progeny of ME01490-02 containing 35S::cDNA 12384873 on ABA.

| Event | Observed | Expected | $\chi^2$ | Probability of Chi-Test |
|---|---|---|---|---|
| ABA Resistant | 23 | 27 | 0.593 | 0.124 |
| ABA Sensitive | 13 | 9 | 1.78 | |
| | 36 | 36 | 2.373 | |

Qualitative and Quantitative Analysis of Progeny of $T_2$ Plants Isolated on PEG, Mannitol and ABA Progeny of the $T_2$ plants that were recovered from the three screens and contained cDNA 12384873 (SP1-A18, SP1-P14, SP1-M5, SP1-M6 and SP1-M7) were analyzed and also found to be resistant to PEG, mannitol and ABA indicating that resistance is transmitted to the next generation. Taken together, 1) the isolation of resistant seedlings containing cDNA 12384873 from all three surrogate screens for drought, 2) the inheritance of this resistance in the next generation, and 3) the fact that the progeny from two or more events from the original transformation also segregated for resistance to these osmotic stresses, provides strong evidence that cDNA 12384873 when over-expressed can provide tolerance to osmotic stress.

Clone 34419 encodes the first 29 amino acids of a strictosidine synthase protein, and then a frame shift results in a novel stretch of 63 amino acids on the 3' end of the protein.

Example 5—Ceres cDNA 12659859

Ceres cDNA 12659859 encodes a FAD-linked oxidoreductase family, a probable berberine bridge enzyme from *Arabidopsis thaliana*. Ectopic expression of Ceres cDNA 12659859 under the control of the CaMV35S promoter induces the following phenotypes:

Germination on high concentrations of polyethylene glycol (PEG), mannitol and abscissic acid (ABA).

Continued growth on high concentration of PEG, mannitol and ABA.

Generation and Phenotypic Evaluation of $T_1$ Lines Containing 35S::cDNA 12659859.

Wild-type *Arabidopsis* Wassilewskija (WS) plants were transformed with a Ti plasmid containing cDNA 12659859 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol, and ABA as Surrogate Screens for Drought Tolerance.

Seeds from 13 superpools (1,200 $T_2$ seeds from each superpool) from the CaMV35S or 32449 over-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 12659859 was identified in resistant plants from each of the three surrogate drought screens, the five individual $T_2$ events containing this cDNA (SR01010) were screened on high PEG, mannitol, and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the 18$^{th}$ plant isolated from a mannitol screen of Superpool 1.

Qualitative and Quantitative Analysis of 2 Independent Events Representing 35S::cDNA 12659859 (SR01010) on PEG, Mannitol and ABA To identify two independent events of 35S::cDNA 12659859 showing PEG, mannitol, and ABA resistance, 36 seedlings from each of three events, SR01010-01, 02, and 03 were screened as previously described. Basta$^R$ segregation was assessed to identify lines containing a single insert segregating in a 3:1 (R:S) ratio as calculated by a Chi-square test (Table 5-1). Two of three $T_2$ generation events (01 and 03) segregated for a single insert although the segregation ratio for -01 is also not different than a 15:1 (R:S) ratio.

TABLE 5-1

Basta$^R$ segregation for SR01010 individual events

| Event | Resistant | Sensitive | Total | Probability of Chi-test* |
|---|---|---|---|---|
| SR01010-01 | 32 | 4 | 36 | 0.05429 |
| SR01010-02 | 32 | 3 | 35 | 0.0248** |
| SR01010-03 | 24 | 12 | 36 | 0.24821 |
| SR01010-01-1 | 27 | 9 | 36 | 1 |
| SR01010-03-1 | 20 | 13 | 33 | 0.05619 |

*Chi-test to determine whether actual ratio of resistant to sensitive differs from the expected 3:1 ratio.
**Significantly different than a 3:1 (R:S) ratio Lines SR0101-01 and -03 were chosen as the two events because they had a strong and consistent resistance to PEG, mannitol and ABA. Resistance was observed for SR01010-02 although not in expected ratios in all three screens (data not shown). The controls were sown the same day and in the same plate as the individual lines. The PEG (Tables 5-2 and 5-3), mannitol (Tables 5-4 and 5-5) and ABA (Tables 5-6 and 5-7) segregation ratios observed for SR01010-01 and -03 are consistent with the presence of single insert as demonstrated by chi-square, similar to what we observed for Basta$^R$ resistance (Table 5-1).

The progeny from one resistant $T_2$ plant from each of these two events was tested in the $T_3$ generation in the same manner. Resistance to PEG, mannitol and ABA was also observed in the $T_3$ generation. Taken together, the segregation of resistant seedlings containing cDNA 12659859 from two events on all three drought surrogate screens and the inheritance of this resistance in a subsequent generation, provide strong evidence that cDNA 12659859 when overexpressed can provide tolerance to drought.

TABLE 5-2

Chi-square analysis assuming a 3:1 (R:S) ratio for progeny of SR01010-01T$_2$ containing 35S::cDNA 12659859 on PEG.

| Event | Observed | Expected | $\chi^2$ | Probability |
|---|---|---|---|---|
| PEG Resistant | 31 | 26.25 | .860 | .064 |
| PEG Sensitive | 4 | 8.75 | 2.579 | |
| | 35 | 35 | 3.438 | |

TABLE 5-3

Chi-square analysis assuming a 3:1 (R:S) ratio for progeny of SR01010-03 T$_2$ containing 35S::cDNA 12659859 on PEG.

| Event | Observed | Expected | $\chi^2$ | Probability |
|---|---|---|---|---|
| PEG Resistant | 28 | 27 | .037 | .700 |
| PEG Sensitive | 8 | 9 | .111 | |
| | 36 | 36 | .148 | |

TABLE 5-4

Chi-square analysis assuming a 3:1 (R:S) ratio for progeny of SR01010-01T$_2$ containing 35S::cDNA 12659859 on mannitol.

| Event | Observed | Expected | $\chi^2$ | Probability |
|---|---|---|---|---|
| Mannitol Resistant | 25 | 27 | .148 | .441 |
| Mannitol Sensitive | 11 | 9 | .444 | |
| | 36 | 36 | .593 | |

TABLE 5-5

Chi-square analysis assuming a 3:1 (R:S) ratio for progeny of SR01010-3 $T_2$ containing 35S::cDNA 12659859 on mannitol.

| Event | Observed | Expected | $\chi^2$ | Probability |
|---|---|---|---|---|
| Mannitol Resistant | 21 | 20.25 | .028 | .739 |
| Mannitol Sensitive | 6 | 6.75 | .083 | |
| | 27 | 27 | .111 | |

TABLE 5-6

Chi-square analysis assuming a 3:1 (R:S) ratio for progeny of SR01010-01$T_2$ containing 35S::cDNA 12659859 on ABA.

| Event | Observed | Expected | $\chi^2$ | Probability |
|---|---|---|---|---|
| ABA Resistant | 30 | 27 | .333 | .248 |
| ABA Sensitive | 6 | 9 | 1 | |
| | 36 | 36 | 1.333 | |

TABLE 5-7

Chi-square analysis assuming a 3:1 (R:S) ratio for progeny of SR01010-03 $T_2$ containing 35S::cDNA 12659859 on ABA.

| Event | Observed | Expected | $\chi^2$ | Probability |
|---|---|---|---|---|
| ABA Resistant | 27 | 27 | 0 | 1.0 |
| ABA Sensitive | 9 | 9 | 0 | |
| | 36 | 36 | 0 | |

Figure 4:
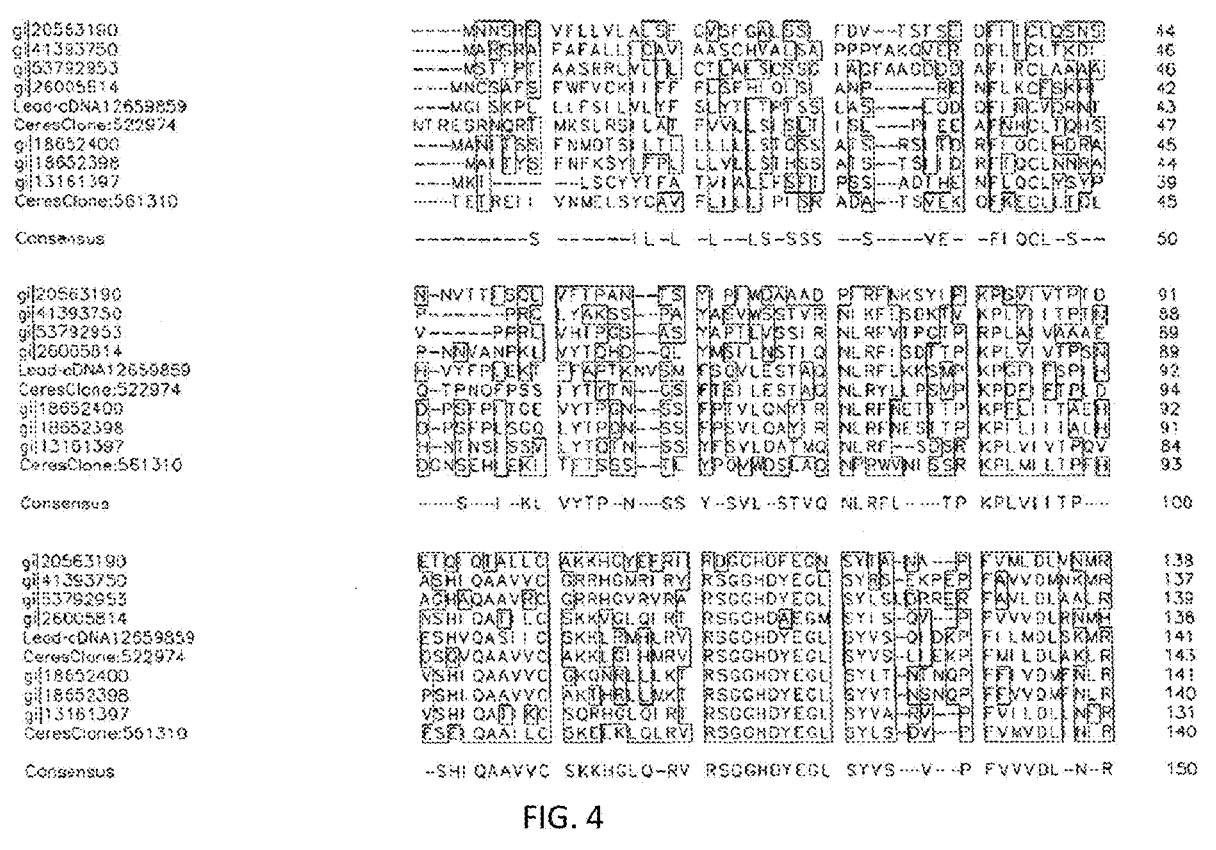
Figure 4:
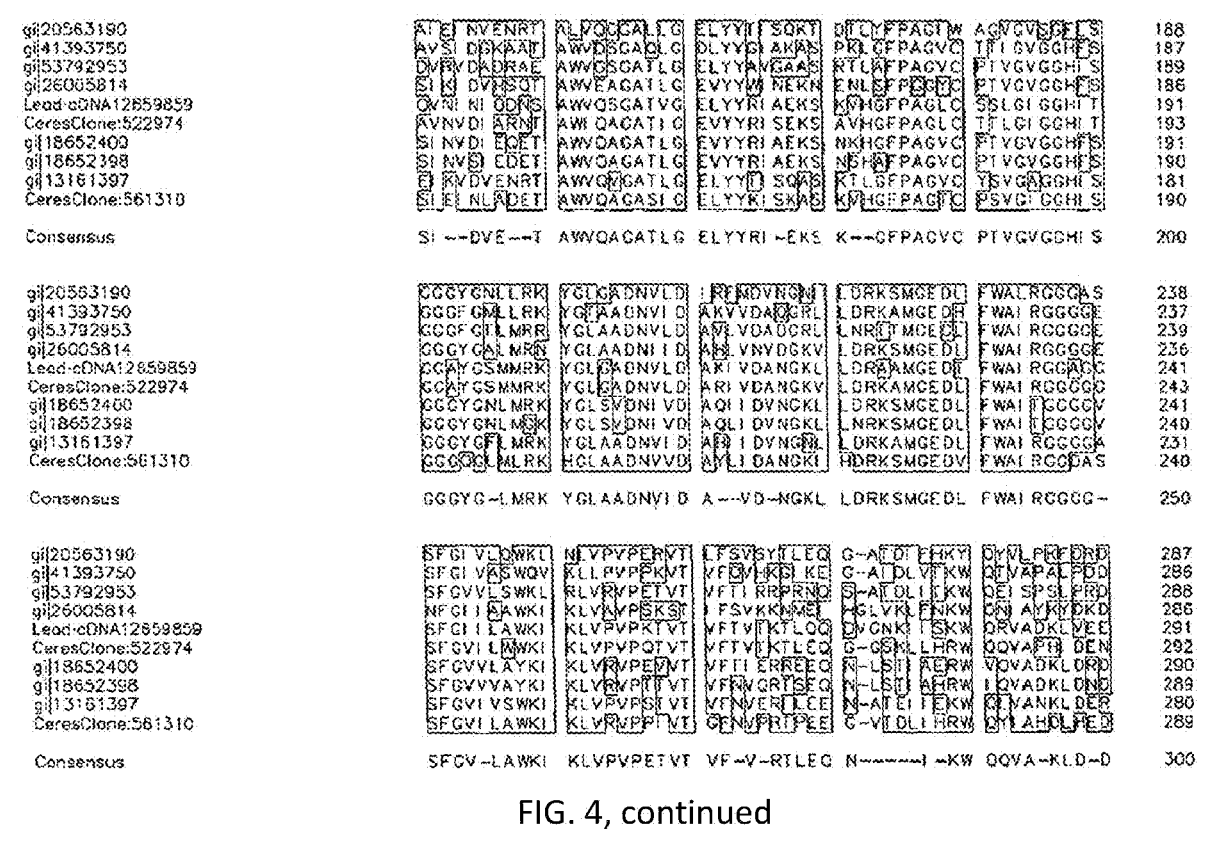
Figure 4:
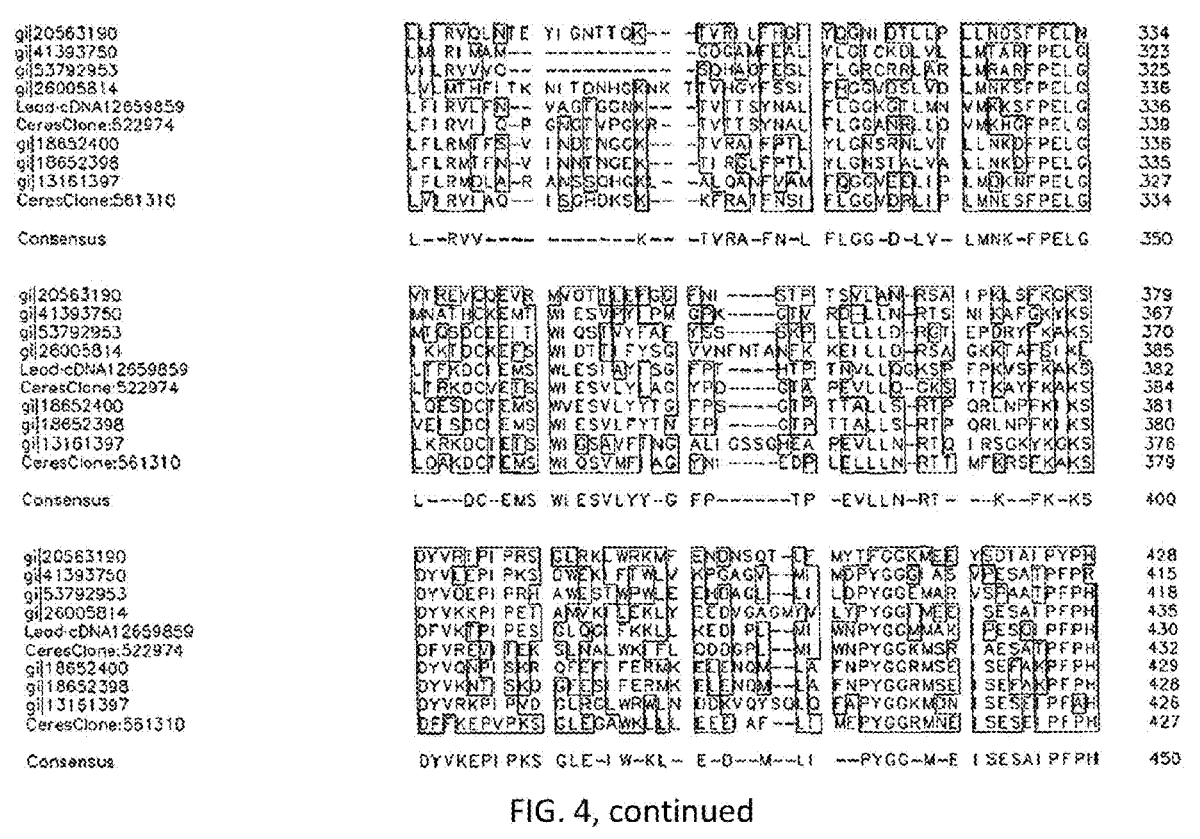
Figure 4:
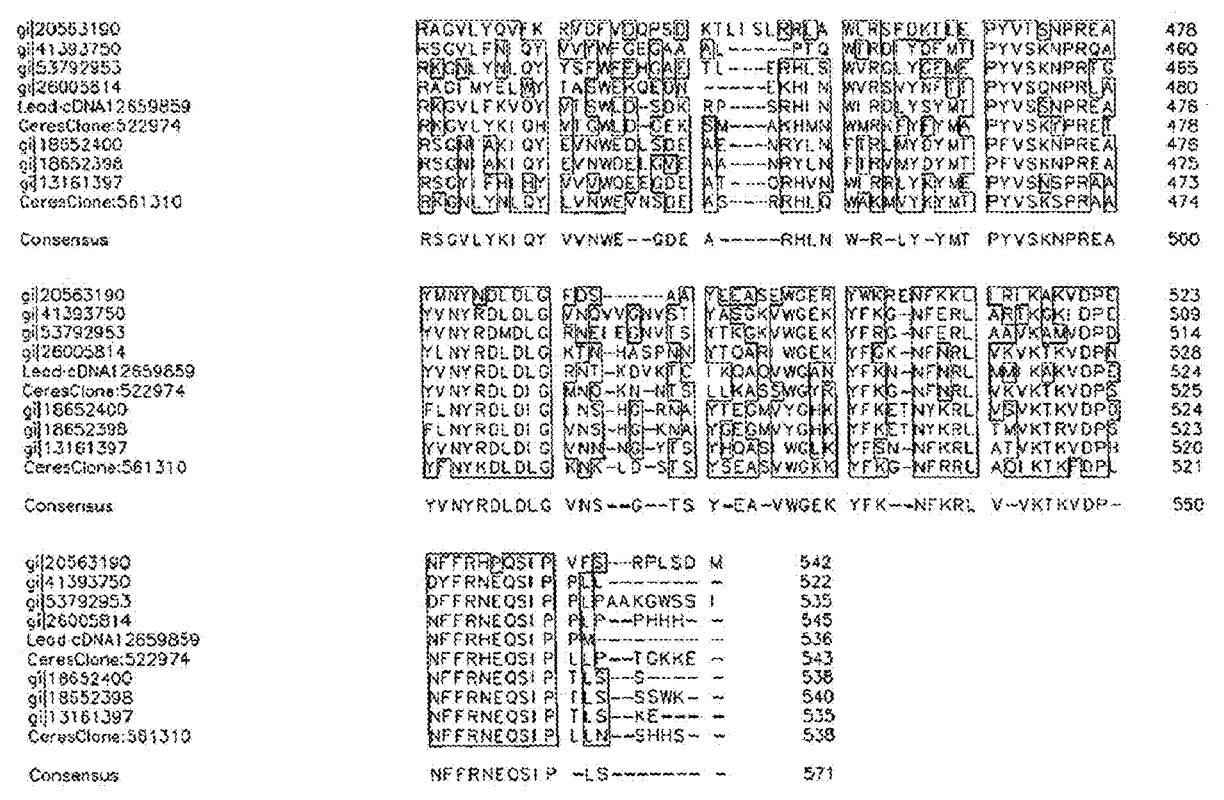

FIG. 4 provides the results of the consensus sequence (SEQ ID NOs: 147-177) analysis based on Ceres cDNA 12659859

Example 6—Ceres cDNA 12723147

Ceres cDNA 12723147 encodes an *Arabidopsis* putative aldo/keto reductase. Ectopic expression of Ceres cDNA 12723147 under the control of the CaMV35S promoter induces the following phenotypes:

Germination on high concentrations of polyethylene glycol (PEG), mannitol and abscissic acid (ABA).
Continued growth on high concentration of PEG, mannitol and ABA.

Generation and Phenotypic Evaluation of $T_1$ Lines Containing 35S::cDNA 12723147.

Wild-type *Arabidopsis* Wassilewskija (WS) plants were transformed with a Ti plasmid containing cDNA 12723147 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol, and ABA as Surrogate Screens for Drought Tolerance.

Seeds from 13 superpools (1,200 $T_2$ seeds from each superpool) from the CaMV35S or 32449 over-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 12723147 was identified in resistant plants from each of the three surrogate drought screens, the five individual $T_2$ events containing this cDNA (SR01013) were screened on high PEG, mannitol, and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the 18th plant isolated from a mannitol screen of Superpool 1.

Qualitative and Quantitative Analysis of 2 Independent Events Representing 35S::cDNA 12659859 (SR01010) on PEG, Mannitol and ABA To identify two independent events of 35S::cDNA 12659859 showing PEG, mannitol, and ABA resistance, 36 seedlings from each of two events, SR01013-01 and -02 were screened as previously described. Basta[R] segregation was assessed to verify that the lines contained a single insert segregating in a 3:1 (R:S) ratio as calculated by a chi-square test (Table 6-1). Both lines (01 and 02) segregated for a single insert in the $T_2$ generation (Table 1)

TABLE 6-1

| Basta[R] segregation for SR01013 individual events | | | | |
|---|---|---|---|---|
| Event | Resistant | Sensitive | Total | Probability of Chi-test* |
| SR01013-01 | 30 | 5 | 35 | 0.14323 |
| SR01013-02 | 30 | 6 | 36 | 0.24821 |
| SR01013-01-3 | 34 | 1 | 36 | 0.00248** |
| SR01013-02-2 | 32 | 0 | 32 | 0.00109** |

*Chi-test to determine whether actual ratio of resistant to sensitive differs from the expected 3:1 ratio.
**Significantly different than a 3:1 (R:S) ratio Lines SR01013-01 and -02 were chosen as the two events because they had a strong and consistent resistance to PEG, mannitol and ABA. The controls were sown the same day and in the same plate as the individual lines. The PEG (Tables 6-2 and 6-3), mannitol (Tables 6-4 and 6-5) and ABA (Tables 6-6 and 6-7) segregation ratios observed for SR01013-01 and -02 are consistent with the presence of single insert as demonstrated by chi-square, similar to what we observed for Basta[R] resistance (Table 6-1).

The progeny from one resistant $T_2$ plant from each of these two events were tested in the same manner as the $T_2$. Resistance to PEG, mannitol and ABA was also observed in the $T_3$ generation. Taken together, the segregation of resistant seedlings containing cDNA 12723147 from two events on all three drought surrogate screens and the inheritance of this resistance in a subsequent generation, provide strong evidence that cDNA 12723147 when over-expressed can provide tolerance to drought.

TABLE 6-2

Chi-square analysis assuming a 3:1 (R:S) ratio for progeny of SR01013-01$T_2$ containing 35S::cDNA 12723147 on PEG.

| Event | Observed | Expected | $\chi^2$ | Probability of Chi-Test |
|---|---|---|---|---|
| PEG Resistant | 22 | 27 | 0.926 | 0.054 |
| PEG Sensitive | 14 | 9 | 2.778 | |
| | 36 | 36 | 3.704 | |

TABLE 6-3

Chi-square analysis assuming a 3:1 (R:S) ratio for progeny of SR01013-02 $T_2$ containing 35S::cDNA 12723147 on PEG.

| Event | Observed | Expected | $\chi^2$ | Probability of Chi-Test |
|---|---|---|---|---|
| PEG Resistant | 26 | 27 | 0.037 | .700 |
| PEG Sensitive | 10 | 9 | .111 | |
| | 36 | 36 | .148 | |

TABLE 6-4

Chi-square analysis assuming a 3:1 (R:S) ratio for progeny of SR01013-01 $T_2$ containing 35S::cDNA 12723147 on mannitol.

| Event | Observed | Expected | $\chi^2$ | Probability of Chi-Test |
|---|---|---|---|---|
| Mannitol Resistant | 28 | 27 | .037 | .700 |
| Mannitol Sensitive | 8 | 9 | .111 | |
| | 36 | 36 | .148 | |

TABLE 6-5

Chi-square analysis assuming a 3:1 (R:S) ratio for progeny of SR01013-02 $T_2$ containing 35S::cDNA 12723147 on mannitol.

| Event | Observed | Expected | $\chi^2$ | Probability of Chi-Test |
|---|---|---|---|---|
| Mannitol Resistant | 18 | 27 | 3 | .0005 |
| Mannitol Sensitive | 18 | 9 | 9 | |
| | 36 | 36 | 12 | |

TABLE 6-6

Chi-square analysis assuming a 3:1 (R:S) ratio for progeny of SR01013-02 $T_2$ containing 35S::cDNA 12723147 on ABA.

| Event | Observed | Expected | $\chi^2$ | Probability |
|---|---|---|---|---|
| ABA Resistant | 13 | 24 | 5.042 | 7.098 |
| ABA Sensitive | 19 | 8 | 15.125 | |
| | 32 | 32 | 20.167 | |

TABLE 6-7

Chi-square analysis assuming a 3:1 (R:S) ratio for progeny of SR01013-02 $T_2$ containing 35S::cDNA 12723147 on ABA.

| Event | Observed | Expected | $\chi^2$ | Probability |
|---|---|---|---|---|
| ABA Resistant | 13 | 24 | 5.042 | 7.098 |
| ABA Sensitive | 19 | 8 | 15.125 | |
| | 32 | 32 | 20.167 | |

Figure 5:
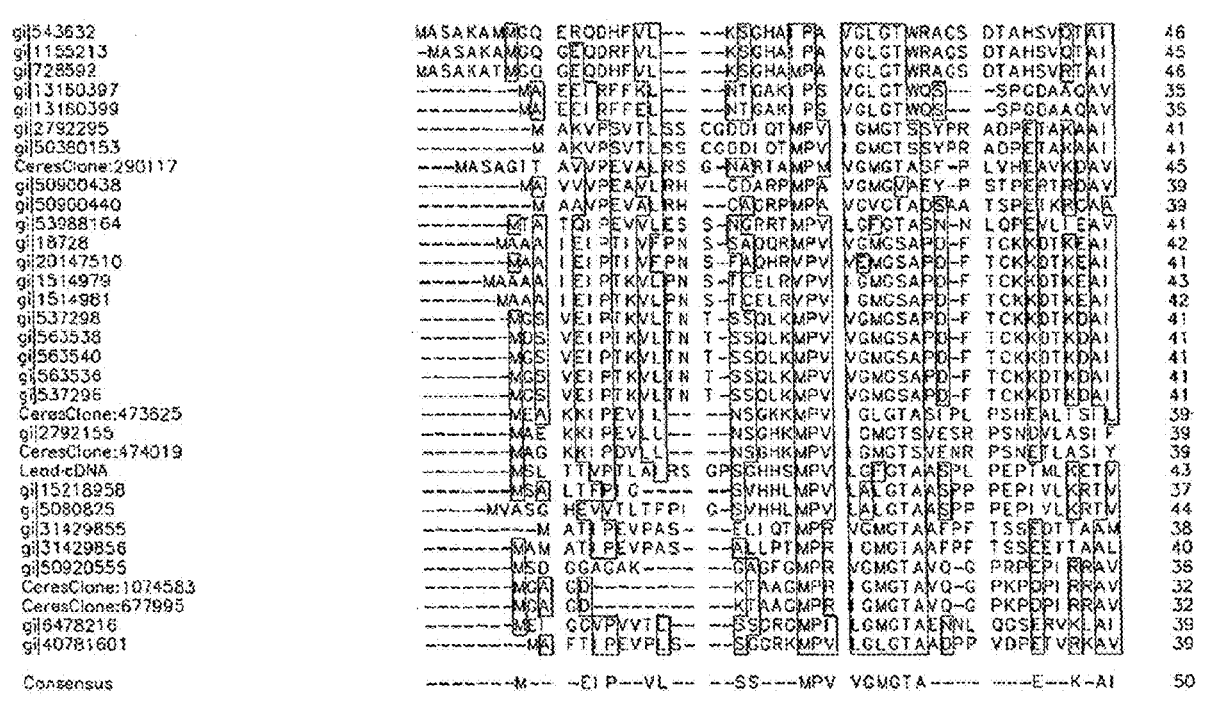
Figure 5:
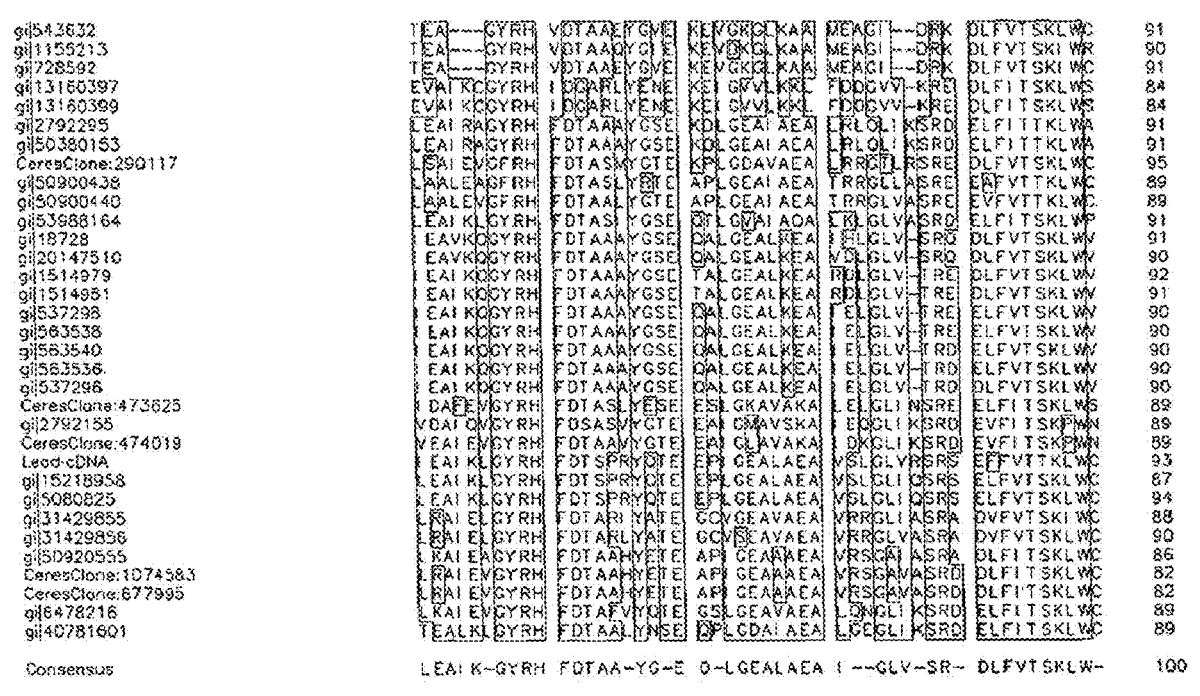
Figure 5:
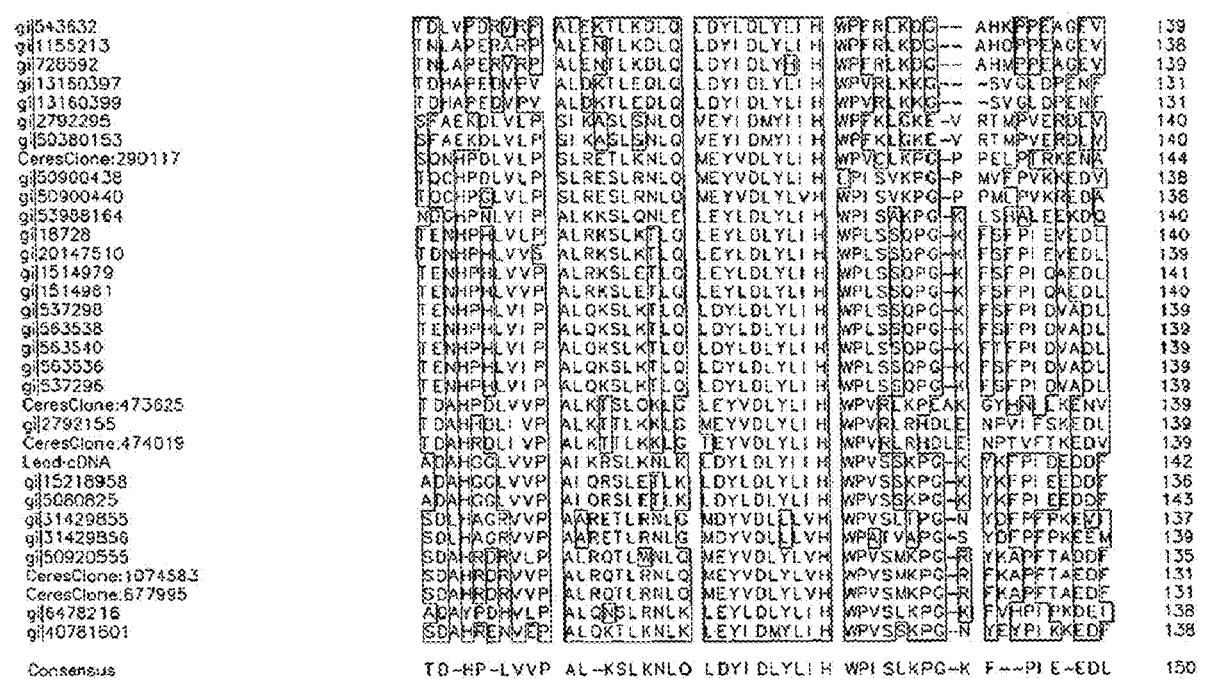
Figure 5:
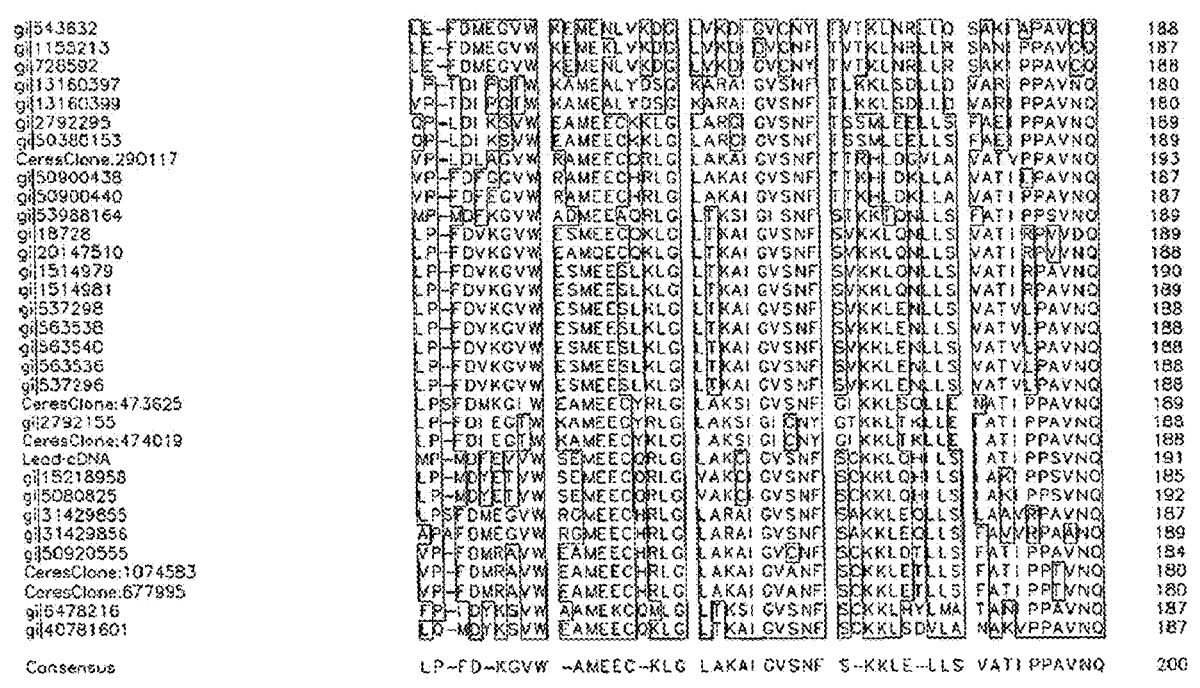
Figure 5:
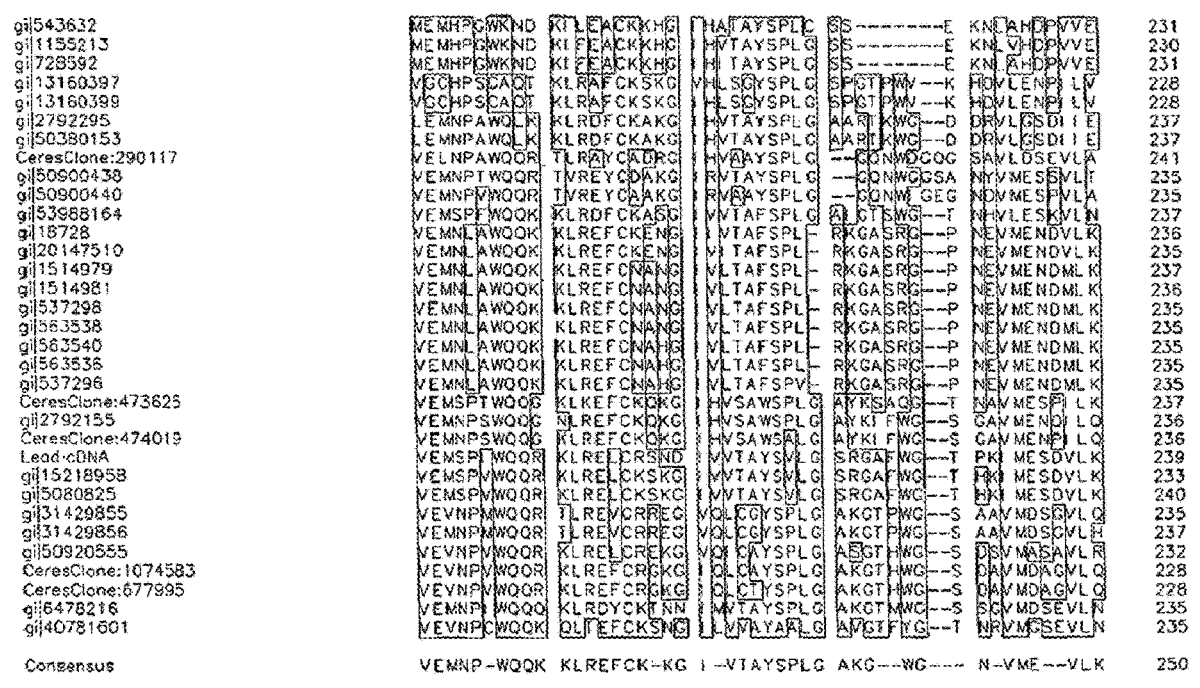
Figure 5:
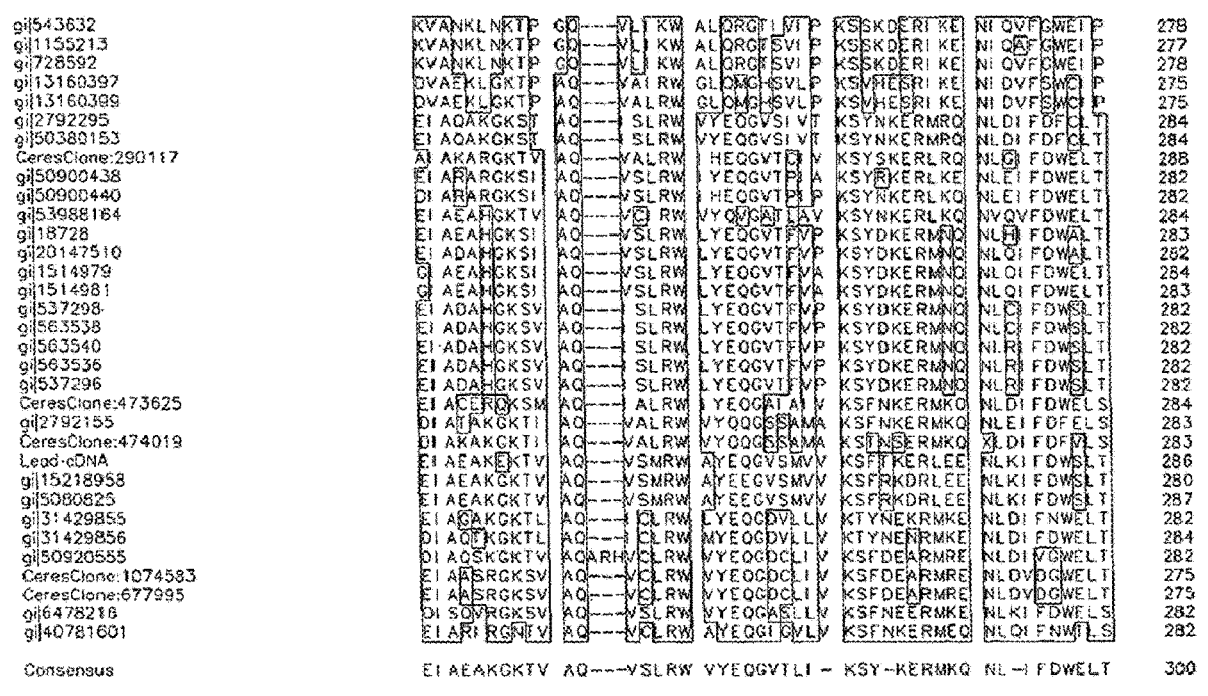
Figure 5:
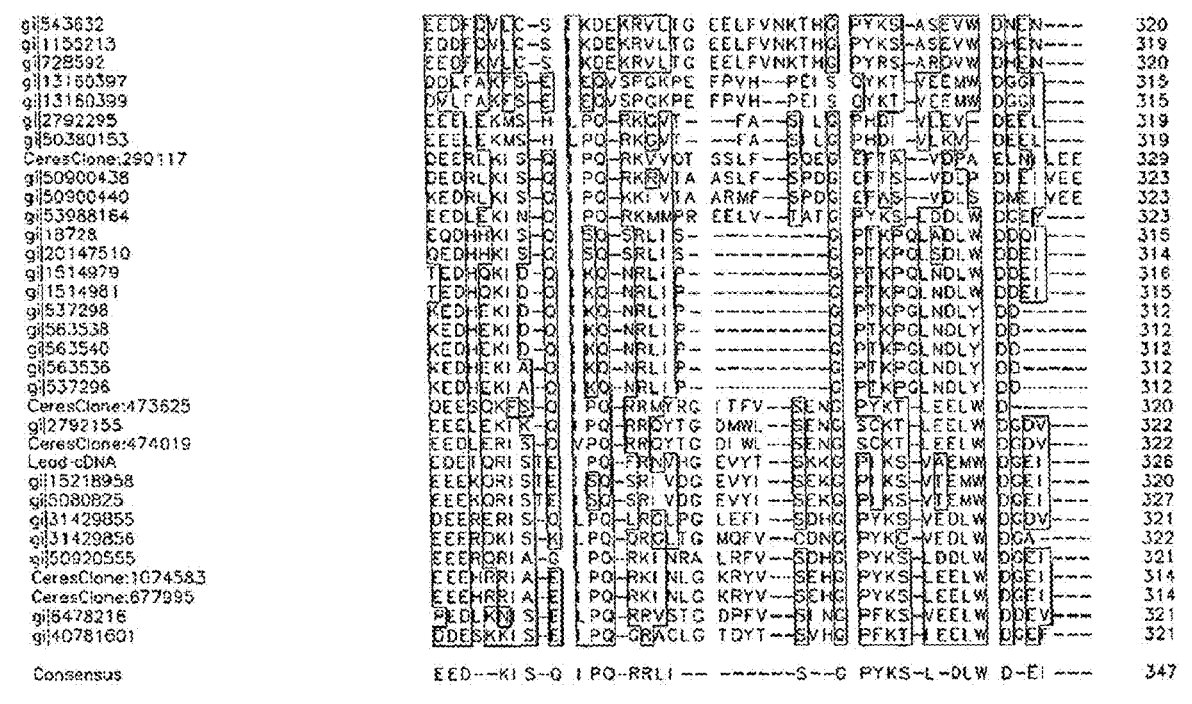

FIG. 5 provides the results of the consensus sequence (SEQ ID NOs: 178-200) analysis based on Ceres cDNA 12723147.

Example 7—Ceres cDNA 13488750

Clone 125039, Ceres cDNA 13488750, encodes a full-length putative adenylylsulfate (APS) kinase from *Arabidopsis thaliana*. Ectopic expression of Ceres cDNA 13488750 under the control of the CaMV35S promoter induces the following phenotypes:

Continued growth under high heat conditions.

Generation and Phenotypic Evaluation of $T_1$ Lines Containing 35S::cDNA 13488750.

Wild-type *Arabidopsis* Wassilewskija (WS) plants were transformed with a Ti plasmid containing cDNA 13488750 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No negative phenotypes were observed in the $T_1$ plants although three of the T1 lines produced a small rosette (ME02526-01, 02 and 05). $T_2$ and $T_3$ lines of events ME02526-01 and ME02526-05 did not show the small rosette phenotype.

Screens of Masterpools for Heat Tolerance Via Heat Shock In Vitro.

Seeds from 100 masterpools from the CaMV35S or 32449 over-expression lines were tested for heat tolerance in vitro as described above.

Once cDNA 13488750 was identified in tolerant plants from the screen, five individual $T_2$ events containing this cDNA (ME02526) were screened on soil as described above to identify events with the resistance phenotype.

Qualitative Analysis of the $T_2$ Masterpool of cDNA 13488750 Plants Heat Shocked on Plates Visual phenotyping of the masterpool containing cDNA 13488750 (ME02526) on agar or soil showed no visible alterations in phenotype (data not shown). After heat-shock at 15 days of age, the ME02526 masterpool showed greater heat recovery as compared to the wild-type control and other transgenic masterpools. Assessment was a measure of "greenness" as well as continued growth at 23° C. after heat shock at 45° C. for between 5 and 8 hours. Immediately after the heat shock stress, the extent of stress-induced damage in the control and ME02526 masterpool appeared comparable. The leaves and cotyledons were wilted and droopy although still green. However, after 4 days of recovery, 2 of 10 plants in the ME02526 masterpool had completely recovered and were growing again. Other seedlings showed some recovery as measured by greenness compared to the wild-type control.

Qualitative and Quantitative Analysis of Individual $T_2$ Events of cDNA 13488750 Under Continual Heat Treatment on Soil Five independent events of ME02526 were tested on soil as described above. Two of the events (ME02526-04 and -05) showed heat resistance after continual growth at 36° C. Heat resistance was noted as decreased chlorosis compared to wild-type. Segregation frequencies of the transgene under test suggest that these two events contain a single insert, as calculated by a chi-square test (Tables 7-1, 7-2 and 7-3). Ten and 11 plants from events 04 and 05, respectively, showed continued vigor and decreased chlorosis after continuous heat treatment compared to wild-type controls.

TABLE 7-1

Chi-square analysis assuming a 3:1 (R:S) ratio for progeny of ME02526-04 and -05 containing 35S::cDNA 13488750 on Finale.

| Event | Observed | Expected | $\chi^2$ | Probability of Chi-Test |
|---|---|---|---|---|
| ME02526-04 Finale Resistant | 29 | 27 | 0.593 | 0.44 |
| ME02526-04 Finale Sensitive | 7 | 9 | | |
| | 36 | 36 | | |
| ME02526-05 Finale Resistant | 27 | 27 | 0 | 1 |
| ME02526-05 Finale Sensitive | 9 | 9 | | |
| | 36 | 36 | | |

TABLE 7-2

Chi-square analysis assuming a 3:1 (R:S) ratio for progeny of ME02526-04 containing 35S::cDNA 13488750 for thermo tolerance (continual growth at 36° C. on soil).

| Event | Observed | Expected | $\chi^2$ | Probability of Chi-Test |
|---|---|---|---|---|
| Heat Tolerant | 10 | 11.25 | 0.556 | 0.456 |
| Heat Sensitive | 5 | 3.75 | | |
| | 15 | 15 | | |

TABLE 7-3

Chi-square analysis assuming a 3:1 (R:S) ratio for progeny of ME02526-05 containing 35S::cDNA 13488750 for thermo tolerance (continual growth at 36° C. on soil).

| Event | Observed | Expected | $\chi^2$ | Probability of Chi-Test |
|---|---|---|---|---|
| Heat Tolerant | 11 | 11.25 | 0.022 | 0.881 |
| Heat Sensitive | 4 | 3.75 | | |
| | 15 | 15 | | |

The plants that survive the heat treatment show premature bolting and reduced fecundity but much less so than the control plants. Control and ME02526 plants bolt after only 4 days of exposure to 36° C. (11-day old plants), but were more vigorous and less chlorotic than the controls and the height and branch number was comparable to those of wild-type (data not shown). Heat-tolerant lines all showed seed abortion and reduced fecundity (data not shown). Seed abortion and reduced silique size was also prevalent in all wild-type controls (data not shown). Events 04 and 05, which had a thermo tolerant phenotype in the $T_2$ generation, were evaluated in greater detail in the $T_3$ generation for heat resistance and fecundity after prolonged heat stress on MS plates.

Qualitative and Quantitative Analysis of Individual $T_3$ Events Under 36° C. Heat Treatment on Plates Seeds from five individuals of the $T_3$ generation for ME02526-04 and -05 lines and controls were sterilized, stratified and germinated for 7 days at 23° C. prior to exposure to 36° C. heat stress. The events were evaluated for heat resistance to prolonged heat stress.

The thermo tolerant phenotype became apparent after 15 days of 36° C. treatment. $T_3$ progeny from ME02526-04 (Table 7-4) and ME02526-05 (Table 7-5) were found to segregate in the expected 3:1 ratio for the thermo tolerant phenotype.

TABLE 7-4

Chi-square analysis assuming a 3:1 (R:S) ratio for progeny of ME02526-04 containing 35S::cDNA 13488750 for thermo tolerance (continual growth at 36° C.

| Event | Observed | Expected | $\chi^2$ | Probability of Chi-Test |
|---|---|---|---|---|
| Heat Tolerant | 14 | 14.25 | 0.017 | 0.89 |
| Heat Sensitive | 5 | 4.75 | | |
| | 19 | 19 | | |

TABLE 7-5

Chi-square analysis assuming a 3:1 (R:S) ratio for progeny of ME02526-05 containing 35S::cDNA 13488750 for thermo tolerance (continual growth at 36° C.

| Event | Observed | Expected | $\chi^2$ | Probability of Chi-Test |
|---|---|---|---|---|
| Heat Tolerant | 15 | 14.25 | 0.157 | 0.69 |
| Heat Sensitive | 4 | 4.75 | | |
| | 19 | 19 | | |

Qualitative Analysis of Individual $T_3$ Events Heat Shocked on Plates for Differentiation of Natural Acquired Thermotolerance Plants acquire thermotolerance to lethal high temperatures such as 45° C. if previously exposed to moderately high temperature or if the temperature is raised gradually to an otherwise lethal temperature (Vierling, 1991). To ascertain whether the thermotolerance observed in the $T_3$ generation is due to some naturally acquired thermotolerance imparted by heat exposure of the $T_2$ parent plant (ME2526-04 and 05), thermotolerance was assessed by comparing pre-heat treated wild-type and transgenic controls and unheated wild-type controls. $T_3$ events of ME02526-04 and 05 were heat shocked for 4 hours as described above. ME02526-04 and -05 were able to stay greener longer than both pre-heat treated controls and un-heat treated controls. However, both ME02526 lines and all controls (wild-type and transgenic) failed to elongate and thrive after heat treatment at 45° C. and eventually all died. Un-heat treated wild-type control became chlorotic faster (1-day after treatment) than pre-heat treated wildtype control and pre-heat treated transgenic control suggesting that there is some natural acquired thermotolerance that occurs that is not correlated with the over-expression of 35S::cDNA 13488750. Even with exposure to this lethal temperature, ME02526 was greener after 7 days than controls, indicating that ME02526 has a thermotolerance phenotype that is unrelated to the natural mechanisms of acquired thermotolerance.

Figure 6:
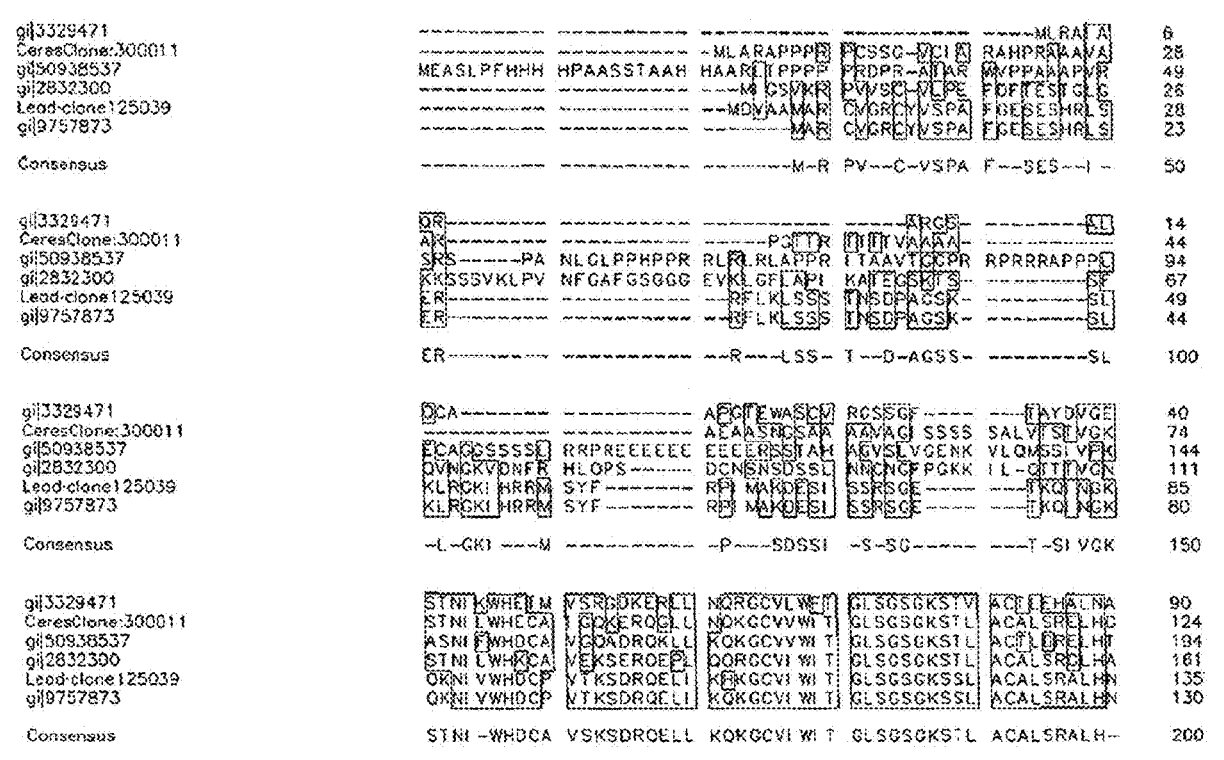

FIG. 6 provides the results of the consensus sequence (SEQ ID NOs: 201-214) analysis based on Ceres cDNA 13488750.

Example 8—Ceres cDNA 13489782

Clone 10044, Ceres cDNA 13489782, encodes a full-length putative 114-amino acid hypothetical protein from

*Arabidopsis thaliana*. Ectopic expression of Ceres cDNA 13489782 under the control of the 32449 promoter induces the following phenotypes:

Germination on high concentrations of polyethylene glycol (PEG) and abscissic acid (ABA) and Continued growth on high concentrations of PEG and ABA.

Generation and Phenotypic Evaluation of $T_1$ Lines Containing 32449::cDNA 13489782

Wild-type *Arabidopsis* Wassilewskija (WS) plants were transformed with a Ti plasmid containing cDNA 13489782 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol, and ABA as Surrogate Screens for Drought Tolerance Seeds from 13 superpools (1,200 $T_2$ seeds from each superpool) from the CaMV35S or 32449 over-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 13489782 was identified in resistant plants from each of the three surrogate drought screens, the five individual $T_2$ events containing this cDNA (ME00446) were screened on high PEG, mannitol, and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the 18$^{th}$ plant isolated from a mannitol screen of Superpool 1.

Qualitative Analysis of Superpools on PEG, Mannitol, and ABA.

Resistant candidates were selected based on increased size when compared to the largest wild-type control seedlings. All three screens resulted in a decrease in germination for both wildtype and superpools as compared to seeds on control media. Wild-type seeds that germinated on any of the screens were small and never developed any first leaves even after 40 days. To ensure that even slightly tolerant individuals were not omitted, seedlings that showed any growth and greening whatsoever were recovered and transferred to soil for assessment in the $T_3$ generation. All recovered candidates showed signs of vigorous re-growth on soil, although the development was slightly delayed as compared to unstressed plants, presumably because of the transient exposure to stress. The plants transferred to soil were sprayed with Basta to eliminate any false-positives, or any lines where the Basta$^R$ marker was suppressed. All of the Basta-resistant candidates flowered and set seed. Resistant seedlings were recovered from Superpools 1, 7 and 11 on all screens (Table 8-1).

TABLE 8-1

Number of stress-tolerant and Basta$^R$ seedlings identified on drought surrogate screens.

| Superpool | Promoter | 18% PEG | 375 mM Mannitol | 1.5 uM ABA |
|---|---|---|---|---|
| SP1 | 35S | 10 | 13 | 11 |
| SP2 | 35S | 0 | 6 | 5 |
| SP3 | 35S | 0 | 2 | 10 |
| SP4 | 35S | 0 | 4 | 0 |
| SP5 | 35S | 0 | 0 | 5 |
| SP6 | 35S | 0 | 0 | 4 |
| SP7 | 35S | 1 | 4 | 8 |
| SP8 | 35S | 0 | 4 | 1 |
| SP9 | 32449 | 0 | 0 | 12 |
| SP10 | 32449 | 0 | 0 | 14 |
| SP11 | 32449 | 15 | 3 | 13 |
| SP12 | 32449 | 3 | 0 | 6 |
| SP13 | 32449 | 0 | 2 | 1 |

We obtained sequence from 3, 3, and 13 plants that were both Basta$^R$ and resistant to PEG, mannitol or ABA, respectively. For each of the three surrogate drought screens, one or more plants contained the 32449::clone 10044 (ME00446). The probability of finding a plant containing this cDNA at random in all three screens is 0.03×0.03×0.03. Qualitative and Quantitative Analysis of 6 Independent Events Representing 32449::cDNA 13489782 on PEG, Mannitol and ABA To identify independent events of 32449:: cDNA 13489782 showing PEG, mannitol and ABA resistance, 36 seedlings from each of six events, ME00446-01, 02, 03, 04, 05 and 06 were screened as previously described. Simultaneously, Basta$^R$ segregation was assessed to identify lines containing a single insert segregating in a 3:1 (R:S) ratio as calculated by a Chi-square test (Table 8-2). All of the lines segregated for a single functional insert.

TABLE 8-2

Basta$^R$ segregation for 6 events of ME00446

| ME Line | Assessment | Did Not Germinate | Resistant | Sensitive | Total | Probability of Chi-test |
|---|---|---|---|---|---|---|
| 00446-01 | Oct. 30, 2003 | 1 | 28 | 7 | 35 | 0.49452 |
| 00446-02 | Oct. 30, 2003 | 0 | 28 | 8 | 36 | 0.70031 |
| 00446-03 | Oct. 30, 2003 | 1 | 28 | 7 | 35 | 0.49452 |
| 00446-04 | Oct. 30, 2003 | 1 | 27 | 8 | 35 | 0.7697 |
| 00446-05 | Oct. 30, 2003 | 2 | 24 | 10 | 34 | 0.55245 |
| 00446-06 | Oct. 30, 2003 | 0 | 25 | 11 | 36 | 0.44142 |

*Chi-test to determine whether actual ratio of resistant to sensitive differs from the expected 3:1 ratio.

Events ME00446-02 and 04 were chosen as the two events for further analysis because they had the strongest and most consistent resistance to PEG and ABA. None of the lines showed mannitol resistance at 375 mM concentration. The controls were sown the same day and in the same plate as the individual lines. The PEG (Tables 8-3 and 8-4) and ABA (Tables 8-5 and 8-6) segregation ratios observed for ME00446-02 and -04 are consistent with the presence of single insert as demonstrated by the Chi-Square test. This is similar to that observed for Basta resistance (Table 8-2).

Despite the fact that this line was isolated from all three screens, it was subsequently concluded that it could not be considered mannitol resistant. This is likely due to an overly stringent mannitol concentration. In a superpool screen setting, the seedlings are more densely grown than in an individual line setting. This means that in a superpool screen, there is a lower effective concentration of mannitol. When putative tolerant plant from a superpool is tested as an individual line, the effective concentration it is grown on is actually higher. In the case of ME00446, this difference was enough to invalidate it as mannitol tolerant. In fact, a resistant plant to mannitol was isolated from superpool 11 that corresponds to clone 10044.

TABLE 8-3

Chi-square analysis assuming a 3:1(R:S) ratio for progeny of ME00446-02 containing 32449::clone 10044 on PEG.

| Event | Observed | Expected | $\chi^2$ | Probability of $\chi^2$ |
|---|---|---|---|---|
| PEG Resistant | 30 | 26.95 | 0.3452 | 0.2557 |
| PEG Sensitive | 5 | 7.7 | 0.9468 | |
| Total | 35 | 35 | 1.292 | |

TABLE 8-4

Chi-square analysis assuming a 3:1(R:S) ratio for progeny of ME00446-04 containing 32449::clone 10044 on PEG.

| Event | Observed | Expected | $\chi^2$ | Probability of $\chi^2$ |
|---|---|---|---|---|
| PEG Resistant | 26 | 27.77 | 0.113 | 0.482 |
| PEG Sensitive | 10 | 8.23 | 0.3813 | |
| Total | 36 | 36 | 0.4943 | |

TABLE 8-5

Chi-square analysis assuming a 3:1(R:S) ratio for progeny of ME00446-02 containing 32449::clone 10044 on ABA.

| Event | Observed | Expected | $\chi^2$ | Probability of $\chi^2$ |
|---|---|---|---|---|
| ABA Resistant | 31 | 27 | 0.5926 | 0.1237 |
| ABA Sensitive | 5 | 9 | 1.778 | |
| Total | 36 | 36 | 2.370 | |

TABLE 8-6

Chi-square analysis assuming a 3:1(R:S) ratio for progeny of ME00446-04 containing 32449::clone 10044 on ABA.

| Event | Observed | Expected | $\chi^2$ | Probability of $\chi^2$ |
|---|---|---|---|---|
| ABA Resistant | 31 | 27 | 0.5926 | 0.1237 |
| ABA Sensitive | 5 | 9 | 1.778 | |
| Total | 36 | 36 | 2.370 | |

Qualitative and Quantitative Analysis of Progeny of $T_2$ Plants Isolated on PEG, Mannitol and ABA Progeny from $T_2$ plants that were recovered from the three screens and containing clone 10044 (SP11-M13 and SP11-P5) were found to be resistant to PEG and ABA. Taken together, 1) the isolation of resistant seedlings containing clone 10044 from all three surrogate screens for drought, 2) the inheritance of this resistance in the next generation, and 3) the fact that the progeny from two or more events from the original transformation also segregated for resistance to these osmotic stresses, provide strong evidence that clone 10044 when over-expressed provides resistance to osmotic and dehydration stress.

FIG. 7 provides the results of the consensus sequence (SEQ ID NOs: 215-222) analysis based on Ceres cDNA 13489782.

Example 9—Ceres cDNA 13486759

Clone 10987, corresponding Ceres cDNA 13486759, encodes an *Arabidopsis* 251-amino acid expressed protein. Ectopic expression of clone 10987 under the control of the CaMV35S promoter induces the following phenotypes:
  Germination on high concentrations of polyethylene glycol (PEG), mannitol, and abscissic acid (ABA), and
  Continued growth on high concentrations of PEG, mannitol, and ABA.

Generation and Phenotypic Evaluation of $T_1$ Lines Containing 35S::cDNA 13486759

Wild-type *Arabidopsis* Wassilewskija (WS) plants were transformed with a Ti plasmid containing cDNA 13486759 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol and ABA as Surrogate Screens for Drought Tolerance Seeds from 13 superpools (1,200 $T_2$ seeds from each superpool) from the CaMV35S or 32449 over-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 13486759 was identified in resistant plants from each of the three surrogate drought screens, the five individual $T_2$ events containing this cDNA (ME03316) were screened on high PEG, mannitol, and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the 18$^{th}$ plant isolated from a mannitol screen of Superpool 1.

Qualitative Analysis of 13 Superpools on PEG, Mannitol and ABA

Resistant candidates were selected based on increased size when compared to the largest wild-type control seedlings. All three screens resulted in a decrease in germination for both wildtype and superpools as compared to seeds on control media. Wild-type seeds that germinated on any of the screens were small and never developed any first leaves even after 40 days. To ensure that even slightly tolerant individuals were not omitted, seedlings that showed any growth and greening whatsoever were recovered and transferred to soil for assessment in the $T_3$ generation. All recovered candidates showed signs of vigorous re-growth on soil, although the development was slightly delayed as compared to unstressed plants, presumably because of the transient exposure to stress. The plants transferred to soil were sprayed with Basta to eliminate any false-positives, or any lines where the Basta$^R$ marker was suppressed. All of the Basta-resistant candidates flowered and set seed. Resistant seedlings were recovered from Superpools 1, 7 and 11 on all screens (Table 9-1).

TABLE 9-1

Number of stress-tolerant and Basta$^R$ seedlings identified on drought surrogate screens.

| Superpool | Promoter | 18% PEG | 375 mM Mannitol | 1.5 uM ABA |
|---|---|---|---|---|
| SP1 | 35S | 10 | 13 | 11 |
| SP2 | 35S | 0 | 6 | 5 |
| SP3 | 35S | 0 | 2 | 10 |
| SP4 | 35S | 0 | 4 | 0 |
| SP5 | 35S | 0 | 0 | 5 |
| SP6 | 35S | 0 | 0 | 4 |
| SP7 | 35S | 1 | 4 | 8 |
| SP8 | 35S | 0 | 4 | 1 |
| SP9 | 32449 | 0 | 0 | 12 |
| SP10 | 32449 | 0 | 0 | 14 |
| SP11 | 32449 | 15 | 3 | 13 |
| SP12 | 32449 | 3 | 0 | 6 |
| SP13 | 32449 | 0 | 2 | 1 |

We obtained sequence from 3, 3, and 13 plants from Superpool 11 that were both Basta$^R$-resistant and resistant to PEG, mannitol or ABA, respectively. For each of the three osmotic screens, one or more plants contained the 35S::clone 10987 (ME03316), which made it a good candidate for further testing. The probability of finding a plant containing this clone 10987 at random in all three screens is 0.03×0.03. Qualitative and Quantitative Analysis of 5 Independent Events Representing 35S::cDNA 13486759 on PEG, Mannitol and ABA To identify independent events of 35S::cDNA 13486759 showing PEG, mannitol and ABA resistance, 36 seedlings from each of five events, ME03316-01, -02, -03, -04, and -05 were screened as previously described. Simultaneously, Basta$^R$ segregation was assessed to identify events containing a single insert segregating in a 3:1 (R:S) ratio as calculated by a chi-square test (Table 9-2). All of the events segregated for a single functional insert. ME03316-02 could be segregating for two linked or unlinked inserts but the ratios on the surrogate drought screens indicate it is likely to be a single insert.

TABLE 9-2

Basta$^R$ segregation for 5 individual events

| Event | Resistant | Sensitive | Total | Probability of Chi-test |
|---|---|---|---|---|
| ME03316-01 | 23 | 13 | 36 | 0.12366 |
| ME03316-02 | 32 | 4 | 36 | 0.05429 |
| ME03316-03 | 30 | 6 | 36 | 0.24821 |
| ME03316-04 | 25 | 11 | 36 | 0.44142 |
| ME03316-05 | 29 | 7 | 36 | 0.44142 |

*Chi-test to determine whether actual ratio of resistant to sensitive differs from the expected 3:1 ratio.

Lines ME03316-01 and 02 were chosen as the two events for further analysis because they had the strongest and most consistent resistance to PEG, mannitol and ABA. Resistance was observed for ME03316-03, 04, and 05 although not in expected ratios in all three screens (data not shown). The controls were sown the same day and on the same plate as the individual lines. The PEG (Tables 9-3 and 9-4), mannitol (Tables 9-5 and 9-6) and ABA (Table 9-7) segregation ratios observed are consistent with the presence of a single insert as demonstrated by chi-square. ME03316-02 seedlings on ABA (Table 9-8) appear to be segregating for two inserts which is still consistent with the ratio observed on Basta$^R$. Both events segregate for a deficiency of resistant

TABLE 9-3

Chi-square analysis assuming a 3:1 (R:S) ratio for progeny of ME03316-01 containing 35S::clone 10987 on PEG.

| Event | Observed | Expected | $\chi^2$ | Probability of Chi-Test |
|---|---|---|---|---|
| PEG Resistant | 22 | 27 | 0.93 | 0.0543 |
| PEG Sensitive | 14 | 9 | 2.78 | |
| Total | 36 | 36 | 3.7 | |

TABLE 9-4

Chi-square analysis assuming a 3:1 (R:S) ratio for progeny of ME03316-02 containing 35S::clone 10987 on PEG.

| Event | Observed | Expected | $\chi^2$ | Probability of Chi-Test |
|---|---|---|---|---|
| PEG Resistant | 23 | 26.25 | 0.4024 | 0.2046 |
| PEG Sensitive | 12 | 8.75 | 1.2071 | |
| Total | 35 | 35 | 1.610 | |

TABLE 9-5

Chi-square analysis assuming a 3:1 (R:S) ratio for progeny of ME03316-01 containing 35S::clone 10987 on Mannitol.

| Event | Observed | Expected | $\chi^2$ | Probability of Chi-Test |
|---|---|---|---|---|
| Mannitol Resistant | 19 | 25.5 | 1.657 | 0.01 |
| Mannitol Sensitive | 15 | 8.5 | 4.971 | |
| Total | 34 | 34 | 6.63 | |

TABLE 9-6

Chi-square analysis assuming a 3:1 (R:S) ratio for progeny of ME03316-02 containing 35S::clone 10987 on Mannitol.

| Event | Observed | Expected | $\chi^2$ | Probability of Chi-Test |
|---|---|---|---|---|
| Mannitol Resistant | 18 | 26.25 | 2.593 | 0.0013 |
| Mannitol Sensitive | 17 | 8.75 | 7.779 | |
| Total | 35 | 35 | 10.371 | |

TABLE 9-7

Chi-square analysis assuming a 3:1 (R:S) ratio for progeny of ME03316-01 containing 35S::clone 10987 on ABA.

| Event | Observed | Expected | $\chi^2$ | Probability of Chi-Test |
|---|---|---|---|---|
| ABA Resistant | 27 | 25.5 | 0.0882 | 0.5525 |
| ABA Sensitive | 7 | 8.5 | 0.2647 | |
| Total | 34 | 34 | 0.3529 | |

TABLE 9-8

Chi-square analysis assuming a 3:1 (R:S) ratio for progeny of ME03316-02 containing 35S::clone 10987 on ABA.

| Event | Observed | Expected | $\chi^2$ | Probability of Chi-Test |
|---|---|---|---|---|
| ABA Resistant | 32 | 24.75 | 2.124 | 0.0036 |
| ABA Sensitive | 1 | 8.25 | 6.371 | |
| Total | 33 | 33 | 8.495 | |

Qualitative and Quantitative Analysis of Progeny of $T_2$ Plants Isolated on PEG, Mannitol and ABA Progeny from $T_2$ plants that were recovered from the three screens and containing clone 10987 (SP 11-A 15, SP11-A16, SP 11-P2, and SP 11-M10) were found to be resistant to PEG, mannitol and ABA.

On PEG, the progeny of SP11-M10 segregated for a deficiency of resistant seedlings similar to the deficiency that noted for the T2 seedlings in Tables 9-5 and 9-6. A deficiency of resistant seedlings is also noted for the progeny of SP11P2 on PEG.

Taken together, 1) the isolation of resistant seedlings containing clone 10987 from all three surrogate screens for drought, 2) the inheritance of this resistance in the next generation, and 3) the fact that the progeny from two or more events from the original transformation also segregated for resistance to these osmotic stresses, these findings provide strong evidence that clone 10987 when over-expressed can provide tolerance to osmotic stresses.

Example 10—Ceres cDNA 13500101

Clone 17206, corresponding to Ceres cDNA 13500101, encodes a putative strictosidine synthase. Ectopic expression of cDNA 13500101 under the control of the CaMV35S promoter induces the following phenotypes:
  Germination on high concentrations of polyethylene glycol (PEG) and mannitol.
  Continued growth on high concentrations of PEG and mannitol.

Generation and Phenotypic Evaluation of $T_1$ Lines Containing 35S::cDNA 13500101.

Wild-type *Arabidopsis* Wassilewskija (WS) plants were transformed with a Ti plasmid containing cDNA 13500101 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol, and ABA as Surrogate Screens for Drought Tolerance.

Seeds from 13 superpools (1,200 $T_2$ seeds from each superpool) from the CaMV35S or 32449 over-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 13500101 was identified in resistant plants from each of the three surrogate drought screens, the five individual $T_2$ events containing this cDNA (SR01000) were screened on high PEG, mannitol, and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the 18th plant isolated from a mannitol screen of Superpool 1.

Qualitative and Quantitative Analysis of 2 Independent Events Representing 35S::cDNA 13500101 (SR01000) on PEG, Mannitol and ABA To identify two independent events of 35S::clone 17206 showing PEG, mannitol, and ABA resistance, 36 seedlings from each of three events, SR01000-01, 02 and 03 were screened as previously described. Basta segregation was assessed to verify that the lines contained a single insert segregating in a 3:1 (R:S) ratio as calculated by a chi-square test (Table 1). Two lines (-01 and -02) segregated for a single insert (Table 1).

TABLE 10-1

Basta[R] segregation for SR01000 individual events

| Event | Resistant | Sensitive | Total | Probability of Chi-test |
|---|---|---|---|---|
| SR01000-01 | 29 | 7 | 36 | 0.44142 |
| SR01000-02 | 23 | 13 | 36 | 0.12366 |
| SR01000-03 | 35 | 0 | 35 | 0.00064 |
| SR01000-01-01 | 35 | 0 | 35 | 0.00064 |
| SR01000-02-01 | 27 | 9 | 36 | 1 |
| SR01000-03-01 | 36 | 0 | 36 | 0.00053 |

*Chi-test to determine whether actual ratio of resistant to sensitive differs from the expected 3:1 ratio.

Testing of the progeny from the $T_2$ resistant plants on the 3 surrogate drought screens showed that lines SR01000-01 and 02 had a strong and consistent resistance to PEG, mannitol, but not to ABA. These were chosen as the two events for further analysis. The controls were sown the same day and in the same plate as the individual lines. The PEG (Tables 10-2 and 10-3), and mannitol (Tables 10-4 and 10-5) segregation ratios observed for SR01000-01 and 02 are consistent with the presence a of single insert as demonstrated by chi-square (Table 10-1).

TABLE 10-2

Chi-square analysis assuming a 3:1 (R:S) ratio for progeny of SR01000-01 $T_2$ containing 35S::cDNA 13500101 on PEG.

| Event | Observed | Expected | $\chi^2$ | Probability of Chi-Test |
|---|---|---|---|---|
| PEG Resistant | 26 | 26.25 | 0.002 | 0.922 |
| PEG Sensitive | 9 | 8.75 | 0.007 | |
| | 35 | 35 | 0.009 | |

TABLE 10-3

Chi-square analysis assuming a 3:1 (R:S) ratio for progeny of SR01000-02 $T_2$ containing 35S::cDNA 13500101 on PEG.

| Event | Observed | Expected | $\chi^2$ | Probability of Chi-Test |
|---|---|---|---|---|
| PEG Resistant | 27 | 24.75 | 0.205 | 0.366 |
| PEG Sensitive | 6 | 8.25 | 0.614 | |
| | 33 | 33 | 0.818 | |

TABLE 10-4

Chi-square analysis assuming a 3:1 (R:S) ratio for progeny of SR01000-01 $T_2$ containing 35S::cDNA 13500101 on mannitol.

| Event | Observed | Expected | $\chi^2$ | Probability of Chi-Test |
|---|---|---|---|---|
| Mannitol Resistant | 28 | 27 | 0.037 | 0.700 |
| Mannitol Sensitive | 8 | 9 | 0.111 | |
| | 36 | 36 | 0.148 | |

TABLE 10-5

Chi-square analysis assuming a 3:1 (R:S) ratio for progeny of SR01000-02 $T_2$ containing 35S::cDNA 13500101 on mannitol.

| Event | Observed | Expected | $\chi^2$ | Probability of Chi-Test |
|---|---|---|---|---|
| Mannitol Resistant | 30 | 27 | 0.333 | 0.248 |
| Mannitol Sensitive | 6 | 9 | 1.000 | |
| | 36 | 36 | 1.333 | |

Qualitative and Quantitative Analysis of Progeny of $T_2$ Plants Isolated on PEG, Mannitol and ABA The progeny from one resistant $T_2$ plant from each of these two events were tested in the same manner as the $T_2$. Resistance to PEG and mannitol persisted in the second generation. Taken together, 1) the isolation of resistant seedlings containing clone 17026 from two of the surrogate screens for drought (PEG and mannitol), 2) the inheritance of this resistance in the next generation, and 3) the fact that the progeny from two or more events from the original transformation also segregated for resistance to these osmotic stresses, these findings provide strong evidence that clone 17026 when over-expressed can provide tolerance to osmotic stresses.

Figure 8:
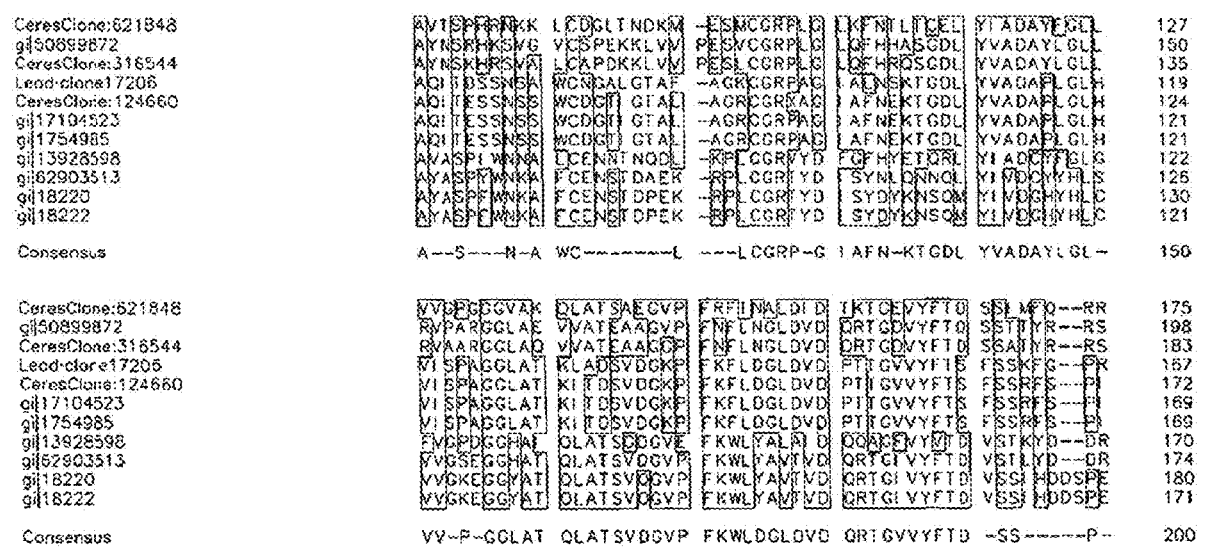
Figure 8:
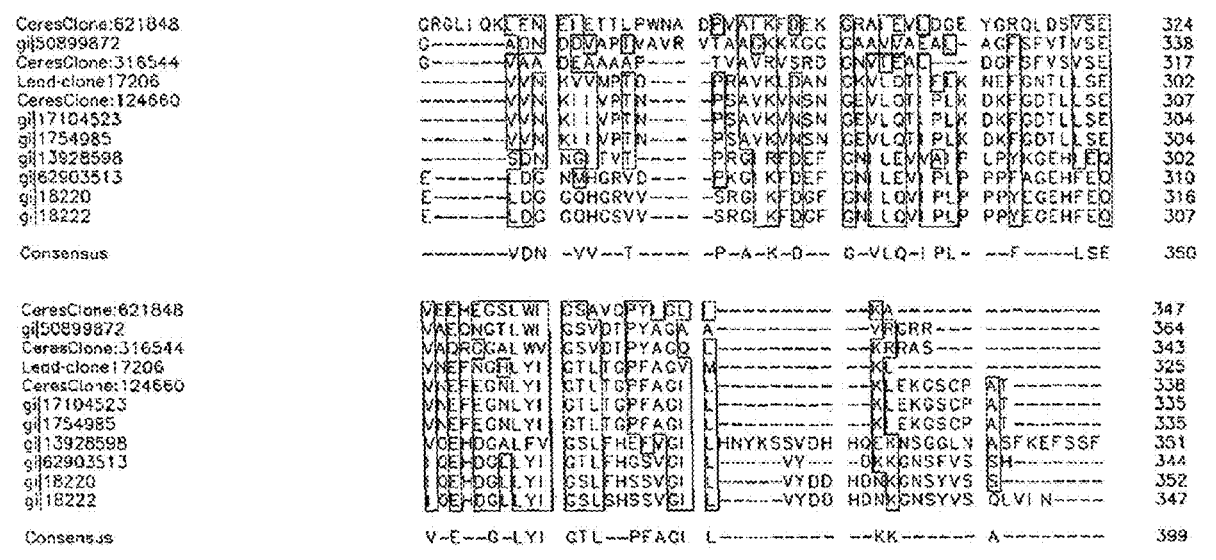

FIG. 8 provides the results of the consensus sequence (SEQ ID NOs: 223-240) analysis based on Ceres cDNA 13500101.

Example 11—Ceres cDNA 13509011 (12357529)

Clone 104691, corresponding to Ceres cDNA 13509011 (12357529), encodes a probable strictosidine synthase enzyme. Ectopic expression of cDNA 13509011 under the control of the CaMV35S promoter induces the following phenotypes:

Germination on high concentrations of polyethylene glycol (PEG) and mannitol.

Continued growth on high concentration of PEG and mannitol.

Generation and Phenotypic Evaluation of $T_1$ Lines Containing 35S::cDNA 13509011.

Wild-type *Arabidopsis* Wassilewskija (WS) plants were transformed with a Ti plasmid containing cDNA 12334963 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol, and ABA as Surrogate Screens for Drought Tolerance.

Seeds from 13 superpools (1,200 $T_2$ seeds from each superpool) from the CaMV35S or 32449 over-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 13509011 was identified in resistant plants from each of the three surrogate drought screens, the five individual $T_2$ events containing this cDNA (SR01002) were screened on high PEG, mannitol, and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the 18$^{th}$ plant isolated from a mannitol screen of Superpool 1.

Qualitative and Quantitative Analysis of 2 Independent Events Representing 35S::Clone 104691 (SR01002) on PEG, Mannitol and ABA To identify two independent events of 35S::clone 104691 showing PEG, mannitol and ABA resistance, 36 seedlings from each of three events, SR01002-01, 02, and 03 were screened as previously described. Simultaneously, Basta segregation was assessed to identify lines containing a single insert segregating in a 3:1 (R:S) ratio as calculated by a chi-square test (Table 1). Two lines (01 and 03) segregated for a single insert.

TABLE 11-1

Basta segregation for SR01002 individual events

| Event | Resistant | Sensitive | Total | Probability of Chi-test |
|---|---|---|---|---|
| SR01002-01 | 26 | 10 | 36 | 0.70031 |
| SR01002-02 | 23 | 8 | 31 | 0.91741 |
| SR01002-03 | 28 | 8 | 36 | 0.70031 |
| SR01002-01-1 | 36 | 0 | 36 | 0.00053 |
| SR01002-02-1 | 28 | 8 | 36 | 0.70031 |
| SR01002-03-1 | 25 | 11 | 36 | 0.44142 |

*Chi-test to determine whether actual ratio of resistant to sensitive differs from the expected 3:1 ratio.

Testing of the progeny from the resistant $T_2$ plants on the 3 surrogate drought screens showed that lines SR01002-01 and 03 had a strong and consistent resistance to PEG, mannitol, but not to ABA. These were chosen as the two events for further analysis. The controls were sown the same day and in the same plate as the individual lines. The PEG (Tables 11-2 and 11-3), and mannitol (Tables 11-4 and 11-5) segregation ratios observed for SR01002-01 and 03 are consistent with the presence of a single insert as demonstrated by chi-square. This is similar to that observed for Basta resistance (Table 11-1).

TABLE 11-2

Chi-square analysis assuming a 3:1 (R:S) ratio for progeny of SR01002-01 $T_2$ containing 35S::clone 104691 on PEG.

| Event | Observed | Expected | $\chi^2$ | Probability |
|---|---|---|---|---|
| PEG Resistant | 22 | 24.75 | 0.306 | 0.269 |
| PEG Sensitive | 11 | 8.25 | 0.917 | |
| | 33 | 33 | 1.222 | |

TABLE 11-3

Chi-square analysis assuming a 3:1 (R:S) ratio for progeny of SR01002-03 $T_2$ containing 35S::clone 104691 on PEG.

| Event | Observed | Expected | $\chi^2$ | Probability |
|---|---|---|---|---|
| PEG Resistant | 24 | 25.5 | 0.088 | 0.552 |
| PEG Sensitive | 10 | 8.5 | 0.265 | |
| | 34 | 34 | 0.353 | |

TABLE 11-4

Chi-square analysis assuming a 3:1 (R:S) ratio for progeny of SR01002-01 $T_2$ containing 35S::clone 104691 on mannitol.

| Event | Observed | Expected | $\chi^2$ | Probability |
|---|---|---|---|---|
| Mannitol Resistant | 30 | 27 | 0.333 | 0.248 |
| Mannitol Sensitive | 6 | 9 | 1.000 | |
| | 36 | 36 | 1.333 | |

TABLE 11-5

Chi-square analysis assuming a 3:1 (R:S) ratio for progeny of SR01002-03 $T_2$ containing 35S::clone 104691 on mannitol.

| Event | Observed | Expected | $\chi^2$ | Probability |
|---|---|---|---|---|
| Mannitol Resistant | 32 | 27 | 0.926 | 0.054 |
| Mannitol Sensitive | 4 | 9 | 2.78 | |
| | 36 | 36 | 3.70 | |

Qualitative and Quantitative Analysis of Progeny of $T_2$ Plants Isolated on PEG, Mannitol, and ABA Screens.

The progeny from one resistant $T_2$ plant from each of these two events was tested in the T3 generation in the same manner. Resistance to PEG and mannitol persisted into the next generation. Taken together, 1) the isolation of resistant seedlings containing clone 104691 from two of the surrogate screens for drought (PEG and mannitol), 2) the inheritance of this resistance in the next generation, and 3) the fact that the progeny from two or more events from the original transformation also segregated for resistance to these surrogate drought conditions, these findings provide strong evidence that clone 104691 when over-expressed can provide tolerance to osmotic stresses.

Figure 9:
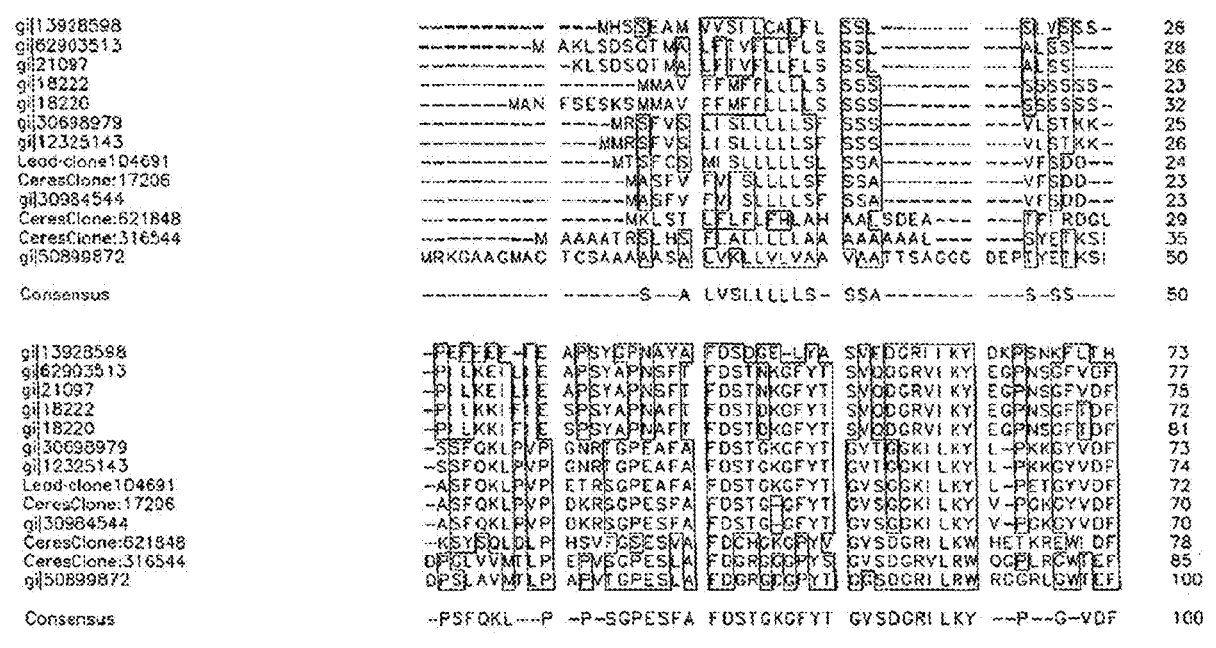
Figure 9:
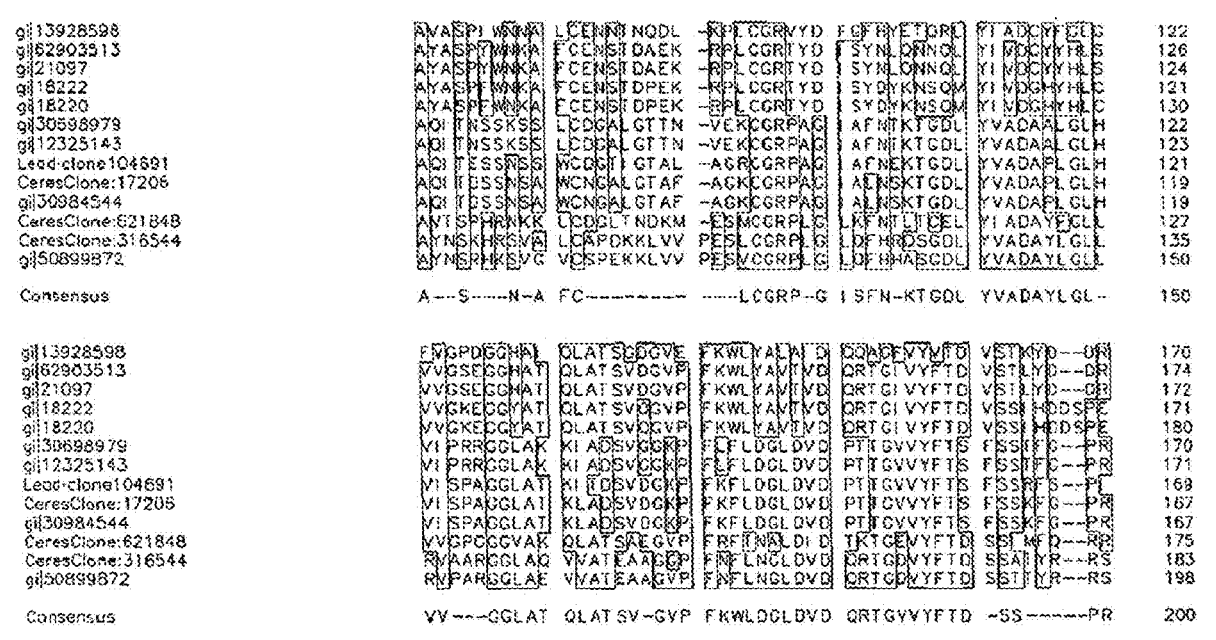
Figure 9:
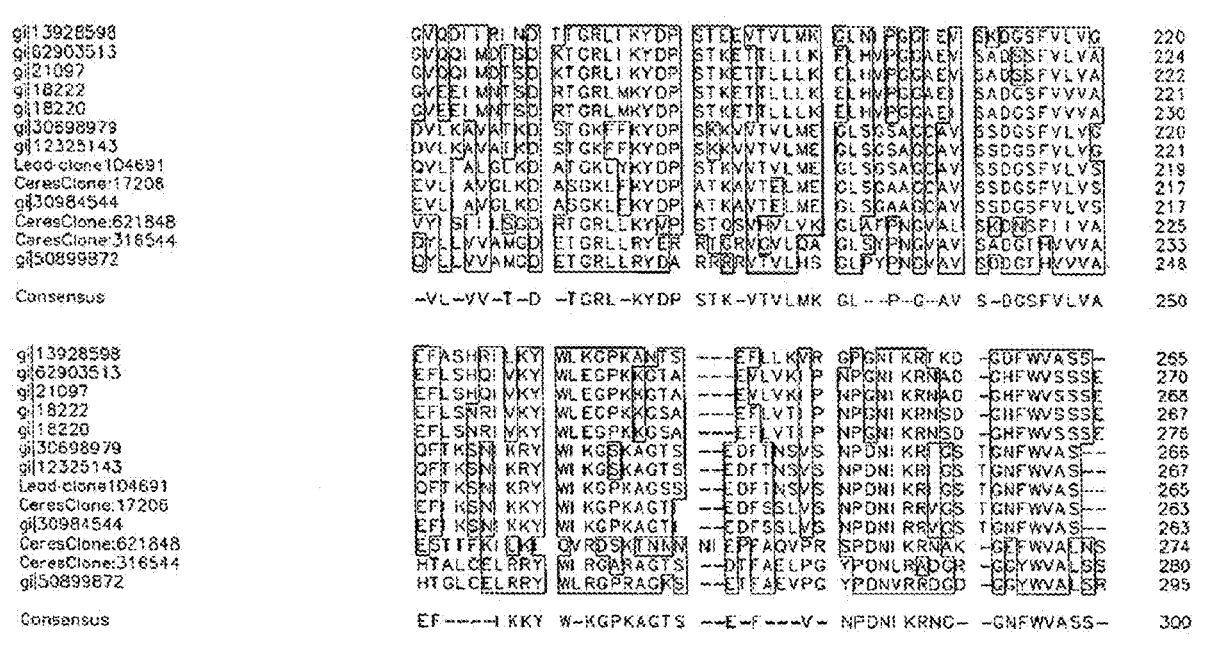
Figure 9:
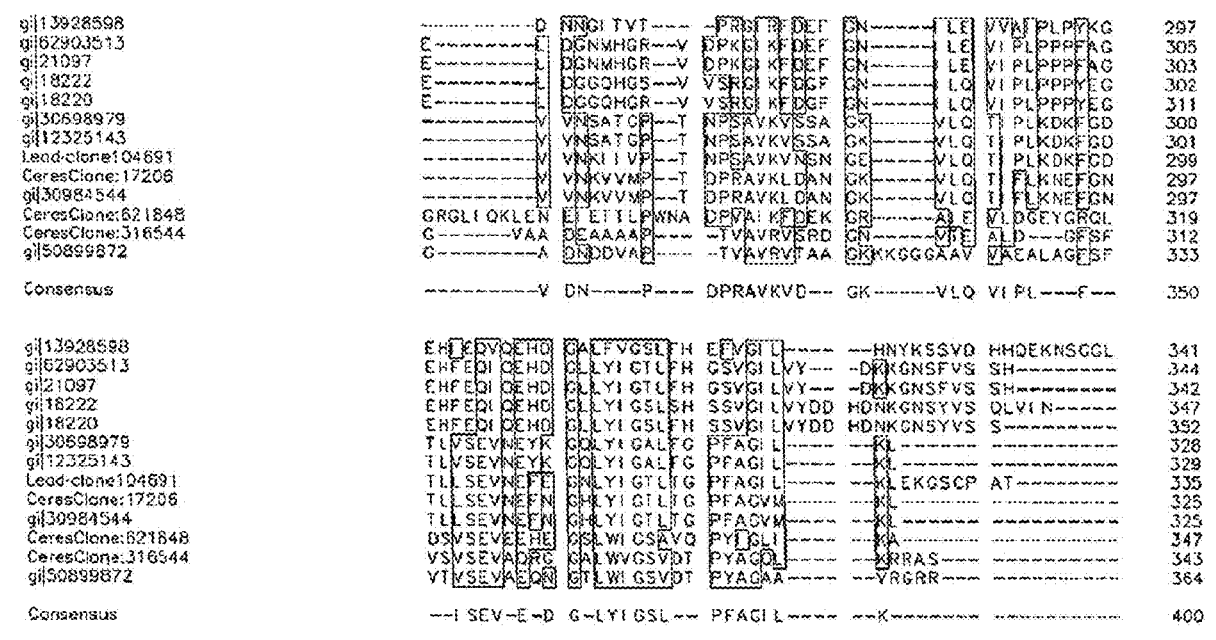

FIG. 9 provides the results of the consensus sequence (SEQ ID NOs: 241-262) analysis based on Ceres cDNA 13509011 (12357529).

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

SEQUENCE LISTING

```
Sequence total quantity: 262
SEQ ID NO: 1            moltype = DNA  length = 577
FEATURE                 Location/Qualifiers
misc_feature            1..577
                        note = clone11830_inplanta_experimental_L18
source                  1..577
                        mol_type = other DNA
                        organism = Arabidopsis thaliana
SEQUENCE: 1
aaacttccta actagataga tcagatctgg atctctctgc accactcatt gccttctcta    60
gaaacatgtc aactttcttg ataaggatac ttcttccttt gcttatcata gcaatgactc   120
ttcctcgacg ttcagaggca gagtcggaac aatggtgcat agcggatgaa caaacgccag   180
acgatgagtt gcaagcagcc ttagactggg cttgcgaaa  aggtggagca gactgcagca   240
aaatgcagca ggaaaaccag ccttgcttct tgcctaacac aatcagagat catgcctcct   300
ttgctttcaa cagttactac caaacttata aaaacaaagg tggttcttgt tacttcaaag   360
gagctgccat gatcactgag cttgacccca gccatggttc ttgccagtat gagtataacc   420
cctgattcaa acgacacagc aaagacaaga tacagcaaga tgaaaagcta tgattttgca   480
tttatacgtt ttctctatgt aatgttttca ttccaaagca gtatccatgt actgttctcc   540
cattacactc cagtctgaga taaaaatttc ttcaacg                            577

SEQ ID NO: 2            moltype = AA  length = 119
FEATURE                 Location/Qualifiers
REGION                  1..119
                        note = peptide_clone11830_inplanta_experimental_L18
source                  1..119
                        mol_type = protein
                        organism = Arabidopsis thaliana
SEQUENCE: 2
MSTFLIRILL PLLIIAMTLP RRSEAESEQW CIADEQTPDD ELQAALDWAC GKGGADCSKM    60
QQENQPCFLP NTIRDHASFA FNSYYQTYKN KGGSCYFKGA AMITELDPSH GSCQYEYNP   119
```

```
SEQ ID NO: 3                moltype = AA   length = 118
FEATURE                     Location/Qualifiers
REGION                      1..118
                            note = CeresClone:1058242
source                      1..118
                            mol_type = protein
                            organism = Glycine max
SEQUENCE: 3
MATFMLKLVL PLLFLFMIPP KTAYAEFEQW CVADEQTTES ELQAALDWAC GKGGADCSKI   60
QVNQPCYLPN TLKDHASYAF NSYYQKFKHS GGSCYFRGAA ITTEVDPSHG SCHYDFIP   118

SEQ ID NO: 4                moltype = AA   length = 123
FEATURE                     Location/Qualifiers
REGION                      1..123
                            note = gi[29]465664
source                      1..123
                            mol_type = protein
                            organism = Olea europaea
SEQUENCE: 4
MRGTAGVPDQ PVPTPTPSVP TSSSPVPKPP TQGNKKWCVP KAEATDAQLQ SNIDYVCSQS   60
GMDCGPIQAN GACFNPNTVR AHASYAMNSW YQSKGRNDFD CDFSGTGAIT SSDPSNGSCS  120
FLS                                                                123

SEQ ID NO: 5                moltype = AA   length = 123
FEATURE                     Location/Qualifiers
REGION                      1..123
                            note = CeresClone:1602924
source                      1..123
                            mol_type = protein
                            organism = Parthenium argentatum
SEQUENCE: 5
MTTVTTPHFI TVLFFFLLIS GGIFGHAKAQ APGQGTWCVA KPATSDEDLQ NNINYACTYV   60
DCRIIRPGSV CFEPQKLVNR ASVAMNLYYQ TNGRNYWNCD FKGSGIIAVT DPSYGDCKYS  120
YKQ                                                                123

SEQ ID NO: 6                moltype = DNA   length = 703
FEATURE                     Location/Qualifiers
misc_feature                1..703
                            note = clone35743_inplanta_experimental_L19
source                      1..703
                            mol_type = other DNA
                            organism = Arabidopsis thaliana
SEQUENCE: 6
caataaccac aaacaacaat acacttctct tgacgcctat ctctttctca ccaccaccat   60
taccttcgtc acttctctct tccaagcaat ttaaaccttc aactaatcca gaaatgcaaa  120
tgctaagaaa cttaagcacg aggacgagga gtcgtcgcgg cggatatgag cgtgtaagcg  180
atgattccac cttcagccta cttggagcaa agctaaggag gtcaacgagc gttccatact  240
atgctccatc gataaggctt ggtggagatt ttcctgtgat tttggaaaag cttccacgcc  300
aaaaaccaac taaaacagtg gtgacaagca aattaagcca tccaatcttc agtttatttg  360
atggttatcg ccgccgtagc aagaagaaag cgacggccaa accggagttc tctagatacc  420
atgaataacct taaagaaagt ggaatgtggg atttggagatc taatagtccg gtcatctact  480
ttaagtagat atatatataa cactatatat gttatgattt gtgttcattt attatattat  540
ttgtgacaat tcttagtgat atgattgatc gatctataag agctatcttc agtttttatt  600
tttctccccc ttgtaaatat tttttaattt gatctataaa tttaaacaca acgttttttg  660
gtcaacagtc ttgtgttatt ctattgtaaa cacaacgttt acc                    703

SEQ ID NO: 7                moltype = AA   length = 124
FEATURE                     Location/Qualifiers
REGION                      1..124
                            note = peptide_clone35743_inplanta_experimental_L19
source                      1..124
                            mol_type = protein
                            organism = Arabidopsis thaliana
SEQUENCE: 7
MQMLRNLSTR TRSRRGGYER VSDDSTFSLL GAKLRRSTSV PYYAPSIRLG GDFPVILEKL   60
PRQKPTKTVV TSKLSHPIFS LFDGYRRRSK KKATAKPEFS RYHEYLKESG MWDLRSNSPV  120
IYFK                                                               124

SEQ ID NO: 8                moltype = AA   length = 124
FEATURE                     Location/Qualifiers
REGION                      1..124
                            note = gi[38]603980
source                      1..124
                            mol_type = protein
                            organism = Arabidopsis thaliana
```

```
SEQUENCE: 8
MQMLRNLSTR TRSRRGGYER VSDDSTFSLL GAKLRRSTSV PYYAPSIRLG GDFPVILEKL    60
PRQKPTKTVV TSKLSHPIFS LFDGYRRHNK KKATAKPEFS RYHEYLKESG MWDLRSNSPV   120
IYFK                                                                124

SEQ ID NO: 9            moltype = AA  length = 118
FEATURE                 Location/Qualifiers
REGION                  1..118
                        note = CeresClone:963524
source                  1..118
                        mol_type = protein
                        organism = Brassica napus
SEQUENCE: 9
MQMLRSFSTR TRSRRGGYER VIDDSTFSLL GAKLRRSTSV PYYAPSIKLG AGGVPTILEE    60
LPRQKSKKVK PTSKFSHPIF SFLYGKKKKS TTRKPEFSRY LEYLKEGGMW DARTNTPV    118

SEQ ID NO: 10           moltype = DNA  length = 870
FEATURE                 Location/Qualifiers
misc_feature            1..870
                        note = clone26006_inplanta_experimental_L20
source                  1..870
                        mol_type = other DNA
                        organism = Arabidopsis thaliana
SEQUENCE: 10
aaaaagtacg aaaggaaaat atgagtgagg agaagaggaa gcaacacttc gtgctagtac    60
atggtgcgtg ccacggcgca tggtgctggt acaaggttaa gcctcttctc gaggctttgg   120
gccatcgtgt aaccgcctta gacctagctg cttccggtat agacacaacc aggtcaatca   180
ctgacatttc tacatgtgaa caatattctg agccattgat gcagctaatg acttcattgc   240
cgaatgatga gaaggttgta ctcgttggtc atagctttgg aggtttgagt ttagccttag   300
ccatggatgaa gtttcccgat aaaatctctg tctctgtctt cgtgactgca ttcatgcccg   360
acaccaaaca ctcaccatcg ttcgtcgagg aaaagtttgc aagcagcatg acaccagaag   420
gatggatggg ctctgagctc gagacatatg gttcagataa ttccggcttg tctgtgttct   480
tcagcaccga cttcatgaag caccgtctct accaactttc tcctgtggag gatcttgagc   540
ttgagattgct tctaaagagg cctagttcat tgtttattaa tgaattcgaa aagtggaga   600
acttttctga gaaagggtat ggatctgttc ctcgagctta cattgtgtgc aaagaggaca   660
acattatctc ggaagaccat caacgatgga tgatccataa ttatccggcg aatttagtga   720
ttgagatgga agagacggat catatgccaa tgtttttgcaa acctcaagta ctaagtgacc   780
atctattggc aatcgctgac aatttctctt aaataatatt ttgatgaaaa tgtatttgga   840
gtggatacaa taaaaatgtg ttctaaatgg                                    870

SEQ ID NO: 11           moltype = AA  length = 263
FEATURE                 Location/Qualifiers
REGION                  1..263
                        note = peptide_clone26006_inplanta_experimental_L20
source                  1..263
                        mol_type = protein
                        organism = Arabidopsis thaliana
SEQUENCE: 11
MSEEKRKQHF VLVHGACHGA WCWYKVKPLL EALGHRVTAL DLAASGIDTT RSITDISTCE    60
QYSEPLMQLM TSLPNDEKVV LVGHSFGGLS LALAMDKFPD KISVSVFVTA FMPDTKHSPS   120
FVEEKFASSM TPEGWMGSEL ETYGSDNSGL SVFFSTDFMK HRLYQLSPVE DLELGLLLKR   180
PSSLFINELS KMENFSEKGY GSVPRAYIVC KEDNIISEDH QRWMIHNYPA NLVIEMEETD   240
HMPMFCKPQV LSDHLLAIAD NFS                                           263

SEQ ID NO: 12           moltype = AA  length = 267
FEATURE                 Location/Qualifiers
REGION                  1..267
                        note = gi[14]279437
source                  1..267
                        mol_type = protein
                        organism = Citrus sinensis
SEQUENCE: 12
MEEVVGMEEK HFVLVHGVNH GAWCWYKLKA RLVAGGHRVT AVDLAASGIN MKRIEDVHTF    60
HAYSEPLMEV LASLPAEEKV ILVGHSLGGV TLALAGDKFP HKISVAVFVT AFMPDTTHRP   120
SFVLEQYSEK MGKEDDSWLD TQFSQCDASN PSHISMLFGR EFLTIKIYQL CPPEDLELAK   180
MLVRPGSMFI DNLSKESKFS DEGYGSVKRV YLVCEEDIGL PKQFQHWMIQ NYPVNEVMEI   240
KGGDHMAMLS DPQKLCDCLS QISLKYA                                       267

SEQ ID NO: 13           moltype = AA  length = 263
FEATURE                 Location/Qualifiers
REGION                  1..263
                        note = CeresClone:1010900
source                  1..263
                        mol_type = protein
                        organism = Arabidopsis thaliana
SEQUENCE: 13
MSEEKRKQHF VLVHGSCHGA WCWYKVKPLL EAVGHRVTAV DLAASGIDTT RSITDIPTCE    60
QYSEPLTKLL TSLPNDEKVV LVGHSFGGLN LAIAMEKFPE KISVAVFLTA FMPDTEHSPS   120
FVLDKFGSNM PQEAWMGTEF EPYGSDNSGL SMFFSPDFMK LGLYQLSPVE DLELGLLLMR   180
```

```
PGSLFINDLS KMKNFSDEGY GSVPRVFIVC KEDKAIPEER QRWMIDNFPV NLVMEMEETD     240
HMPMFCKPQQ LSDYFLKIAD KFV                                            263

SEQ ID NO: 14           moltype = AA  length = 263
FEATURE                 Location/Qualifiers
REGION                  1..263
                        note = gi[20]196998
source                  1..263
                        mol_type = protein
                        organism = Arabidopsis thaliana
SEQUENCE: 14
MSEEKRKQHF VLVHGSCHGA WCWYKVKPLL EAVGHRVTAV DLAASGIDTT RSITDIPTCE     60
QYSEPLTKLL TSLPNDEKVV LVGHSFGGLN LAIAMEKFPE KISVAVFLTA FMPDTEHSPS    120
FVLDKFGSNM PQEAWMGTEF EPYGSDNSGL SMFFSPDFMK LGLYQLSPVE DLELGLLLMR    180
PGSLFINDLS KMKNFSDEGY GSVPRVFIVC KEDKAIPEER QRWMIDNFPV NLVMEMEETD    240
HMPMFCKPQQ LSDYFLKIAD KFV                                            263

SEQ ID NO: 15           moltype = AA  length = 263
FEATURE                 Location/Qualifiers
REGION                  1..263
                        note = gi[27]754457
source                  1..263
                        mol_type = protein
                        organism = Arabidopsis thaliana
SEQUENCE: 15
MSEEKRKQHF VLVHGSCHGA WCWYKVKPLL EAVGHRVTAV DLAASGIDTT RSITDIPTCE     60
QYSEPLTKLL TSLPNDEKVV LVGHSFGGLN LAIAMEKFPK KISVAVFLTA FMPDTEHSPS    120
FVLDKFGSNM PQEAWMGTEF EPYGSDNSGL SMFFSPDFMK LGLYQLSPVE DLELGLLLMR    180
PGSLFINDLS KMKNFSDEGY GSVPRVFIVC KEDKAIPEER QRWMIDNFPV NLVMEMEETD    240
HMPMFCKPQQ LSDYFLKIAD KFV                                            263

SEQ ID NO: 16           moltype = AA  length = 257
FEATURE                 Location/Qualifiers
REGION                  1..257
                        note = gi[50]513520
source                  1..257
                        mol_type = protein
                        organism = Hevea brasiliensis
SEQUENCE: 16
MAFAHFVLIH TICHGAWIWH KLKPLLEALG HKVTALDLAA SGVDPRQIEE IGSFDEYSEP     60
LLTFLEALPP GEKVILVGES CGGLNIAIAA DKYCEKIAAA VFHNSVLPDT EHCPSYVVDK    120
LMEVFPDWKD TTYFTYTKDG KEITGLKLGF TLLRENLYTL CGPEEYELAK MLTRKGSLFQ    180
NILAKRPFFT KEGYGSIKKI YVWTDQDEIF LPEFQLWQIE NYKPDKVYKV EGGDHLLQLT    240
KTKEIAEILQ EVADTYN                                                   257

SEQ ID NO: 17           moltype = AA  length = 257
FEATURE                 Location/Qualifiers
REGION                  1..257
                        note = gi[64]35646
source                  1..257
                        mol_type = protein
                        organism = Hevea brasiliensis
SEQUENCE: 17
MAFAHFVLIH TICHGAWIWH KLKPLLEALG HKVTALDLAA SGVDPRQIEE IGSFDEYSEP     60
LLTFLEALPP GEKVILVGES CGGLNIAIAA DKYCEKIAAA VFHNSVLPDT EHCPSYVVDK    120
LMEVFPDWKD TTYFTYTKDG KEITGLKLGF TLLRENLYTL CGPEEYELAK MLTRKGSLFQ    180
NILAKRPFFT KEGYGSIKKI YVWTDQDEIF LPEFQLWQIE NYKPDKVYKV EGGDHKLQLT    240
KTKEIAEILQ EVADTYN                                                   257

SEQ ID NO: 18           moltype = AA  length = 258
FEATURE                 Location/Qualifiers
REGION                  1..258
                        note = gi[27]80225
source                  1..258
                        mol_type = protein
                        organism = Manihot esculenta
SEQUENCE: 18
MAVVDFVLIH TICHGAWIWY KLKPVLEAAG HKVTALDLAA SGVDPRQIEQ INSFDEYSEP     60
LLTFMESLPQ GEKVILVGES CGGLNIAIAA DKYPEKIAAA VFQNSLLPDT KHKPSYVVDK    120
LMEVFPDWKD TEYFEFSNSN GETITGMVLG LKLMRENLYT ICPPEDYELA KMLTRRGSLF    180
QSILAQREKF TEKGYGSIKK IYVWTGDDKI FLPEFQLWQI ENYKPDLVFR VMGGDHKLQL    240
TKTNEIAGIL QKVADIYA                                                  258

SEQ ID NO: 19           moltype = AA  length = 258
FEATURE                 Location/Qualifiers
REGION                  1..258
                        note = gi[53]830670
```

```
source                      1..258
                            mol_type = protein
                            organism = Catharanthus roseus
SEQUENCE: 19
MEVMKHFVTV HGVGHGAWVY YKLKPRIEAA GHRCTAVNLA ASGINEKKLE EVRSSIDYAA    60
PLLEVLDSVP ENEKVILVGH SGGGMTAAVG MEKFPNKISL AVFLNAIMPD TENRPSYVLE   120
EYTAKTPPEA WKDCQFSAYG DPPITSLVCG PEFISSTLYH LSPIEDHALG KILVRPGSLF   180
IEDLLKAEKF TEEGFGSVPR VYVIAAEDKT IPPEFQRWMI ENNPVKEVKE IKGADHMPMF   240
SKPDELSQCL LDIAKKHA                                                 258

SEQ ID NO: 20               moltype = AA  length = 264
FEATURE                     Location/Qualifiers
REGION                      1..264
                            note = gi[66]51393
source                      1..264
                            mol_type = protein
                            organism = Rauvolfia serpentina
SEQUENCE: 20
MHSAANAKQQ KHFVLVHGGC LGAWIWYKLK PLLESAGHKV TAVDLSAAGI NPRRLDEIHT    60
FRDYSEPLME VMASIPPDEK VVLLGHSFGG MSLGLAMETY PEKISVAVFM SAMMPDPNHS   120
LTYPFEKYNE KCPADMMLDS QFSTYGNPEN PGMSMILGPQ FMALKMFQNC SVEDLELAKM   180
LTRPGSLFFQ DLAKAKKFST ERYGSVKRAY IFCNEDKSFP VEFQKWFVES VGADKVKEIK   240
EADHMGMLSQ PREVCKCLLD ISDS                                          264

SEQ ID NO: 21               moltype = AA  length = 262
FEATURE                     Location/Qualifiers
REGION                      1..262
                            note = gi[41]814856
source                      1..262
                            mol_type = protein
                            organism = Lycopersicon esculentum
SEQUENCE: 21
MEKGDKNHFV LVHGACHGAW CWYKVVTILR SEGHKVSVLD MAASGINPKH VDDLNSMADY    60
NEPLMEFMNS LPQLERVVLV GHSMGGINIS LAMEKFPKQI VVAVFVTAFM PGPDLNLVAL   120
GQQYNQQVES HMDTEFVYNN GQDKAPTSLV LGPEVLATNF YQLSPPEDLT LATYLVRPVP   180
LFDESILLAN TTLSKEKYGS VHRVYVVCDK DNVLKEQQFQ KWLINNNPPD EVQIIHNADH   240
MVMFSKPRDL SSCLVMISQK YY                                            262

SEQ ID NO: 22               moltype = AA  length = 260
FEATURE                     Location/Qualifiers
REGION                      1..260
                            note = gi[40]549303
source                      1..260
                            mol_type = protein
                            organism = Nicotiana tabacum
SEQUENCE: 22
MKEGKHFVLV HGACHGGWSW YKLKPLLEAA GHKVTALDLA ASGTDLRKIE ELRTLYDYTL    60
PLMELMESLS ADEKVILVGH SLGGMNLGLA MEKYPQKIYA AVFLAAFMPD SVHNSSFVLE   120
QYNERTPAEN WLDTQFLPYG SPEEPLTSMF FGPKFLAHKL YQLCSPEDLA LASSLVRPSS   180
LFMEDLSKAK YFTDERFGSV KRVYIVCTED KGIPEEFQRW QIDNIGVTEA IEIKGADHMA   240
MLCEPQKLCA SLLEIAHKYN                                               260

SEQ ID NO: 23               moltype = AA  length = 262
FEATURE                     Location/Qualifiers
REGION                      1..262
                            note = gi[56]392765
source                      1..262
                            mol_type = protein
                            organism = Solanum tuberosum
SEQUENCE: 23
MEKGNKNHFV LVHGACHGAW CWYKVVTILR SEGHKVSVLD MAASGINPKH VEDLNSMADY    60
NEPLMEFMNS LPQQERVVLV GHSMGGINIS LAMEKFPHKI AVAVFVSASM PGPDLNLVAV   120
TQQYSQQVET PMDTEFVYNN GLDKGPTSVV LGPKVLATIY YQFSPPEDLT LATYLVRPVP   180
LFDESVLLTN TTLSKEKYGS VHRVYVVCDK DKVLKEEQFQ RWLIKNNPPN EVQMIHDAGH   240
MVMFSKPREL CSCLVMISQK YH                                            262

SEQ ID NO: 24               moltype = AA  length = 266
FEATURE                     Location/Qualifiers
REGION                      1..266
                            note = CeresClone:644331
source                      1..266
                            mol_type = protein
                            organism = Triticum aestivum
SEQUENCE: 24
MEACAGQASS AHIVLVHGAC LGGWSWFKVA TRLRSAGHRV STPDLAASGV DPRPLREVPT    60
FRDYTKPLLD LLESLPSGEK VVLVGHSLGG VNVALACELF PEKIAAAVFV AAFMPDHRSP   120
PSYVLEKFVE GRTLDWMDTE FKPQDPEGKL PTSMLFGPLV TRAKFFQLCS PEDLTLGRSL   180
MRVNSMFVDD LRLQPPHTEA RYGSVRKAYV VFKDDHAIVE QFQRWMVHNY PVDEVMEIDG   240
ADHMALLSTP TELARCLADI AVKYAA                                        266
```

```
SEQ ID NO: 25              moltype = AA  length = 265
FEATURE                    Location/Qualifiers
REGION                     1..265
                           note = CeresClone:936068
source                     1..265
                           mol_type = protein
                           organism = Triticum aestivum
SEQUENCE: 25
MEGSSSGKHF ILIHGLCHGA WCWYKLVPML RAAGHRVTAL DMAASGAHPA RMDEVPSFED      60
YSWPLLDAVA AAPAGERLVL VGHSLGGLNI ALAMERFPRK VAAAVFLAAC MPCVGRHMGA    120
TTEEIMRRIK PDFFMDMKRM VLNTSQGPRP ALVFGPKILA AKLYDRSSGE DQTLATMLVR    180
PGCQFLDDPT MKDEALLTEA KYGSVKKVYV VAMADASNSE EMQRWMVDMS PGTEAEEIAG    240
ADHMAMCSKP RELCDVLLRI ADKYE                                          265

SEQ ID NO: 26              moltype = AA  length = 268
FEATURE                    Location/Qualifiers
REGION                     1..268
                           note = gi[34]907176
source                     1..268
                           mol_type = protein
                           note = Oryza sativa subsp. japonica
                           organism = Oryza sativa
SEQUENCE: 26
MEISSSSKKH FILVHGLCHG AWCWYRVVAA LRAAGHRATA LDMAASGAHP ARVDEVGTFE      60
EYSRPLLDAV AAAAAPGERL VLVGHSHGGL SVALAMERFP DKVAAAVFVA AAMPCVGKHM    120
GVPTEEFMRR TAPEGLLMDC EMVAINNSQG SGVAINLGPT FLAQKYYQQS PAEDLALAKM    180
LVRPGNQFMD DPVMKDESLL TNGNYGSVKK VYVIAKADSS STEEMQRWMV AMSPGTDVEE    240
IAGADHAVMN SKPRELCDIL IKIANKYE                                       268

SEQ ID NO: 27              moltype = AA  length = 262
FEATURE                    Location/Qualifiers
REGION                     1..262
                           note = gi[57]899620
source                     1..262
                           mol_type = protein
                           note = Oryza sativa (japonica cultivar-group)
                           organism = Oryza sativa
SEQUENCE: 27
MEGSSSSKH FILVHGLCHG AWCWYKVVTM LRSEGHRVTA LDLAASGVHP ARVDEVHSFE       60
EYSQPLLDAV AEAPAGERLI LVGHSFGGLS IALAMERFPE KIAVAVFVAA AVPCVGKRII    120
PELIREKAPK DMLLDSKMIP INNKQGPGTA ILLGPNFLAE KGYPLSPAED LTLAKLLVRP    180
TSQFVDDPTM KDDRLLTSAN YGSVKRVCLM AMEDDLKEVH RYMITLSPGV EVEEIAGADH    240
AVMCSRPREL SDLLAKIGSK YD                                             262

SEQ ID NO: 28              moltype = AA  length = 265
FEATURE                    Location/Qualifiers
REGION                     1..265
                           note = gi[15]866583
source                     1..265
                           mol_type = protein
                           organism = Capsella rubella
SEQUENCE: 28
MGGDGGAEQP VIHFVFVHGA SHGAWCWYKL TSLLETAGFK TTSVDLTGAG ISVTDSNTVL      60
ESDQYNRPLF SLLSDLPPSH KVILVGHSIG GGSVTDALCR FTDKISMAIY LAASMVKPGS    120
VPSPHVSDMH ADAREENIWE YTYGEGTDKP PTGVIMKQEF LRQYYYSQSP LEDVSLATKL    180
LRPAPMRAFQ DLDKSPPNPE VEKVPRVYIK TGKDNLFSSV RQDLLVKNWP PSQFYVLEES    240
DHSAFFSVPT TLFVYLLRAV SFLHK                                          265

SEQ ID NO: 29              moltype = AA  length = 265
FEATURE                    Location/Qualifiers
REGION                     1..265
                           note = gi[56]393011
VARIANT                    46
                           note = Xaa can be any naturally occurring amino acid
source                     1..265
                           mol_type = protein
                           note = Lycopersicon hirsutum f. glabratum
                           organism = Lycopersicon hirsutum
SEQUENCE: 29
MEKSMSPFVK KHFVLVHTAF HGAWCWYKIV ALMRSSGHNV TALDLXASGI NPKQALQIPN      60
FSDYLSPLME FMASLPANEK IILVGHALGG LAISKAMETF PEKISVAVFL SGLMPGPNID    120
ATTVCTKAGS AVLGQLDNCV TYENGPTNPP TTLIAGPKFL ATNVYHLSPI EDLALATALV    180
RPLYLYLAED ISKEVVLSSK RYGSVKRVFI VATENDALKK EFLKLMIEKN PPDEVKEIEG    240
SDHVTMMSKP QQLFTTLLSI ANKYK                                          265
```

```
SEQ ID NO: 30           moltype = DNA  length = 412
FEATURE                 Location/Qualifiers
misc_feature            1..412
                        note = clone34419_inplanta_experimental_L21
source                  1..412
                        mol_type = other DNA
                        organism = Arabidopsis thaliana
SEQUENCE: 30
aacaacgcca caatcatggc tttgttctta tctcctaaaa ccatcactct tctcttcttc    60
tccctctccc tcgcactcta ctgcagcatc gatcctttcc acactgcgcc atttccgatt   120
tccccaattt cgtctctcac gaagttatct ctccacgtcc cgacgaagtt ccatgggaga   180
gagattcaca aaattcactt cagaaatcaa agattctgtt ttttaaccaa atccaaggtc   240
cagagagcgt cgcctttgat tctctcggac gtggtccgta caggcgttg ctgatggtag    300
ggttttgttt tgggatggag agaaatggat tgatttcgct tatacttcga gtaatcgatc   360
ggagatttgt gatccgaagt ataagcgaaa tcaatccatt tctctccatc cc           412

SEQ ID NO: 31           moltype = AA  length = 92
FEATURE                 Location/Qualifiers
REGION                  1..92
                        note = peptide_clone34419_inplanta_experimental_L21
source                  1..92
                        mol_type = protein
                        organism = Arabidopsis thaliana
SEQUENCE: 31
MALFLSPKTI TLLFFSLSLA LYCSIDPFHT APFPISPISS LTKLSLHVPT KFHGREIHKI    60
HFRNQRFCFL TKSKVQRASP LILSDVVRTR RC                                   92

SEQ ID NO: 32           moltype = DNA  length = 1776
FEATURE                 Location/Qualifiers
misc_feature            1..1776
                        note = cDNA12659859_inplanta_experimental_L22
source                  1..1776
                        mol_type = other DNA
                        organism = Arabidopsis thaliana
SEQUENCE: 32
gagcagaaga acttacttat agaaaaaaat gggaatttca aaaccactcc ttctattttc    60
gattttagtc ctctattttt cactctacac cattacacca acttcttcat tagcctccct   120
ccaagatcaa ttcatcaact gtgtccaaag aaacacacat gtttacttcc cacttgagaa   180
aacgttcttt gctcctacaa aaaatgtctc tatgttcagc caagttcttg aatcgacggc   240
tcaaaatctc cggttcttga aaaaatccat gcctaaaccg ggattcatat tcagccctat   300
tcacgagtct cacgtacaag cttccatcat ttgttccaag aaactccgaa tgcatctccg   360
tgtcagaagc ggcggtcacg actacgaagg cttgtctcta gtctctcaga tcgataaacc   420
gtttatattg atggatctgt caaagatgag acaggtcaac attaatattc aagcaaacag   480
tgcttgggtt caatctggtg ccactgttgg tgaactttat tacaggattg cggagaagag   540
caaagtccca gggttcccgg cgggtttgtg ctcgagctta ggcataggag gacacataac   600
aggcgttgcg tacggttcca tgatgcgaa atatgcttta ggtgcagaca atgttctaga   660
cgcaaagatt gttgatgcca acggtaaatt actcgataga gccgcgatgg gtgaggatac   720
atttgggct attagaggag gcgctggagg gagtttgg ataattctag catgaaagat    780
caagcttgtt cctgttccta agaccgtgac cgtctttacc gtcaccaaaa cgttacaaca   840
agacgtgggt aacaagatta tctcaaagtg gcaaagagtt gcggacaagc ttgttgaaga   900
gctattcatc agagtgctct tcaacgtagc tggaaccggt gggaacaaga ctgtgacgac   960
gtcgtacaat gctctgtttc ttggcgggaa aggaacgctg atgaacgtta tgaagaagag  1020
tttcccgag ctagggctaa catttaaaga ttgtatcgaa atgagctggc ttgaatccat   1080
tgcttacatt tctggattcc cgacccacac gcctactaca gtttttgcttc aagggaagtc  1140
tccgttccca aaggtcagct tcaaagccaa atcggatttc gtgaaaaccc cgattccga    1200
atccgggctt caagggatct tcaagaagct acttaaagaa gatattccat tgatgatatg   1260
gaatccttac ggaggaatga tggcgaaaat ccccgaatcc caaatccctt tccgcatcg    1320
aaaaggagtc ctcttcaagg ttcagtacgt aacaagttgg ctagacagtg acaagagacc   1380
gagcagacac atcaactgga tcagagatct ctatagttac atgacgcctt atgtctcaag   1440
taacccacga gaagcttacg tgaactaccg tgatttagac ctgggaagga acacgaaaga   1500
cgtgaaaaca tgcatcaaac aagctcaagt ctggggagct aactacttca aaaacaattt   1560
caacagattg atgatgatta aagcaaaggt tgatccagag aacttcttta gacacgagca   1620
gagcattcca cctatgatgt aacgaggtca atcaaataag aataaattag aagaaaatca   1680
gataatggtt cttctgtatt tcggaaaaat gttattctag ctatgcttgt agtagtacta   1740
tgtttcacct aaaattcgat atgttgcttc ttagta                             1776

SEQ ID NO: 33           moltype = AA  length = 537
FEATURE                 Location/Qualifiers
REGION                  1..537
                        note = peptide_cDNA12659859_inplanta_experimental_L22
source                  1..537
                        mol_type = protein
                        organism = Arabidopsis thaliana
SEQUENCE: 33
MGISKPLLLF SILVLYFSLY TITPTSSLAS LQDQFINCVQ RNTHVYFPLE KTFFAPTKNV    60
SMFSQVLEST AQNLRFLKKS MPKPGFIFSP IHESHVQASI ICSKKLRMHL RVRSGGHDYE   120
GLSYVSQIDK PFILMDLSKM RQVNINIQDN SAWVQSGATV GELYYRIAEK SKVHGFPAGL   180
CSSLGIGGHI TGGAYGSMMR KYGLGADNVL DAKIVDANGK LLDRAAMGED TFWAIRGGAG   240
```

```
GSFGIILAWK IKLVPVPKTV TVFTVTKTLQ QDVGNKIISK WQRVADKLVE ELFIRVLFNV   300
AGTGGNKTVT TSYNALFLGG KGTLMNVMKK SFPELGLTFK DCIEMSWLES IAYISGFPTH   360
TPTNVLLQGK SPFPKVSFKA KSDFVKTPIP ESGLQGIFKK LLKEDIPLMI WNPYGGMMAK   420
IPESQIPFPH RKGVLFKVQY VTSWLDSDKR PSRHINWIRD LYSYMTPYVS SNPREAYVNY   480
RDLDLGRNTK DVKTCIKQAQ VWGANYFKNN FNRLMMIKAK VDPENFFRHE QSIPPMM     537

SEQ ID NO: 34              moltype = AA   length = 543
FEATURE                    Location/Qualifiers
REGION                     1..543
                           note = CeresClone:522974
source                     1..543
                           mol_type = protein
                           organism = Glycine max
SEQUENCE: 34
NTRESRNQRT MKSLRSILAT FVVLLSISLT ISLPIEEAFN HCLTQHSQTP NQFPSSIYTY    60
TNGSFTSILE STAQNLRYLL PSVPKPDFIF TPLDDSQVQA AVVCAKKLGI HMRVRSGGHD   120
YEGLSYVSLI EKPFMILDLA KLRAVNVDIA RNTAWIQAGA TIGEVYYRIS EKSAVHGFPA   180
GLCTTLGIGG HITGGAYGSM MRKYGLGADN VLDARIVDAN GKVLDRKAMG EDLFWAIRGG   240
GGGSFGVILW WKIKLVPVPQ TVTVFTVTKT LEQGGSKLLH RWQQVAPHID ENLFIRVIIQ   300
PGNGTVPGKR TVTTSYNALF LGGANRLLQV MKHGFPELGL TRKDCVETSW IESVLYIAGY   360
PDGTAPEVLL QGKSTTKAYF KAKSDFVREV ITEKSLNALW KIFLQDDGPL MIWNPYGGKM   420
SRIAESATPF PHRKGVLYKI QHVTGWLDGE KSMAKHMNWM RKFYFYMAPY VSKYPRETYV   480
NYRDLDIGMN QKNNTSLLKA SSWGYRYFKG NFNRLVKVKT KVDPSNFFRH EQSIPLLPTG   540
KKE                                                                543

SEQ ID NO: 35              moltype = AA   length = 538
FEATURE                    Location/Qualifiers
REGION                     1..538
                           note = CeresClone:561310
source                     1..538
                           mol_type = protein
                           organism = Glycine max
SEQUENCE: 35
TETREIIVNM ELSYCAVFLI LLIPISRADA TSVEKQFKEC LLTQLDGNSE HIEKITFTSS    60
STLYPQVWDS LAQNPRWVNI SSRKPLMILT PPHESEIQAA ILCSKELKLQ LRVRSGGHDY   120
EGLSYLSDVP FVMVDLINIR SIEINLADET AWVQAGASIG ELYYKISKAS KVHGFPAGTC   180
PSVGIGGHIS GGGQGLMLRK HGLAADNVVD AYLIDANGKI HDRKSMGEDV FWAIRGGDAS   240
SFGVILAWKI KLVRVPPIVT GFNVPRTPEE GVTDLIHRWQ YIAHDLHEDL VIRVIAQISG   300
HDKSKKFRAT FNSIFLGGVD RLIPLMNESF PELGLQAKDC TEMSWIQSVM FIAGYNIEDP   360
LELLLNRTTM FKRSFKAKSD FFKEPVPKSG LEGAWKLLLE EEIAFLIMEP YGGRMNEISE   420
SEIPFPHRKG NLYNLQYLVN WEVNSDEASR RHLQWAKMVY KYMTPYVSKS PRAAYFNYKD   480
LDLGKNKLDS TSYSEASVWG KKYFKGNFRR LAQIKTKFDP LNFFRNEQSI PLLNSHHS    538

SEQ ID NO: 36              moltype = AA   length = 535
FEATURE                    Location/Qualifiers
REGION                     1..535
                           note = gi[13]161397
source                     1..535
                           mol_type = protein
                           organism = Vigna unguiculata
SEQUENCE: 36
MKTLSCYYTF ATVIALLFSF TPSSADTHEN FLQCLYSYPH NTNSISSVLY TQTNSSYFSV    60
LDATMQNLRF SDSRKPLVIV TPQVVSHIQA TIKCSQRHGL QIRTRSGGHD YEGLSYVARV   120
PFVILDLLNF REIKVDVENR TAWVQVGATL GELYYTISQA SKTLGFPAGV CYSVGAGGHI   180
SGGGYGFLMR KYGLAADNVI DAHIIDVNGN LLDRKAMGED LFWAIRGGGG ASFGVIVSWK   240
IKLVPVPSTV TVFNVERILE ENATEIIEKW QLVANKLDER IFLRMDLARA NSSQHGKLAL   300
QANFVAMFQG GVEELIPLMQ KNFPELGLKR KDCTETSWIG SAVFTNGALI GSSGHEAPEV   360
LLNRTQIRSG KYKGKSDYVR KPIPVDGLRG LWRWLNDDKV QYSQLQFAPY GGKMDNISES   420
EIPFAHRSGY IFHIHYVVVW QEEGDEATQR HVNWIRRLYK YMEPYVSNSP RAAYVNYRDL   480
DIGVNNNGYT SYHQASIWGL KYFSNNFKRL ATVKTKVDPH NFFRNEQSIP TLSKE       535

SEQ ID NO: 37              moltype = AA   length = 538
FEATURE                    Location/Qualifiers
REGION                     1..538
                           note = gi[18]652400
source                     1..538
                           mol_type = protein
                           organism = Helianthus annuus
SEQUENCE: 37
MANITSSFNM QTSILTLLLL LLSTQSSATS RSITDRFIQC LHDRADPSFP ITGEVYTPGN    60
SSFPTVLQNY IRNLRFNETT TPKPFLIITA EHVSHIQAAV VCGKQNRLLL KTRSGGHDYE   120
GLSYLTNTNQ PFFIVDMFNL RSINVDIEQE TAWVQAGATL GEVYYRIAEK SNKHGFPAGV   180
CPTVGVGGHF SGGGYGNLMR KYGLSVDNIV DAQIIDVNGK LLDRKSMGED LFWAITGGGG   240
VSFGVVLAYK IKLVRVPEVV TVFTIERREE QNLSTIAERW VQLVADKLDR LFLRMTFSVI   300
NDTNGGKTVR AIFPTLYLGN SRNLVTTLNK DFPELGLQES DCTEMSWVES VLYYTGFPSG   360
TPTTALLSRT PQRLNPFKIK SDYVQNPISK RQFEFIFERM KELENQMLAF NPYGGRMSEI   420
SEFAKPFPHR SGNIAKIQYE VNWEDLSDEA ENRYLNFTRL MYDYMTPFVS KNPREAFLNY   480
RDLDIGINSH GRNAYTEGMV YGHKYFKETN YKRLVSVKTK VDPDNFFRNE QSIPTLSS    538
```

```
SEQ ID NO: 38             moltype = AA   length = 522
FEATURE                   Location/Qualifiers
REGION                    1..522
                          note = gi[41]393750
source                    1..522
                          mol_type = protein
                          organism = Cynodon dactylon
SEQUENCE: 38
MARSRAFAFA LLICAVAASC HVALSAPPPY AKQVERDFLT CLTKDIPPRQ LYAKSSPAYA   60
SVWSSTVRNI KFLSDKTVKP LYIITPTNAS HIQAAVVCGR RHGMRIRVRS GGHDYEGLSY  120
RSEKPEPFAV VDMNKMRAVS IDGKAATAWV DSGAQLGDLY YGIAKASPKL GFPAGVCTTI  180
GVGGHFSGGG FGMLLRKYGT AADNVIDAKV VDAQGRLLDR KAMGEDHFWA IRGGGGESFG  240
IVASWQVKLL PVPPKVTVFQ VHKGIKEGAI DLVTKWQTVA PALPDDLMIR IMAMGQGAMF  300
EALYLGTCKD LVLLMTARFP ELGMNATHCK EMTWIESVPY IPMGPKGTVR DLLNRTSNIK  360
AFGKYKSDYV LEPIPKSDWE KIFTWLVKPG AGVMIMDPYG GGIASVPESA TPFPRRSGVL  420
FNIQYVVYWF GEGAAALPTQ WTRDIYDFMT PYVSKNPRQA YVNYRDLDLG VNQVVGNVST  480
YASGKVWGEK YFKGNFERLA RTKGKIDPED YFRNEQSIPP LL                    522

SEQ ID NO: 39             moltype = AA   length = 540
FEATURE                   Location/Qualifiers
REGION                    1..540
                          note = gi[18]652398
source                    1..540
                          mol_type = protein
                          organism = Lactuca sativa
SEQUENCE: 39
MAITYSFNFK SYIFPLLLVL LSTHSSATST SIIDRFTQCL NNRADPSFPL SGQLYTPDNS   60
SFPSVLQAYI RNLRFNESTT PKPILIITAL HPSIQAAVV CAKTHRLLMK TRSGGHDYEG  120
LSYVTNSNQP FFVVDMFNLR SINVSIEDET AWVQAGATLG EVYYRIAEKS NSHAFPAGVC  180
PTVGVGGHFS GGGYGNLMGK YGLSVDNIVD AQLIDVNGKL LNRKSMGEDL FWAITGGGGV  240
SFGVVVAYKI KLVRVPTTVT VFNVQRTSEQ NLSTIAHRWI QVADKLDNDL FLRMTFNVIN  300
NTNGEKTIRG LFPTLYLGNS TALVALLNKD FPELGVEISD CIEMSWIESV LFYTNFPIGT  360
PTTALLSRTP QRLNPFKIKS DYVKNTISKQ GFESIFERMK ELENQMLAFN PYGGRMSEIS  420
EFAKPFPHRS GNIAKIQYEV NWDELGVEAA NRYLNFTRVM YDMTPFVSK NPREAFLNYR  480
DLDIGVNSHG KNAYGEGMVY GHKYFKETNY KRLTMVKTRV DPSNFFRNEQ SIPTLSSSWK  540

SEQ ID NO: 40             moltype = AA   length = 545
FEATURE                   Location/Qualifiers
REGION                    1..545
                          note = gi[26]005814
source                    1..545
                          mol_type = protein
                          organism = Cannabis sativa
SEQUENCE: 40
MNCSAFSFWF VCKIIFFFLS FHIQISIANP RENFLKCFSK HIPNNVANPK LVYTQHDQLY   60
MSILNSTIQN LRFISDTTPK PLVIVTPSNN SHIQATILCS KKVGLQIRTR SGGHDAEGMS  120
YISQVPFVVV DLRNMHSIKI DVHSQTAWVE AGATLGEVYY WINEKNENLS FPGGYCPTVG  180
VGGHFSGGGY GALMRNYGLA ADNIIDAHLV NVDGKVLDRK SMGEDLFWAI RGGGGENFGI  240
IAAWKIKLVA VPSKSTIFSV KKNMEIHGLV KLFNKWQNIA YKYDKDLVLM THFITKNITD  300
NHGKNKTTVH GYFSSIFHGG VDSLVDLMNK SFPELGIKKT DCKEFSWIDT TIFYSGVVNF  360
NTANFKKEIL LDRSAGKKTA FSIKLDYVKK PIPETAMVIL LEKLYEEDVG AGMYVLYPYG  420
GIMEEISESA IPFPHRAGIM YELWYTASWE KQEDNEKHIN WVRSVYNFTT PYVSQNPRLA  480
YLNYRDLDLG KTNHASPNNY TQARIWGEKY FGKNFNRLVK VKTKVDPNNF FRNEQSIPPL  540
PPHHH                                                              545

SEQ ID NO: 41             moltype = AA   length = 535
FEATURE                   Location/Qualifiers
REGION                    1..535
                          note = gi[53]792953
source                    1..535
                          mol_type = protein
                          note = Oryza sativa subsp. japonica
                          organism = Oryza sativa
SEQUENCE: 41
MSTTPTAASR RLVLILCTLA ISCSSGIAGF AAGDDDAFIR CLAAAAVPPR LVHTPGSASY   60
APTLVSSIRN LRFVTPGTPR PLAIVAAAEA GHAQAAVRCG RRHGVRVRAR SGGHDYEGLS  120
YLSLDRRERF AVLDLAALRD VRVDADRAEA WVGSGATLGE LYYAVGAASR TLAFPAGVCP  180
TVGVGGHISG GGFGTLMRRY GLAADNVLDA VLVDADGRLL NRTTMGEGLF WAIRGGGGES  240
FGVVLSWKLR LVRVPETVTV FTIRRPRNQS ATDLITKWQE ISPSLPRDVI LRVVVQSQHA  300
QFESLFLGRC RRLARLMRAR FPELGMTQSD CEEITWIQST VYFAFYSSSK PLELLLDRGT  360
EPDRYFKAKS DYVQEPIPRH AWESTWPWLE EHDAGLLILD PYGGEMARVS PAATPFPHRK  420
GNLYNLQYYS FWFEHGAETL ERHLSWVRGL YGEMEPYVSK NPRTGYVNYR DMDLGRNEIE  480
GNVTSYTKGK VWGEKYFRGN FERLAAVKAM VDPDDFFRNE QSIPPLPAAK GWSSI       535

SEQ ID NO: 42             moltype = AA   length = 542
FEATURE                   Location/Qualifiers
REGION                    1..542
                          note = gi[20]563190
```

| | | |
|---|---|---|
| source | 1..542 | |
| | mol_type = protein | |
| | organism = Helianthus annuus | |
| SEQUENCE: 42 | | |

```
MNNSRSVFLL VLALSFCVSF GALSSIFDVT STSEDFITCL QSNSNNVTTI SQLVFTPANT    60
SYIPIWQAAA DPIRFNKSYI PKPSVIVTPT DETQIQTALL CAKKHGYEFR IRDGGHDFEG   120
NSYTANAPFV MLDLVNMRAI EINVENRTAL VQGGALLGEL YYTISQKTDT LYFPAGIWAG   180
VGVSGFLSGG GYGNLLRKYG LGADNVLDIR FMDVNGNILD RKSMGEDLFW ALRGGGASSF   240
GIVLQWKLNL VPVPERVTLF SVSYTLEQGA TDIFHKYQVL LPKFDRDLLI RVQLNTEYIG   300
NTTQKTVRIL FHGIYQGNID TLLPLLNQSF PELNVTREVC QEVRMVQTTL EFGGFNISTP   360
TSVLANRSAI PKLSFKGKSD YVRTPIPRSG LRKLWRKMFE NDNSQTLFMY TFGGKMEEYS   420
DTAIPYPHRA GVLYQVFKRV DFVDQPSDKT LISLRRLAWL RSFDKTLEPY VTSNPREAYM   480
NYNDLDLGFD SAAYEEASEW GERYWKRENF KKLIRIKAKV DPENFFRHPQ SIPVFSRPLS   540
DM                                                                 542
```

| | | |
|---|---|---|
| SEQ ID NO: 43 | moltype = DNA  length = 1174 | |
| FEATURE | Location/Qualifiers | |
| misc_feature | 1..1174 | |
| | note = cDNA12723147_L23 | |
| source | 1..1174 | |
| | mol_type = other DNA | |
| | organism = Arabidopsis thaliana | |
| SEQUENCE: 43 | | |

```
agtggctact gagtaaagct ttgggccacc gagagaaacc attttctgag agcacacttt    60
cgttgacttc tctttaacca atgtctttaa ccacagtccc tacgctcgcc atcagatccg   120
gaccatccgg tcatcactcg atgccggttc ttggttttgg aaccgccgct tctccgctac   180
cggaaccaac gatgctgaaa gagacggtga ttgaggctat taagcttggt tatcgccatt   240
tcgacacctc tccaaggtac caaacggagg agccgatcgg cgaagcttta gcggaggcgg   300
tttcactcgg cttagttcga tctcgatctg aattctttgt cactaccaaa ctttggtgtg   360
ctgatgctca tggtggtctc gtcgtaccgg cgatcaaacg gagtttgaaa aaccttaaac   420
tggactatct tgatctttat ataattcatt ggccggttag ctcgaaacct ggtaaataca   480
agtttcctat tgatgaagat gattttatgc caatggattt cgaagtagtg tggtctgaaa   540
tggaggagtg tcagagactt gggctcgcaa aatgcatagg agtaagcaat ttttcatgta   600
agaagcttca acacatactc tctatcgcga caatcccgcc tagcgtcaat caagttgaga   660
tgagtccaat atggcaacaa agaaagctaa gggagctttg tagatcgaac gacattgttg   720
tcacagcgta ctcggtgttg ggatctagag gagcttttg gggaactccc aaaattatgg   780
aatctgatgt tctcaaagaa atagcagaag caaggaaaa aacagtggcc caggtgagta   840
tgagatgggc ttatgaacaa ggagtgagca tggtagtgaa gagctttacc aaagagagat   900
tagaagagaa tctaaagata tttgattggt ctttgacaga ggatgagaca cagagaattt   960
caactgagat tcctcagttc agaaacgtcc acggagaggt ttatacctct aagaaaggtc  1020
ccatcaaatc tgtcgccgag atgtgggacg gggagatctg atcactttgt gtgaaaatag  1080
cctattgaaa acgcacaat tatcattcgt cacaatgatt tcttgtcat tctctctaat  1140
aatgaaataa tgaataatga ataaggacta tctc                              1174
```

| | | |
|---|---|---|
| SEQ ID NO: 44 | moltype = AA  length = 326 | |
| FEATURE | Location/Qualifiers | |
| REGION | 1..326 | |
| | note = peptide_cDNA12723147_L23 | |
| source | 1..326 | |
| | mol_type = protein | |
| | organism = Arabidopsis thaliana | |
| SEQUENCE: 44 | | |

```
MSLTTVPTLA IRSGPSGHHS MPVLGFGTAA SPLPEPTMLK ETVIEAIKLG YRHFDTSPRY    60
QTEEPIGEAL AEAVSLGLVR SRSEFFVTTK LWCADAHGGL VVPAIKRSLK NLKLDYLDLY   120
IIHWPVSSKP GKYKFPIDED DFMPMDFEVV WSEMEECQRL GLAKCIGVSN FSCKKLQHIL   180
SIATIPPSVN QVEMSPIWQQ RKLRELCRSN DIVVTAYSVL GSRGAFWGTP KIMESDVLKE   240
IAEAKEKTVA QVSMRWAYEQ GVSMVVKSFT KERLEENLKI FDWSLTEDET QRISTEIPQF   300
RNVHGEVYTS KKGPIKSVAE MWDGEI                                        326
```

| | | |
|---|---|---|
| SEQ ID NO: 45 | moltype = AA  length = 321 | |
| FEATURE | Location/Qualifiers | |
| REGION | 1..321 | |
| | note = gi[64]78216 | |
| source | 1..321 | |
| | mol_type = protein | |
| | organism = Papaver somniferum | |
| SEQUENCE: 45 | | |

```
MEIGGVPVVT LSSGRGMPIL GMGTAENNLQ GSERVKLAIL KAIEVGYRHF DTAFVYQTEG    60
SLGEAVAEAL QNGLIKSRDE LFITSKLWCA DAYPDHVLPA LQNSLRNLKL EYLDLYIHW   120
PVSLKPGKFV HPIPKDEIFP IDYKSVWAAM EKCQMLGLTK SIGVSNFSCK KLHYLMATAN   180
IPPAVNQVEM NPIWQQQKLR DYCKTNNIMV TAYSPLGAKG TMWGSSGVMD SEVLNQISQV   240
RGKSVAQVSL RWVYEQGASL LVKSFNEERM KENLKIFDWE LSPEDLKNIS ELPQRRVSTG   300
DPFVSINGPF KSVEELWDDE V                                             321
```

| | | |
|---|---|---|
| SEQ ID NO: 46 | moltype = AA  length = 327 | |
| FEATURE | Location/Qualifiers | |
| REGION | 1..327 | |
| | note = gi[50]80825 | |

```
source                          1..327
                                mol_type = protein
                                organism = Arabidopsis thaliana
SEQUENCE: 46
MVASGHEVVT LTFPIGSVHH LMPVLALGTA ASPPPEPIVL KRTVLEAIKL GYRHFDTSPR    60
YQTEEPLGEA LAEAVSLGLI QSRSELFVTS KLWCADAHGG LVVPAIQRSL ETLKLDYLDL   120
YLIHWPVSSK PGKYKFPIEE DDFLPMDYET VWSEMEECQR LGVAKCIGVS NFSCKKLQHI   180
LSIAKIPPSV NQVEMSPVWQ QRKLRELCKS KGIVVTAYSV LGSRGAFWGT HKIMESDVLK   240
EIAEAKGKTV AQVSMRWAYE EGVSMVVKSF RKDRLEENLK IFDWSLTEEE KQRISTEISQ   300
SRIVDGEVYI SEKGPIKSVT EMWDGEI                                      327

SEQ ID NO: 47                   moltype = AA  length = 320
FEATURE                         Location/Qualifiers
REGION                          1..320
                                note = gi[15]218958
source                          1..320
                                mol_type = protein
                                organism = Arabidopsis thaliana
SEQUENCE: 47
MSALTFPIGS VHHLMPVLAL GTAASPPPEP IVLKRTVLEA IKLGYRHFDT SPRYQTEEPL    60
GEALAEAVSL GLIQSRSELF VTSKLWCADA HGGLVVPAIQ RSLETLKLDY LDLYLIHWPV   120
SSKPGKYKFP IEEDDFLPMD YETVWSEMEE CQRLGVAKCI GVSNFSCKKL QHILSIAKIP   180
PSVNQVEMSP VWQQRKLREL CKSKGIVVTA YSVLGSRGAF WGTHKIMESD VLKEIAEAKG   240
KTVAQVSMRW AYEEGVSMVV KSFRKDRLEE NLKIFDWSLT EEEKQRISTE ISQSRIVDGE   300
VYISEKGPIK SVTEMWDGEI                                              320

SEQ ID NO: 48                   moltype = AA  length = 323
FEATURE                         Location/Qualifiers
REGION                          1..323
                                note = gi[53]988164
source                          1..323
                                mol_type = protein
                                note = Fragaria x ananassa
                                organism = unidentified
SEQUENCE: 48
MTATQIPEVV LESSNGRRTM PVLGFGTASN NLQPEVLIEA VLEAIKLGYR HFDTASIYGS    60
EQTLGVAIAQ ALKLGLVASR DELFITSKLW PNDGHPNLVI PALKKSLQNL ELEYLDLYLI   120
HWPISAKPGK LSHALEEKDQ MPMDFKGVWA DMEEAQRLGL TKSIGISNFS TKKTQNLLSF   180
ATIPPSVNQV EMSPFWQQKK LRDFCKASGI VVTAFSPLGA IGTSWGTNHV LESKVLNEIA   240
EAHGKTVAQV CIRWVYQVGA TLAVKSYNKE RLKQNVQVFD WELTEEDLEK INQIPQRKMM   300
PREELVTATG PYKSLDDLWD GEY                                          323

SEQ ID NO: 49                   moltype = AA  length = 319
FEATURE                         Location/Qualifiers
REGION                          1..319
                                note = gi[27]92295
source                          1..319
                                mol_type = protein
                                note = Fragaria x ananassa
                                organism = unidentified
SEQUENCE: 49
MAKVPSVTLS SCGDDIQTMP VIGMGTSSYP RADPETAKAA ILEAIRAGYR HFDTAAAYGS    60
EKDLGEAIAE ALRLQLIKSR DELFITTKLW ASFAEKDLVL PSIKASLSNL QVEYIDMYII   120
HWPFKLGKEV RTMPVERDLV QPLDIKSVWE AMEECKKLGL ARGIGVSNFT SSMLEELLSF   180
AEIPPAVNQL EMNPAWQLKK LRDFCKAKGI HVTAYSPLGA ARTKWGDDRV LGSDIIEEIA   240
QAKGKSTAQI SLRWVYEQGV SIVTKSYNKE RMRQNLDIFD FCLTEEELEK MSHLPQRKGV   300
TFASILGPHD IVLEVDEEL                                               319

SEQ ID NO: 50                   moltype = AA  length = 319
FEATURE                         Location/Qualifiers
REGION                          1..319
                                note = gi[50]380153
source                          1..319
                                mol_type = protein
                                note = Fragaria x ananassa
                                organism = unidentified
SEQUENCE: 50
MAKVPSVTLS SCGDDIQTMP VIGMGTSSYP RADPETAKAA ILEAIRAGYR HFDTAAAYGS    60
EKDLGEAIAE ALRLQLIKSR DELFITTKLW ASFAEKDLVL PSIKASLSNL QVEYIDMYII   120
HWPFKLGKEV RTMPVERDLV QPLDIKSVWE AMEECKKLGL ARGIGVSNFT SSMLEELLSF   180
AEIPPAVNQL EMNPAWQLKK LRDFCKAKGI HVTAYSPLGA ARTKWGDDRV LGSDIIEEIA   240
QAKGKSTAQI SLRWVYEQGV SIVTKSYNKE RMRQNLDIFD FCLTEEELEK MSHLPQRKGV   300
TFASILGPHD IVLKVDEEL                                               319

SEQ ID NO: 51                   moltype = AA  length = 314
FEATURE                         Location/Qualifiers
REGION                          1..314
                                note = CeresClone:1074583
```

```
source                          1..314
                                mol_type = protein
                                organism = Glycine max
SEQUENCE: 51
MGAGDKTAAG MPRIGMGTAV QGPKPDPIRR AVLRAIEVGY RHFDTAAHYE TEAPIGEAAA    60
EAVRSGAVAS RDDLFITSKL WCSDAHRDRV VPALRQTLRN LQMEYVDLYL VHWPVSMKPG   120
RPFKAPFTAED FVPFDMRAVW EAMEECHRLG LAKAIGVANF SCKKLETLLS FATIPPTVNQ  180
VEVNPVWQQR KLREFCRGKG IQLCAYSPLG AKGTHWGSDA VMDAGVLQEI AASRGKSVAQ   240
VCLRWVYEQG DCLIVKSFDE ARMRENLDVD GWELTEEEHR RIAEIPQRKI NLGKRYVSEH   300
GPYKSLEELW DGEI                                                    314

SEQ ID NO: 52                   moltype = AA   length = 315
FEATURE                         Location/Qualifiers
REGION                          1..315
                                note = gi[18]728
source                          1..315
                                mol_type = protein
                                organism = Glycine max
SEQUENCE: 52
MAAAIEIPTI VFPNSSAQQR MPVVGMGSAP DFTCKKDTKE AIIEAVKQGY RHFDTAAAYG    60
SEQALGEALK EAIHLGLVSR QDLFVTSKLW VTENHPHLVL PALRKSLKTL QLEYLDLYLI   120
HWPLSSQPGK FSFPIEVEDL LPFDVKGVWE SMEECKLGL TKAIGVSNFS VKKLQNLLSV   180
ATIRPVVDQV EMNLAWQQKK LREFCKENGI IVTAFSPLRK GASRGPNEVM ENDVLKEIAE   240
AHGKSIAQVS LRWLYEQGVT FVPKSYDKER MNQNLHIFDW ALTEQDHHKI SQISQSRLIS   300
GPTKPQLADL WDDQI                                                   315

SEQ ID NO: 53                   moltype = AA   length = 320
FEATURE                         Location/Qualifiers
REGION                          1..320
                                note = CeresClone:473625
source                          1..320
                                mol_type = protein
                                organism = Glycine max
SEQUENCE: 53
MEAKKIPEVI LNSGKKMPVI GLGTASIPLP SHEALTSILI DAFEVGYRHF DTASLYESEE    60
SLGKAVAKAL ELGLINSREE LFITSKLWST DAHPDLVVPA LKTSLQKLGL EYVDLYLIHW   120
PVRLKPEAKG YHNILKENVL PSFDMKGIWE AMEECYRLGL AKSIGVSNFG IKKLSQLLEN   180
ATIPPAVNQV EMSPTWQQGK LKEFCKQKGI HVSAWSPLGA YKSAQGTNAV MESPILKEIA   240
CERQKSMAQI ALRWIYEQGA IAIVKSFNKE RMKQNLDIFD WELSQEESQK FSQIPQRRMY   300
RGITFVSENG PYKTLEELWD                                              320

SEQ ID NO: 54                   moltype = AA   length = 322
FEATURE                         Location/Qualifiers
REGION                          1..322
                                note = CeresClone:474019
VARIANT                         274
                                note = Xaa can be any naturally occurring amino acid
source                          1..322
                                mol_type = protein
                                organism = Glycine max
SEQUENCE: 54
MAGKKIPDVL LNSGHKMPVI GMGTSVENRP SNETLASIYV EAIEVGYRHF DTAAVYGTEE    60
AIGLAVAKAI DKGLIKSRDE VFITSKPWNT DAHRDLIVPA LKTTLKKLGT EYVDLYLIHW   120
PVRLRHDLEN PTVFTKEDVL PFDIEGTWKA MEECYKLGIA KSIGICNYGI KKLTKLLEIA   180
TIPPAVNQVE MNPSWQQGKL REFCKQKGIH VSAWSALGAY KIFWGSGAVM ENPILQDIAK   240
AKGKTIAQVA LRWVYQQGSS AMAKSTNSER MKQXLDIFDF VLSEEDLERI SQVPQRRQYT   300
GDIWLSENGS CKTLEELWDG DV                                           322

SEQ ID NO: 55                   moltype = AA   length = 312
FEATURE                         Location/Qualifiers
REGION                          1..312
                                note = gi[56]3536
source                          1..312
                                mol_type = protein
                                organism = Medicago sativa
SEQUENCE: 55
MGSVEIPTKV LTNTSSQLKM PVVGMGSAPD FTCKKDTKDA IIEAIKQGYR HFDTAAAYGS    60
EQALGEALKE AIELGLVTRD ELFVTSKLWV TENHPHLVIP ALQKSLKTLQ LDYLDLYLIH   120
WPLSSQPGKF SFPIDVADLL PFDVKGVWES MEESLKLGLT KAIGVSNFSV KKLENLLSVA   180
TVLPAVNQVE MNLAWQQKKL REFCNAHGIV LTAFSPLRKG ASRGPNEVME NDMLKEIADA   240
HGKSVAQISL RWLYEQGVTF VPKSYDKERM NQNLRIFDWS LTKEDHEKIA QIKQNRLIPG   300
PTKPGLNDLY DD                                                      312

SEQ ID NO: 56                   moltype = AA   length = 312
FEATURE                         Location/Qualifiers
REGION                          1..312
                                note = gi[53]7298
```

```
source                  1..312
                        mol_type = protein
                        organism = Medicago sativa
SEQUENCE: 56
MGSVEIPTKV LTNTSSQLKM PVVGMGSAPD FTCKKDTKDA IIEAIKQGYR HFDTAAAYGS    60
EQALGEALKE AIELGLVTRE ELFVTSKLWV TENHPHLVIP ALQKSLKTLQ LDYLDLYLIH   120
WPLSSQPGKF SFPIDVADLL PFDVKGVWES MEESLKLGLT KAIGVSNFSV KKLENLLSVA   180
TVLPAVNQVE MNLAWQQKKL REFCNANGIV LTAFSPLRKG ASRGPNEVME NDMLKEIADA   240
HGKSVAQISL RWLYEQGVTF VPKSYDKERM NQNLCIFDWS LTKEDHEKID QIKQNRLIPG   300
PTKPGLNDLY DD                                                       312

SEQ ID NO: 57           moltype = AA  length = 312
FEATURE                 Location/Qualifiers
REGION                  1..312
                        note = gi[56]3538
source                  1..312
                        mol_type = protein
                        organism = Medicago sativa
SEQUENCE: 57
MDSVEIPTKV LTNTSSQLKM PVVGMGSAPD FTCKKDTKDA IIEAIKQGYR HFDTAAAYGS    60
EQALGEALKE AIELGLVTRE ELFVTSKLWV TENHPHLVIP ALQKSLKTLQ LDYLDLYLIH   120
WPLSSQPGKF SFPIDVADLL PFDVKGVWES MEESLKLGLT KAIGVSNFSV KKLENLLSVA   180
TVLPAVNQVE MNLAWQQKKL REFCNANGIV LTAFSPLRKG ASRGPNEVME NDMLKEIADA   240
HGKSVAQISL RWLYEQGVTF VPKSYDKERM NQNLCIFDWS LTKEDHEKID QIKQNRLIPG   300
PTKPGLNDLY DD                                                       312

SEQ ID NO: 58           moltype = AA  length = 312
FEATURE                 Location/Qualifiers
REGION                  1..312
                        note = gi[56]3540
source                  1..312
                        mol_type = protein
                        organism = Medicago sativa
SEQUENCE: 58
MGSVEIPTKV LTNTSSQLKM PVVGMGSAPD FTCKKDTKDA IIEAIKQGYR HFDTAAAYGS    60
EQALGEALKE AIELGLVTRD ELFVTSKLWV TENHPHLVIP ALQKSLKTLQ LDYLDLYLIH   120
WPLSSQPGKF TFPIDVADLL PFDVKGVWES MEESLKLGLT KAIGVSNFSV KKLENLLSVA   180
TVLPAVNQVE MNLAWQQKKL REFCNAHGIV LTAFSPLRKG ASRGPNEVME NDMLKEIADA   240
HGKSVAQISL RWLYEQGVTF VPKSYDKERM NQNLRIFDWS LTKEDHEKID QIKQNRLIPG   300
PTKPGLNDLY DD                                                       312

SEQ ID NO: 59           moltype = AA  length = 312
FEATURE                 Location/Qualifiers
REGION                  1..312
                        note = gi[53]7296
source                  1..312
                        mol_type = protein
                        organism = Medicago sativa
SEQUENCE: 59
MGSVEIPTKV LTNTSSQLKM PVVGMGSAPD FTCKKDTKDA IIEAIKQGYR HFDTAAAYGS    60
EQALGEALKE AIELGLVTRD DLFVTSKLWV TENHPHLVIP ALQKSLKTLQ LDYLDLYLIH   120
WPLSSQPGKF SFPIDVADLL PFDVKGVWES MEESLKLGLT KAIGVSNFSV KKLENLLSVA   180
TVLPAVNQVE MNLAWQQKKL REFCNAHGIV LTAFSPVRKG ASRGPNEVME NDMLKEIADA   240
HGKSVAQISL RWLYEQGVTF VPKSYDKERM NQNLRIFDWS LTKEDHEKIA QIKQNRLIPG   300
PTKPGLNDLY DD                                                       312

SEQ ID NO: 60           moltype = AA  length = 314
FEATURE                 Location/Qualifiers
REGION                  1..314
                        note = gi[20]147510
source                  1..314
                        mol_type = protein
                        organism = Pueraria lobata
SEQUENCE: 60
MAAIEIPTIV FPNSFAQHRV PVVEMGSAPD FTCKKDTKEA IIEAVKQGYR HFDTAAAYGS    60
EQALGEALKE AVDLGLVSRQ DLFVTSKLWV TDNHPHLVVS ALRKSLKTLQ LEYLDLYLIH   120
WPLSSQPGKF SFPIEVEDLL PFDVKGVWEA MQECQKLGLT KAIGVSNFSV KKLQNLLSVA   180
TIRPVVNQVE MNLAWQQKKL REFCKENGIV ITAFSPLRKG ASRGPNEVME NDVLKEIADA   240
HGKSIAQVSL RWLYEQGVTF VPKSYDKERM NQNLQIFDWA LTQEDHHKIS QISQSRLISG   300
PTKPQLSDLW DDEI                                                     314

SEQ ID NO: 61           moltype = AA  length = 322
FEATURE                 Location/Qualifiers
REGION                  1..322
                        note = gi[27]92155
source                  1..322
                        mol_type = protein
                        organism = Sesbania rostrata
```

```
SEQUENCE: 61
MAEKKIPEVL LNSGHKMPVI GMGTSVESRP SNDVLASIFV DAIQVGYRHF DSASVYGTEE        60
AIGMAVSKAI EQGLIKSRDE VFITSKPWNT DAHHDLIVPA LKTTLKKLGM EYVDLYLIHW       120
PVRLRHDLEN PVIFSKEDLL PFDIEGTWKA MEECYRLGLA KSIGICNYGT KKLTKLLEIA       180
TIPPAVNQVE MNPSWQQGNL REFCKQKGIH VSAWSPLGAY KIFWGSGAVM ENQILQDIAT       240
AKGKTIAQVA LRWVYQQGSS AMAKSFNKER MKQNLEIFDF ELSEEELEKI KQIPQRRQYT       300
GDMWLSENGS CKTLEELWDG DV                                                322

SEQ ID NO: 62              moltype = AA   length = 315
FEATURE                    Location/Qualifiers
REGION                     1..315
                           note = gi[13]160397
source                     1..315
                           mol_type = protein
                           organism = Digitalis purpurea
SEQUENCE: 62
MAEEIRFFKL NTGAKIPSVG LGTWQSSPGD AAQAVEVAIK CGYRHIDGAR LYENEKEIGV        60
VLKKLFDDGV VKREDLFITS KLWSTDHAPE DVPVALDKTL EDLQLDYIDL YLIHWPVRLK       120
KGSVGLDPEN FIPTDIPGTW KAMEALYDSG KARAIGVSNF TLKKLSDLLD VARIPPAVNQ       180
VGCHPSCAQT KLRAFCKSKG VHLSGYSPLG SPGTPWVKHD VLENPILVDV AEKLGKTPAQ       240
VAIRWGLQMG HSVLPKSVHE SRIKENIDVF SWCIPDDLFA KFSEIEQVSP GKPEFPVHPE       300
ISQYKTVEEM WDGGI                                                       315

SEQ ID NO: 63              moltype = AA   length = 315
FEATURE                    Location/Qualifiers
REGION                     1..315
                           note = gi[13]160399
source                     1..315
                           mol_type = protein
                           organism = Digitalis purpurea
SEQUENCE: 63
MAEEIRFFEL NTGAKIPSVG LGTWQSSPGD AAQAVEVAIK CGYRHIDGAR LYENEKEIGV        60
VLKKLFDDGV VKREDLFITS KLWSTDHAPE DVPVALDKTL EDLQLDYIDL YLIHWPVRLK       120
KGSVGLDPEN FVPTDIPGTW KAMEALYDSG KARAIGVSNF TLKKLSDLLD VARIPPAVNQ       180
VGCHPSCAQT KLRAFCKSKG IHLSGYSPLG SPGTPWVKHD VLENPILVDV AEKLGKTPAQ       240
VALRWGLQMG HSVLPKSVHE SRIKENIDVF SWCIPDVLFA KFSEIEQVSP GKPEFPVHPE       300
ISQYKTVEEM WDGGI                                                       315

SEQ ID NO: 64              moltype = AA   length = 319
FEATURE                    Location/Qualifiers
REGION                     1..319
                           note = gi[11]55213
source                     1..319
                           mol_type = protein
                           organism = Avena fatua
SEQUENCE: 64
MASAKAMGQG EQDRFVLKSG HAIPAVGLGT WRAGSDTAHS VQTAITEAGY RHVDTAAQYG        60
IEKEVDKGLK AAMEAGIDRK DLFVTSKIWR TNLAPERARP ALENTLKDLQ LDYIDLYLIH       120
WPFRLKDGAH QPPEAGEVLE FDMEGVWKEM EKLVKDGLVK DIDVCNFTVT KLNRLLRSAN       180
IPPAVCQMEM HPGWKNDKIF EACKKHGIHV TAYSPLGSSE KNLVHDPVVE KVANKLNKTP       240
GQVLIKWALQ RGTSVIPKSS KDERIKENIQ AFGWEIPEDD FQVLCSIKDE KRVLTGEELF       300
VNKTHGPYKS ASEVWDHEN                                                   319

SEQ ID NO: 65              moltype = AA   length = 320
FEATURE                    Location/Qualifiers
REGION                     1..320
                           note = gi[72]8592
source                     1..320
                           mol_type = protein
                           organism = Hordeum vulgare
SEQUENCE: 65
MASAKATMGQ GEQDHFVLKS GHAMPAVGLG TWRAGSDTAH SVRTAITEAG YRHVDTAAEY        60
GVEKEVGKGL KAAMEAGIDR KDLFVTSKIW CTNLAPERVR PALENTLKDL QLDYIDLYHI       120
HWPFRLKDGA HMPPEAGEVL EFDMEGVWKE MENLVKDGLV KDIGVCNYTV TKLNRLLRSA       180
KIPPAVCQME MHPGWKNDKI FEACKKHGIH ITAYSPLGSS EKNLAHDPVV EKVANKLNKT       240
PGQVLIKWAL QRGTSVIPKS SKDERIKENI QVFGWEIPEE DFKVLCSIKD EKRVLTGEEL       300
FVNKTHGPYR SARDVWDHEN                                                  320

SEQ ID NO: 66              moltype = AA   length = 321
FEATURE                    Location/Qualifiers
REGION                     1..321
                           note = gi[31]429855
source                     1..321
                           mol_type = protein
                           note = Oryza sativa subsp. japonica
                           organism = Oryza sativa
SEQUENCE: 66
MATIPEVPAS ELIQTMPRVG MGTAAFPFTS SEDTTAAMLR AIELGYRHFD TARIYATEGC        60
VGEAVAEAVR RGLIASRADV FVTSKIWCSD LHAGRVVPAA RETLRNLGMD YVDLLLVHWP       120
```

```
VSLTPGNYDF PFPKEVILPS FDMEGVWRGM EECHRLGLAR AIGVSNFSAK KLEQLLSLAA   180
VRPAVNQVEV NPMWQQRTLR EVCRREGVQL CGYSPLGAKG TPWGSAAVMD SGVLQEIAGA   240
KGKTLAQICL RWLYEQGDVL LVKTYNEKRM KENLDIFNWE LTDEERERIS QLPQLRGLPG   300
LEFISDHGPY KSVEDLWDGD V                                            321

SEQ ID NO: 67             moltype = AA  length = 322
FEATURE                   Location/Qualifiers
REGION                    1..322
                          note = gi[31]429856
source                    1..322
                          mol_type = protein
                          note = Oryza sativa subsp. japonica
                          organism = Oryza sativa
SEQUENCE: 67
MAMATIPEVP ASALLPTMPR IGMGTAAFPF TSSEETTAAL LRAIELGYRH FDTARLYATE    60
GCVSEAVAEA VRRGLVASRA DVFVTSKLWC SDLHAGRVVP AARETLRNLG MDYVDLLLVH   120
WPATVAPGSY DFPFPKEEMA PAFDMEGVWR GMEECHRLGL ARAIGVSNFS AKKLEQLLSF   180
AVVRPAANQV EMNPMWQQRT LREVCRREGV QLCGYSPLGA KGTPWGSAAV MDSGVLHDIA   240
QTKGKTLAQI CLRWMYEQGD VLLVKTYNEN RMKENLDIFD WELTEEERDK ISKLPQQRGL   300
TGMQFVCDNG PYKCVEDLWD GA                                           322

SEQ ID NO: 68             moltype = AA  length = 314
FEATURE                   Location/Qualifiers
REGION                    1..314
                          note = CeresClone:677995
source                    1..314
                          mol_type = protein
                          organism = Triticum aestivum
SEQUENCE: 68
MGAGDKTAAG MPRIGMGTAV QGPKPDPIRR AVLRAIEVGY RHFDTAAHYE TEAPIGEAAA    60
EAVRSGAVAS RDDLFITSKL WCSDAHRDRV VPALRQTLRN LQMEYVDLYL VHWPVSMKPG   120
RFKAPFTAED FVPFDMRAVW EAMEECHRLG LAKAIGVANF SCKKLETLLS FATIPPTVNQ   180
VEVNPVWQQR KLREFCRGKG IQLCTYSPLG AKGTHWGSDA VMDAGVLQEI AASRGKSVAQ   240
VCLRWVYEQG DCLIVKSFDE ARMRENLDVD GWELTEEEHR RIAEIPQRKI NLGKRYVSEH   300
GPYKSLEELW DGEI                                                    314

SEQ ID NO: 69             moltype = AA  length = 329
FEATURE                   Location/Qualifiers
REGION                    1..329
                          note = CeresClone:290117
source                    1..329
                          mol_type = protein
                          organism = Zea mays
SEQUENCE: 69
MASAGTTAVV PEVALRSGNA RTAMPMVGMG TASFPLVHEA VKDAVLSAIE VGFRHFDTAS    60
MYGTEKPLGD AVAEALRRGT LRSREDLFVT SKLWCSQNHP DLVLPSLRET LKNLQMEYVD   120
LYLIHWPVCL KPGPPELPTR KENAVPLDLA GVWRAMEECQ RLGLAKAIGV SNFTTRHLDG   180
VLAVATVPPA VNQVELNPAW QQRTLRAYCA DRGIHVAAYS PLGGQNWDGQ GSAVLDSEVL   240
AAIAKARGKT VAQVALRWIH EQGVTCIVKS YSKERLRQNL GIFDWELTDE ERLKISQIPQ   300
RKVVQTSSLF SQEGEFTAVD PAELNILEE                                    329

SEQ ID NO: 70             moltype = AA  length = 320
FEATURE                   Location/Qualifiers
REGION                    1..320
                          note = gi[54]3632
source                    1..320
                          mol_type = protein
                          organism = Bromus inermis
SEQUENCE: 70
MASAKAMMGQ ERQDHFVLKS GHAIPAVGLG TWRAGSDTAH SVQTAITEAG YRHVDTAAEY    60
GVEKEVGKGL KAAMEAGIDR KDLFVTSKLW CTDLVPDRVR PALEKTLKDL QLDYLDLYLI   120
HWPFRLKDGA HKPPEAGEVL EFDMEGVWKE MENLVKDGLV KDIGVCNYTV TKLNRLLQSA   180
KIAPAVCQME MHPGWKNDKI LEACKKHGIH ATAYSPLCSS EKNLAHDPVV EKVANKLNKT   240
PGQVLIKWAL QRGTIVIPKS SKDERIKENI QVFGWEIPEE DFQVLCSIKD EKRVLTGEEL   300
FVNKTHGPYK SASEVWDNEN                                              320

SEQ ID NO: 71             moltype = AA  length = 321
FEATURE                   Location/Qualifiers
REGION                    1..321
                          note = gi[40]781601
source                    1..321
                          mol_type = protein
                          organism = Hydrangea macrophylla
SEQUENCE: 71
MAFTIPEVPL SSGGRKMPVL GLGTAADPPV DPETVRKAVT EALKLGYRHF DTAALYNSEQ    60
PLGDAIAEAL GEGLIKSRDE LFITSKLWCS DAHRENVEPA LQKTLKNLKL EYIDMYLIHW   120
PVSSKPGNYE YPIKKEDFLQ MDYKSVWEAM EECQKLGLTK AIGVSNFSCK KLSDVLANAK   180
```

```
VPPAVNQVEV NPCWQQKQLT EFCKSNGILV VAYAALGAVG TFYGTNRVMG SEVLNEIARI        240
RGNTVAQVCL RWAYEQGIGV LVKSFNKERM EQNLQIFNWT LSDDESKKIS EIPQGRACLG        300
TDYTSVHGPF KTIEELWDGE F                                                 321

SEQ ID NO: 72           moltype = AA  length = 321
FEATURE                 Location/Qualifiers
REGION                  1..321
                        note = gi[50]920555
source                  1..321
                        mol_type = protein
                        note = Oryza sativa subsp. japonica
                        organism = Oryza sativa
SEQUENCE: 72
MSDGGAGAKG AGFGMPRVGM GTAVQGPRPE PIRRAVLKAI EAGYRHFDTA AHYETEAPIG        60
EAAAEAVRSG AIASRADLFI TSKLWCSDAH RDRVLPALRQ TLWNLQMEYV DLYLVHWPVS        120
MKPGRYKAPF TADDFVPFDM RAVWEAMEEC HRLGLAKAIG VCNFSCKKLD TLLSFATIPP        180
AVNQVEVNPV WQQRKLRELC REKGVQICAY SPLGASGTHW GSDSVMASAV LRDIAQSKGK        240
TVAQARHVCL RWVYEQGDCL IVKSFDEARM RENLDIVGWE LTEEERQRIA GIPQRKINRA        300
LRFVSDHGPY KSLDDLWDGE I                                                 321

SEQ ID NO: 73           moltype = AA  length = 323
FEATURE                 Location/Qualifiers
REGION                  1..323
                        note = gi[50]900440
source                  1..323
                        mol_type = protein
                        note = Oryza sativa subsp. japonica
                        organism = Oryza sativa
SEQUENCE: 73
MAAVPEVALR HGAGRPMPAV GVGTADSAAT SPETKRGAAL AALEVGFRHF DTAALYGTEA        60
PLGEAIAEAT RRGLVASREE VFVTTKLWCT QCHPGLVLPS LRESLRNLQM EYVDLYLVHW        120
PISVKPGPPM LPVKREDAVP FDFEGVWRAM EECHRLGLAK AIGVSNFTTK HLDKLLAVAT        180
IPPAVNQVEM NPVWQQRTVR EYCAAKGIRV AAYSPLGGQN WIGEGNDVME SPVLADIARA        240
RGKSIAQVSL RWIHEQGVTP IPKSYNKERL KQNLEIFDWE LTKEDRLKIS QIPQKKIVTA        300
ARMFSPDGEF ASVDLSDMEI VEE                                               323

SEQ ID NO: 74           moltype = AA  length = 323
FEATURE                 Location/Qualifiers
REGION                  1..323
                        note = gi[50]900438
source                  1..323
                        mol_type = protein
                        note = Oryza sativa subsp. japonica
                        organism = Oryza sativa
SEQUENCE: 74
MAVVVPEAVL RHGDARPMPA VGMGVAEYPS TPERTRDAVL AALEAGFRHF DTASLYRTEA        60
PLGEAIAEAT RRGLLASREE AFVTTKLWCT QCHPDLVLPS LRESLRNLQM EYVDLYLIHL        120
PISVKPGPMV FPVKKEDVVP FDFGGVWRAM EECHRLGLAK AIGVSNFTTK HIDKLLAVAT        180
ILPAVNQVEM NPTWQQRTVR EYCDAKGIRV TAYSPLGGQN WGGSANYVME SSVLTEIARA        240
RGKSIAQVSL RWIYEQGVTP IAKSYRKERL KENLEIFDWE LTDEDRLKIS QIPQRKRVTA        300
ASLFSPDGEF TSVDLPDIEI VEE                                               323

SEQ ID NO: 75           moltype = AA  length = 316
FEATURE                 Location/Qualifiers
REGION                  1..316
                        note = gi[15]14979
source                  1..316
                        mol_type = protein
                        organism = Glycyrrhiza glabra
SEQUENCE: 75
MAAAAIEIPT KVLPNSTCEL RVPVIGMGSA PDFTCKKDTK EAIIEAIKQG YRHFDTAAAY        60
GSETALGEAL KEARDLGLVT REDLFVTSKL WVTENHPHLV VPALRKSLET LQLEYLDLYL        120
IHWPLSSQPG KFSFPIQAED LLPFDKGVWE SMEESLKLGL LTKAIGVSNF SVKKLQNLLS        180
VATIRPAVNQ VEMNLAWQQK KLREFCNANG IVLTAFSPLR KGASRGPNEV MENDMLKGIA        240
EAHGKSIAQV SLRWLYEQGV TFVAKSYDKE RMNQNLQIFD WELTTEDHQK IDQIKQNRLI        300
PGPTKPQLND LWDDEI                                                       316

SEQ ID NO: 76           moltype = AA  length = 315
FEATURE                 Location/Qualifiers
REGION                  1..315
                        note = gi[15]14981
source                  1..315
                        mol_type = protein
                        organism = Glycyrrhiza glabra
SEQUENCE: 76
MAAAIEIPTK VLPNSTCELR VPVIGMGSAP DFTCKKDTKE AIIEAIKQGY RHFDTAAAYG        60
SETALGEALK EARDLGLVTR EDLFVTSKLW VTENHPHLVV PALRKSLETL QLEYLDLYLI        120
HWPLSSQPGK FSFPIQAEDL LPFDKGVWES MEESLKLGL TKAIGVSNFS VKKLQNLLSV        180
ATIRPAVNQV EMNLAWQQKK LREFCNANGI VLTAFSPLRK GASRGPNEVM ENDMLKGIAE        240
```

```
AHGKSIAQVS LRWLYEQGVT FVAKSYDKER MNQNLQIFDW ELTTEDHQKI DQIKQNRLIP    300
GPTKPQLNDL WDDEI                                                    315

SEQ ID NO: 77           moltype = DNA   length = 1133
FEATURE                 Location/Qualifiers
misc_feature            1..1133
                        note = clone125039_inplanta_experimental_L24
source                  1..1133
                        mol_type = other DNA
                        organism = Arabidopsis thaliana
SEQUENCE: 77
aagttttga tttcagagtc caccgttgag cctgttcaat taaatcgttg aatctcgcgg      60
tgcgttttac tttgattctt tcgaattttt tttatatgga tgttgccgcg atggcgagat   120
gtgtgggaag gtgctacgtt tcgccggcgt tcggtgagtc tgaatcgcac cggttatcgg   180
agcggcggtt tctgaaattg tctagctcca cgaattcgga tcccgccggt agtaaaagtt   240
tgaagcttcg cggaaaaatt catcggagaa tgagctactt ccgtccgatc atggcaaaag   300
atgaatccat ttcatcgcgg tccggtgaaa cgaagcaaat caatgaaag caaaagaaca    360
ttgtctggca tgattgtccc gttactaaat ccgacaggca agaattaatt aagcataagg   420
gatgtgtgat ttggattact ggcttaagtg gttcaggtaa aagtagtctg gcatgtgctc   480
ttagtcgagc tttgcacaat cgtggaaagc tttcgtatat acttgatggt gacaatgttc   540
gacatggttt aaacagcgat cttagtttcg aagcagatga tcgagctgaa aacattcgaa   600
gagttggtga agtggctaaa ctgtttgcag attctggtat tatctgtatt gcaagtttaa   660
tatctccta ccggatagaa cgagctgcct gccgtgcatt attaccacaa ggagatttca    720
ttgaggtatt tatggatgtg ccactccatg ttttgtgaagc tagagatcca aagggcttat   780
acaaacgtgc acgcgctggt aaaatcaaag gttttacagg agtagatgat ccatatgaag   840
cgcctttgga ttgcgagatt gtaatacaaa acagtagaga caaggggctt tcttcttcag   900
cttcatcttc atcttcacct tcatcttcgt cttcttctct gtgtgaaatg gcagatattg   960
ttgtgtcgta cttggaccaa aatggatacc tgaagaaaca ctccacaaaa tcacgtgatt  1020
gtatgtaaat gtaatattaa tatcattgtt gtaacgtttc ttaaacctat tttacctatg  1080
gacgattaaa ttgtgaaaac ataaatgtaa ttcacaatct gcaaagagtt ggc         1133

SEQ ID NO: 78           moltype = AA   length = 310
FEATURE                 Location/Qualifiers
REGION                  1..310
                        note = peptide_clone125039_inplanta_experimental_L24
source                  1..310
                        mol_type = protein
                        organism = Arabidopsis thaliana
SEQUENCE: 78
MDVAAMARCV GRCYVSPAFG ESESHRLSER RFLKLSSSTN SDPAGSKSLK LRGKIHRRMS     60
YFRPIMAKDE SISSRSGETK QINGKQKNIV WHDCPVTKSD RQELIKHKGC VIWITGLSGS    120
GKSSLACALS RALHNRGKLS YILDGDNVRH GLNSDLSFEA DDRAENIRRV GEVAKLFADS    180
GIICIASLIS PYRIERAACR ALLPQGDFIE VFMDVPLHVC EARDPKGLYK RARAGKIKGF    240
TGVDDPYEAP LDCEIVIQNS RDKGLSSSSS SSSSPSSSSS SLCEMADIVV SYLDQNGYLK    300
KHSTKSRDCM                                                          310

SEQ ID NO: 79           moltype = AA   length = 271
FEATURE                 Location/Qualifiers
REGION                  1..271
                        note = gi[33]29471
source                  1..271
                        mol_type = protein
                        organism = Enteromorpha intestinalis
SEQUENCE: 79
MLRAIAQRAR GSALQCAAPG TEWASCVRGS SGFTAYDVGE STNIKWHETM VSRGDKERLL     60
NQRGCVLWFT GLSGSGKSTV ACTLEHALNA RGKMTALLDG DNVRHGLNSN LTFTAEDRTE    120
HPPHRRSEQA LCRRWRPPLR ELHLRPIAPT RPVRERCAGD FVECYMKIPI ELCEQRDPKG    180
LYKKARAGLM KGFTGIDDPY EEPLEPELTI TVREEGSDMN SPEAMAKQIF DYLEAKGFLK    240
GPAVASSGGS CARVARWGGH GRRRGRQRLA W                                   271

SEQ ID NO: 80           moltype = AA   length = 290
FEATURE                 Location/Qualifiers
REGION                  1..290
                        note = gi[97]57873
source                  1..290
                        mol_type = protein
                        organism = Arabidopsis thaliana
SEQUENCE: 80
MARCVGRCYV SPAFGESESH RLSERRFLKL SSSTNSDPAG SKSLKLRGKI HRRMSYFRPI     60
MAKDESISSR SGETKQINGK QKNIVWHDCP VTKSDRQELI KQKGCVIWIT GLSGSGKSSL    120
ACALSRALHN RGKLSYILDG DNVRHGLNSD LSFEADDRAE NIRRVGEVAK LFADSGIICI    180
ASLISPYRIE RAACRALLPQ GDFIEVFMDV PLHVCEARDP KGLYKRARAG KIKGFTGVDD    240
PYEAPLDCEV HIISNFSSSS SLCEMADIVV SYLDQNGYLK KHSTKSRNCM               290

SEQ ID NO: 81           moltype = AA   length = 312
FEATURE                 Location/Qualifiers
REGION                  1..312
                        note = gi[28]32300
```

```
source                        1..312
                              mol_type = protein
                              organism = Catharanthus roseus
SEQUENCE: 81
MIGSVKRPVV SCVLPEFDFT ESTGLGKKSS SVKLPVNFGA FGSGGGEVKL GFLAPIKATE    60
GSKTSSFQVN GKVDNFRHLQ PSDCNSNSDS SLNNCNGFPG KKILQTTTVG NSTNILWHKC   120
AVEKSERQEP LQQRGCVIWI TGLSGSGKST LACALSRGLH AKGKLTYILD GDNVRHGLNS   180
DLSFKAEDRA ENIRRIGEVA KLFADAGVIC IASLISPYRK PPDACRSLLP EGDFIEVFMD   240
VPLKVCEARD PKGLYKLARA GKIKGFTGID DPYEPPLKSE IVLHQKLGMC DSPCDLADIV   300
ISYLEENGYL KA                                                      312

SEQ ID NO: 82                 moltype = AA  length = 275
FEATURE                       Location/Qualifiers
REGION                        1..275
                              note = CeresClone:300011
source                        1..275
                              mol_type = protein
                              organism = Zea mays
SEQUENCE: 82
MLARAPPPRP CSSGVCIARA HPRAAAVAAR PGTTRTTTTV AAAAEAASN GSAAAAVAGI    60
SSSSSALVTS TVGKSTNILW HECAIGQKER QGLLNQKGCV VWITGLSGSG KSTLACALSR   120
ELHGRGHLTY VLDGDNLRHG LNRDLSFGAE DRAENIRRVG EVAKLFADAG LVCIASLISP   180
YRSDRSACRD LLPKHSFIEV FLDVPLQVCE ARDPKGLYKL ARAGKIKGFT GIDDPYEPPS   240
DCEIVIQCKV GDCPSPESMA GHVVSYLETN GFLQD                             275

SEQ ID NO: 83                 moltype = AA  length = 345
FEATURE                       Location/Qualifiers
REGION                        1..345
                              note = gi[50]938537
source                        1..345
                              mol_type = protein
                              note = Oryza sativa subsp. japonica
                              organism = Oryza sativa
SEQUENCE: 83
MEASLPFHHH HPAASSTAAH HAARLTPPPP PRDPRATARW VPPAAAPVRS RSPANLGLPP    60
HPPRRLRLRL APPRITAAVT GGPRPRRRA PPPLECAGGS SSSLRRPREE EEEEEEERS    120
STAHAGVSLV GENKVLQMSS IVPKASNIFW HDCAVGQADR QKLLKQKGCV VWITGLSGSG   180
KSTLACTLDR ELHTRGKLSY VLDGDNLRHG LNKDLGFKAE DRAENIRRVG EVAKLFADAG   240
LVCIASFISP YRRDRESCRA LLSDGSFIEV FLNMPLELCE SRDPKGLYKL ARAGKIKGFT   300
GIDDPYESPL NSEIEIKEVD GVCPSPSDMA GQVVTYLEEK GFLHD                  345

SEQ ID NO: 84                 moltype = DNA  length = 497
FEATURE                       Location/Qualifiers
misc_feature                  1..497
                              note = 10044_13489782_L33
source                        1..497
                              mol_type = other DNA
                              organism = Arabidopsis thaliana
SEQUENCE: 84
aagaactcac ctaacacaca aacaaaggaa cttcactttt tttttcccaca ccacatcaca    60
ccatgtttag agccatgagc acaaggaaag tccatggtgg ctacgaaaag ctcggcgatg   120
aagaagcgag actgaagagg gtctctagcg ttccggctag tgtttatggt cattcaagaa   180
acccggttca agaagtgaag aagacaccga cagcgaaacc aaccggtggt tctgttcatc   240
ctttgtttag tttctttgac gttcattttc aaagaaagaa gaagaagacg acgaagaaga   300
agagtttagc aacggcgaaa ccagagtttg ctaggtatat ggagtatgtg agagaaggag   360
gtgtatggga tccgagttct aacgcaccag tgattcatta cagatagatt cgtcaaggaa   420
aatgaataaa agatttgtat atcgtctttt ttttcaaata tataatctat gagaaagcca   480
aacaatcctt gattcgg                                                 497

SEQ ID NO: 85                 moltype = AA  length = 114
FEATURE                       Location/Qualifiers
REGION                        1..114
                              note = peptide_10044_13489782_L33
source                        1..114
                              mol_type = protein
                              organism = Arabidopsis thaliana
SEQUENCE: 85
MFRAMSTRKV HGGYEKLGDE EARLKRVSSV PASVYGHSRN PVQEVKKTPT AKPTGGSVHP    60
LFSFFDVHFQ RKKKKTTKKK SLATAKPEFA RYMEYVREGG VWDPSSNAPV IHYR         114

SEQ ID NO: 86                 moltype = AA  length = 114
FEATURE                       Location/Qualifiers
REGION                        1..114
                              note = gi[48]35241
source                        1..114
                              mol_type = protein
                              organism = Arabidopsis thaliana
```

```
SEQUENCE: 86
MFRAMSTRKI HGGYEKLGDE EARLKRVSSV PASVYGHSRN PVQEVKKTPT AKPTGGSVHP    60
LFSFFDVHFQ RKKKNTAKKK SLATAKPEFA RYMEYVREGG VWDPSSNAPV IHYR         114

SEQ ID NO: 87           moltype = AA   length = 113
FEATURE                 Location/Qualifiers
REGION                  1..113
                        note = CeresClone:1068483
source                  1..113
                        mol_type = protein
                        organism = Brassica napus
SEQUENCE: 87
MFRAMSTRKV HGGYEKLVED EPKLKRVTSV PASVYGNSRN PVQEEVKKTP TVKPTGGSVH    60
PLLSFFDVRF QKKKKKTKKS LATAKPEFAR YMAYVKEGGV WDPNSNAPVI HYR           113

SEQ ID NO: 88           moltype = AA   length = 118
FEATURE                 Location/Qualifiers
REGION                  1..118
                        note = CeresClone:584111
source                  1..118
                        mol_type = protein
                        organism = Glycine max
SEQUENCE: 88
MFRSMTTRRG YERLGKESAT TALLHEGFKR STSLPSWGSN SSRKMALGST YGEINLKRNP    60
TKKGNNNSDK KSHPLLSFLA LRRKKKTTAR PEFARYLEYL KEGGMWDFNS NKPVMYYE      118

SEQ ID NO: 89           moltype = DNA   length = 913
FEATURE                 Location/Qualifiers
misc_feature            1..913
                        note = 10987_3769_L34
source                  1..913
                        mol_type = other DNA
                        organism = Arabidopsis thaliana
SEQUENCE: 89
aaaaatctgg aacggataaa ataatttgct cggcttcctc agctccaatg gcggcgacga    60
tgatcggaat taacctctcc tgcttcaaat caacatcgtt cttctcaccg gacctcaatt   120
ctctccaatc aaagctctct ctcctatctc tcaaaccctc tccaacacag ccacggaaat   180
caacagtcat ccgtatgggc ggtggtccga gaactttccc cggcggtgta tcaaaatggc   240
aatggaaaag gatgcaagcg aagaaacaga aacagctgtt ctatgcagag                300
aacgtcagat ctacgagatg cgaaaacgcg ccgagctaaa agcggcgtg gctgagctag    360
aacgaccatg ggaaccgatt cataaaccac cgaatctatt ctcagtttgt gctgatgagc   420
aagttaaagt actcgcggat cggttcagaa acctggtgg atttgattta tggactgata    480
gagatggtcc tcaattgttt gagagtgttg atgatttgcc ttctgctagg tttttttccta   540
aaggtgttgt tcatagtgtt aaaccttatg gtagattatc atctagctct gttgttgatg   600
atggtgatga gagtgaggtt aaagatgaag aaattgggaa gaagttacgt ggtcgtaggg   660
tgaggaagag aggtgatgat ggaggtaaga ggaggactga aaatcgtggt aatggtggga   720
gattgagaaa tggagggtct tcttcttctc aggtgtatga tatgacttg cagaatgatg    780
ggagatatga aattggatct taggtatgag ttcttctttg ttgtgtttgg atcattgatg   840
tctctgaaca taatttgtat gtaatctgga atagtttgat tgtgattatg caagttttca   900
gttttaggga agc                                                       913

SEQ ID NO: 90           moltype = AA   length = 251
FEATURE                 Location/Qualifiers
REGION                  1..251
                        note = peptide_10987_3769_L34
source                  1..251
                        mol_type = protein
                        organism = Arabidopsis thaliana
SEQUENCE: 90
MAATMIGINL SCFKSTSFFS PDLNSLQSKL SLLSLKPSPT QPRKSTVIRM GGGPRTFPGG    60
VSKWQWKRMQ AKKQKQLLKA RLCRERQIYE MRKRAELKAA VAELERPWEP IHKPPNLFSV   120
CADEQVKVLA DRFQKPGGFD LWTDRDGPQL FESVDDLPSA RFFPKGVVHS VKPYGRLSSS   180
SVVDDGDESE VKDEEIGKKL RGRRVRKRGD DGGKRRTENR GNGGRLRNGG SSSSQVYDMT   240
LQNDGRYEIG S                                                         251

SEQ ID NO: 91           moltype = DNA   length = 1252
FEATURE                 Location/Qualifiers
misc_feature            1..1252
                        note = cdna13500101_clone17206_L35
source                  1..1252
                        mol_type = other DNA
                        organism = Arabidopsis thaliana
SEQUENCE: 91
atcattcgtg tactaatttt accttcatag acttaattaa gatacgatca tggcgtcgtt    60
tgtctttgtg atttctcttc ttcttctctc tttttcgtcg gctgtttttct ccgatgatgc   120
ttcttttcag aaacttccgg tgcctgacaa gaggtcaggc cctgaatctt tcgcctttga   180
ctctaccggc ggattctaca ccggagtctc cggtggtaaa atcctcaagt acgttcctgg   240
gaagggttat gtcgattttg cccagatcac agattcctcg aactcggcat ggtgcaacgg   300
agcattagga accgctttcg ccggaaagtg tggtcgacca gcgggaatag ccttaaacag   360
```

```
caaaacaggt gatctctatg tcgccgatgc tccgttgggt cttcacgtta tctctcccgc    420
aggaggtttg gccacaaagc tggccgacag tgttgacgga aagcctttca agtttcttga    480
cggtcttgat gttgatccca ccaccggcgt cgtctacttc acttccttca gttccaagtt    540
tggaccccgg gaagtgttaa tcgcagtggg attaaaagac gcgagcggaa agctgttcaa    600
atacgaccca gcgaccaaag ccgtgactga gttaatggaa ggtctaagtg gtgctgctgg    660
ttgtgcagtg agctcagatg gttcattcgt gctagttagc gagttcataa agagtaacat    720
caagaaatat tggattaaag ggcccaaagc tggaactatt gaagacttct caagtcttgt    780
ctcgaacccc gacaacatca ggagggtagg ttctaccgga aatttctggg tcgcctctgt    840
cgtgaacaag gttgttatgc ctaccgaccc tagggcggtc aaactagacg ctaatggaaa    900
agtgctccag accattttcc tcaagaatga gtttgggaat actttgctta gtgaagtcaa    960
cgagttcaac ggccattttt acatcggaac tcttactgga cctttcgccg gagtcatgaa   1020
actttaaatt ggtatcaact atatggttct tggtgattaa ccattttga tatcattttg    1080
aaaggtctgt ttacagttat tttaaccata ataatatccc ctcaaatgtc ctgcttgtta   1140
cgtgggtgac acatttgttc ggtgattcct tgaataggct actactactt attgtttcat   1200
attttcgaag agattatctc tagttcttaa ggctttggtt ttctttgttt cc            1252

SEQ ID NO: 92           moltype = AA  length = 325
FEATURE                 Location/Qualifiers
REGION                  1..325
                        note = peptide_cdna13500101_clone17206_L35
source                  1..325
                        mol_type = protein
                        organism = Arabidopsis thaliana
SEQUENCE: 92
MASFVFVISL LLLLSFSSAVF SDDASFQKLP VPDKRSGPES FAFDSTGGFY TGVSGGKILK    60
YVPGKGYVDF AQITDSSNSA WCNGALGTAF AGKCGRPAGI ALNSKTGDLY VADAPLGLHV   120
ISPAGGLATK LADSVDGKPF KFLDGLDVDP TTGVVYFTSF SSKFGPREVL IAVGLKDASG   180
KLFKYDPATK AVTELMEGLS GAAGCAVSSD GSFVLVSEFI KSNIKKYWIK GPKAGTIEDF   240
SSLVSNPDNI RRVGSTGNFW VASVVNKVVM PTDPRAVKLD ANGKVLQTIF LKNEFGNTLL   300
SEVNEFNGHL YIGTLTGPFA GVMKL                                          325

SEQ ID NO: 93           moltype = AA  length = 335
FEATURE                 Location/Qualifiers
REGION                  1..335
                        note = gi[17]104523
source                  1..335
                        mol_type = protein
                        organism = Arabidopsis thaliana
SEQUENCE: 93
MTSFCSMISL LLLLSLSSAV FSDDASFQKL PVPETRSGPE AFAFDSTGKG FYTGVSGGKI    60
LKYLPETGYV DFAQITESSN SSWCDGTIGT ALAGRCGRPA GIAFNEKTGD LYVADAPLGL   120
HVISPAGGLA TKITDSVDGK PFKFLDGLDV DPTTGVVYFT SFSSRFSPIQ VLIALGLKDA   180
TGKLYKYDPS TKVVTVLMEG LSGSAGCAVS SDGSFVLVSQ FTKSNIKRYW IKGPKAGSSE   240
DFTNSVSNPD NIKRIGSTGN FWVASVVNKI IVPTNPSAVK VNSNGEVLQT IPLKDKFGDT   300
LLSEVNEFEG NLYIGTLTGP FAGILKLEKG SCPAT                                335

SEQ ID NO: 94           moltype = AA  length = 335
FEATURE                 Location/Qualifiers
REGION                  1..335
                        note = gi[17]54985
source                  1..335
                        mol_type = protein
                        organism = Arabidopsis thaliana
SEQUENCE: 94
MTSFCSMISL LLLLSLSSPV FSDDASFQKL PVPETRSGPE AFAFDSTGKG FYTGVSGGKI    60
LKYLPETGYV DFAQITESSN SSWCDGTIGT ALAGRCGRPA GIAFNEKTGD LYVADAPLGL   120
HVISPAGGLA TKITDSVDGK PFKFLDGLDV DPTTGVVYFT SFSSRFSPIQ VLIALGLKDA   180
TGKLYKYDPS TKVVTVLMEG LSGSAGCAVS SDGSFVLVSQ FTKSNIKRYW IKGPKAGSSE   240
DFTNSVSNPD NIKRIGSTGN FWVASVVNKI IVPTNPSAVK VNSNGEVLQT IPLKDKFGDT   300
LLSEVNEFEG NLYIGTLTGP FAGILKIEKG SCPAT                                335

SEQ ID NO: 95           moltype = AA  length = 338
FEATURE                 Location/Qualifiers
REGION                  1..338
                        note = CeresClone:124660
VARIANT                 102
                        note = Xaa can be any naturally occurring amino acid
source                  1..338
                        mol_type = protein
                        organism = Arabidopsis thaliana
SEQUENCE: 95
MTSFCSMISL LLLLLLLSLS SAVISDDASF QKLPVPETRS GPEAFAFDST KGFYTGVSG     60
GKILKYLPET GYVDFAQITE SSNSSWCDGT IGTALAGRCG RXAGIAFNEK TGDLYVADAP   120
LGLHVISPAG GLATKITDSV DGKPFKFLDG LDVDPTTGVV YFTSFSSRFS PIQVLIALGL   180
KDATGKLYKY DPSTKVVTVL MEGLSGSAGC AVSSDGSFVL VSQFTKSNIK RYWIKGPKAG   240
SSEDFTNSVS NPDNIKRIGS TGNFWVASVV NKIIVPTNPS AVKVNSNGEV LQTIPLKDKF   300
GDTLLSEVNE FEGNLYIGTL TGPFAGILKL EKGSCPAT                            338
```

```
SEQ ID NO: 96           moltype = AA  length = 344
FEATURE                 Location/Qualifiers
REGION                  1..344
                        note = gi[62]903513
source                  1..344
                        mol_type = protein
                        organism = Rauvolfia serpentina
SEQUENCE: 96
MAKLSDSQTM ALFTVFLLFL SSSLALSSPI LKEILIEAPS YAPNSFTFDS TNKGFYTSVQ    60
DGRVIKYEGP NSGFVDFAYA SPYWNKAFCE NSTDAEKRPL CGRTYDISYN LQNNQLYIVD   120
CYYHLSVVGS EGGHATQLAT SVDGVPFKWL YAVTVDQRTG IVYFTDVSTL YDDRGVQQIM   180
DTSDKTGRLI KYDPSTKETT LLLKELHVPG GAEVSADSSF VLVAEFLSHQ IVKYWLEGPK   240
KGTAEVLVKI PNPGNIKRNA DGHFWVSSSE ELDGNMHGRV DPKGIKFDEF GNILEVIPLP   300
PPFAGEHFEQ IQEHDGLLYI GTLFHGSVGI LVYDKKGNSF VSSH                   344

SEQ ID NO: 97           moltype = DNA  length = 1150
FEATURE                 Location/Qualifiers
misc_feature            1..1150
                        note = clone104691_L45
source                  1..1150
                        mol_type = other DNA
                        organism = Arabidopsis thaliana
SEQUENCE: 97
acgactacaa agtacaagaa agtctcattt gagaataatt gagcgataaa gaaacggtat    60
gacgtcgttt tgctccatga tttctcttct tcttcttctc tctctttcat cggcggtttt   120
ctccgatgac gcttctttcc agaaacttcc ggtgccggaa actaggtcag gtcccgaagc   180
tttcgctttt gattccaccg gtaaagggtt ctataccggt gtctccggtg gtaaaatcct   240
caagtacctc cccgagacgg gttatgttga ctttgcccag atcactgaat cctcgaactc   300
ttcatggtgc gatggtacta ttggaacggc tttagccgga cgctgtggtc gaccagcagg   360
aatagcattc aacgagaaaa caggtgatct ttacgtcgcc gatgctccgt gggtcttca    420
cgttatttct cccgccggtg gtttggctac gaagatcacc gacagtgttg acggaaagcc   480
tttcaagttt cttgacggtc ttgacgttga tcccactact ggtgtcgtct acttcacttc   540
cttcagctca cgcttctccc caatccaagt gttgattgca ttgggggttaa aggacgcgac   600
cggaaagctc tacaaatacg acccatcgac caaagtcgtg actgtactga tggaagggct   660
aagtggttca gccgggtgtg cagtgagctc agatggttcg tttgtgctgg ttagtcagtt   720
cacaaaaagt aacatcaaga ggtattggat caagggaccc aaagctggtt cttctgaaga   780
cttcaccaac tcagtctcaa accctgacaa tatcaaaaga attggctcta ctggaaactt   840
ttgggtcgct tcagtggtga acaagatcat cgtacctacg aacccatcag cagtcaaagt   900
taactctaat ggtgaagttc ttcaaacaat tcctctcaaa gataaatttg gagacactct   960
gctcagcgaa gtcaacgaat tcgagggcaa tttatatata ggaactctca ccggaccatt  1020
tgctggaatt cttaagctcg aaaagggttc ttgtcctgcc acttagatct cttatttgaa  1080
tgcatccgat gtgttacaat aatatatata tatgagcttt ttatttattt ctgaataaaa  1140
taaccactta                                                        1150

SEQ ID NO: 98           moltype = AA  length = 335
FEATURE                 Location/Qualifiers
REGION                  1..335
                        note = peptide_clone104691_L45
source                  1..335
                        mol_type = protein
                        organism = Arabidopsis thaliana
SEQUENCE: 98
MTSFCSMISL LLLLSLSSAV FSDDASFQKL PVPETRSGPE AFAFDSTGKG FYTGVSGGKI    60
LKYLPETGYV DFAQITESSN SSWCDGTIGT ALAGRCGRPA GIAFNEKTGD LYVADAPLGL   120
HVISPAGGLA TKITDSVDGK PFKFLDGLDV DPTTGVVYFT SFSSRFSPIQ VLIALGLKDA   180
TGKLYKYDPS TKVVTVLMEG LSGSAGCAVS SDGSFVLVSQ FTKSNIKRYW IKGPKAGSSE   240
DFTNSVSNPD NIKRIGSTGN FWVASVVNKI IVPTNPSAVK VNSNGEVLQT IPLKDKFGDT   300
LLSEVNEFEG NLYIGTLTGP FAGILKLEKG SCPAT                             335

SEQ ID NO: 99           moltype = AA  length = 325
FEATURE                 Location/Qualifiers
REGION                  1..325
                        note = CeresClone:17206
source                  1..325
                        mol_type = protein
                        organism = Arabidopsis thaliana
SEQUENCE: 99
MASFVFVISL LLLSFSSAVF SDDASFQKLP VPDKRSGPES FAFDSTGGFY TGVSGGKILK    60
YVPGKGYVDF AQITDSSNSA WCNGALGTAF AGKCGRPAGI ALNSKTGDLY VADAPLGLHV   120
ISPAGGLATK LADSVDGKPF KFLDGLDVDP TTGVVYFTSF SSKFGPREVL IAVGLKDASG   180
KLFKYDPATK AVTELMEGLS GAAGCAVSSD GSFVLVSEFI KSNIKKYWIK GPKAGTIEDF   240
SSLVSNPDNI RRVGSTGNFW VASVVNKVVM PTDPRAVKLD ANGKVLQTIF LKNEFGNTLL   300
SEVNEFNGHL YIGTLTGPFA GVMKL                                        325

SEQ ID NO: 100          moltype = AA  length = 325
FEATURE                 Location/Qualifiers
REGION                  1..325
                        note = gi[30]984544
```

```
source                      1..325
                            mol_type = protein
                            organism = Arabidopsis thaliana
SEQUENCE: 100
MASFVFVISL LLLSFSSAVF SDDASFQKLP VPDKRSGPES FAFDSTGGFY TGVSGGKILK    60
YVPGKGYVDF AQITDSSNSA WCNGALGTAF AGKCGRPAGI ALNSKTGDLY VADAPLGLHV   120
ISPAGGLATK LADSVDGKPF KFLDGLDVDP TTGVVYFTSF SSKFGPREVL IAVGLKDASG   180
KLFKYDPATK AVTELMEGLS GAAGCAVSSD GSFVLVSEFI KSNIKKYWIK GPKAGTIEDF   240
SSLVSNPDNI RRVGSTGNFW VASVVNKVVM PTDPRAVKLD ANGKVLQTIF LKNEFGNTLL   300
SEVNEFNGHL YIGTLTGPFA GVMKL                                        325

SEQ ID NO: 101              moltype = AA length = 328
FEATURE                     Location/Qualifiers
REGION                      1..328
                            note = gi[30]698979
source                      1..328
                            mol_type = protein
                            organism = Arabidopsis thaliana
SEQUENCE: 101
MRSFVSLISL LLLLSFSSSV LSTKKSSFQK LPVPGNRTGP EAFAFDSTGK GFYTGVTGGK    60
ILKYLPKKGY VDFAQITNSS KSSLCDGALG TTNVEKCGRP AGIAFNTKTG DLYVADAALG   120
LHVIPRRGGL AKKIADSVGG KPFLFLDGLD VDPTTGVVYF TSFSSTFGPR DVLKAVATKD   180
STGKFFKYDP SKKVVTVLME GLSGSAGCAV SSDGSFVLVG QFTKSNIKRY WIKGSKAGTS   240
EDFTNSVSNP DNIKRIGSTG NFWVASVVNS ATGPTNPSAV KVSSAGKVLQ TIPLKDKFGD   300
TLVSEVNEYK GQLYIGALFG PFAGILKL                                     328

SEQ ID NO: 102              moltype = AA length = 329
FEATURE                     Location/Qualifiers
REGION                      1..329
                            note = gi[12]325143
source                      1..329
                            mol_type = protein
                            organism = Arabidopsis thaliana
SEQUENCE: 102
MMRSFVSLIS LLLLLSFSSS VLSTKKSSFQ KLPVPGNRTG PEAFAFDSTG KGFYTGVTGG    60
KILKYLPKKG YVDFAQITNS SKSSLCDGAL GTTNVEKCGR PAGIAFNTKT GDLYVADAAL   120
GLHVIPRRGG LAKKIADSVG GKPFLFLDGL DVDPTTGVVY FTSFSSTFGP RDVLKAVATK   180
DSTGKFFKYD PSKKVVTVLM EGLSGSAGCA VSSDGSFVLV GQFTKSNIKR YWIKGSKAGT   240
SEDFTNSVSN PDNIKRIGST GNFWVASVVN SATGPTNPSA VKVSSAGKVL QTIPLKDKFG   300
DTLVSEVNEY KGQLYIGALF GPFAGILKL                                    329

SEQ ID NO: 103              moltype = AA length = 347
FEATURE                     Location/Qualifiers
REGION                      1..347
                            note = CeresClone:621848
source                      1..347
                            mol_type = protein
                            organism = Glycine max
SEQUENCE: 103
MKLSTLFLFL FHLAHAALSD EATFIRDGLK SYSQLDLPHS VFGSESVAFD CHGKGPYVGV    60
SDGRILKWHE TKREWIDFAV TSPHRNKKLC DGLTNDKMES MCGRPLGLKF NTLTCELYIA   120
DAYFGLLVVG PGGGVAKQLA TSAEGVPFRF TNALDIDTKT GEVYFTDSSI MFQRRVYISI   180
ILSGDRTGRL LKYVPSTQSV HVLVKGLAFP NGVALSKDNS FIIVAESTTF KILKIQVRDS   240
KTNNNNIEPF AQVPRSPDNI KRNAKGEFWV ALNSGRGLIQ KLENEIETTL PWNADPVAIK   300
FDEKGRAIEV LDGEYGRQLD SVSEVEEHEG SLWIGSAVQP YIGLIKA                347

SEQ ID NO: 104              moltype = AA length = 347
FEATURE                     Location/Qualifiers
REGION                      1..347
                            note = gi[18]222
source                      1..347
                            mol_type = protein
                            organism = Catharanthus roseus
SEQUENCE: 104
MMAVFFMFFL LLLSSSSSSS SSSPILKKIF IESPSYAPNA FTFDSTDKGF YTSVQDGRVI    60
KYEGPNSGFT DFAYASPFWN KAFCENSTDP EKRPLCGRTY DISYDYKNSQ MYIVDGHYHL   120
CVVGKEGGYA TQLATSVQGV PFKWLYAVTV DQRTGIVYFT DVSSIHDDSP EGVEEIMNTS   180
DRTGRLMKYD PSTKETTLLL KELHVPGGAE ISADGSFVVV AEFLSNRIVK YWLEGPKKGS   240
AEFLVTIPNP GNIKRNSDGH FWVSSSEELD GGQHGSVVSR GIKFDGFGNI LQVIPLPPPY   300
EGEHFEQIQE HDGLLYIGSL SHSSVGILVY DDHDNKGNSY VSQLVIN                347

SEQ ID NO: 105              moltype = AA length = 352
FEATURE                     Location/Qualifiers
REGION                      1..352
                            note = gi[18]220
source                      1..352
                            mol_type = protein
                            organism = Catharanthus roseus
```

```
SEQUENCE: 105
MANFSESKSM MAVFFMFFLL LLSSSSSSSS SSPILKKIFI ESPSYAPNAF TFDSTDKGFY    60
TSVQDGRVIK YEGPNSGFTD FAYASPFWNK AFCENSTDPE KRPLCGRTYD ISYDYKNSQM   120
YIVDGHYHLC VVGKEGGYAT QLATSVQGVP FKWLYAVTVD QRTGIVYFTD VSSIHDDSPE   180
GVEEIMNTSD RTGRLMKYDP STKETTLLLK ELHVPGGAEI SADGSFVVVA EFLSNRIVKY   240
WLEGPKKGSA EFLVTIPNPG NIKRNSDGHF WVSSSEELDG GQHGRVVSRG IKFDGFGNIL   300
QVIPLPPPYE GEHFEQIQEH DGLLYIGSLF HSSVGILVYD DHDNKGNSYV SS           352

SEQ ID NO: 106        moltype = AA   length = 343
FEATURE               Location/Qualifiers
REGION                1..343
                      note = CeresClone:316544
source                1..343
                      mol_type = protein
                      organism = Zea mays
SEQUENCE: 106
MAAAATRSLH SFLALLLLLA AAAAAAALSY ETKSIDPGLV VMTLPEPVSG PESLAFDGRG    60
GGPYSGVSDG RVLRWQGPLR GWTEFAYNSK HRSVALCAPD KKLVVPESLC GRPLGLQFHR   120
QSGDLYVADA YLGLLRVAAR GGLAQVVATE AAGGPFNFLN GLDVDQRTGD VYFTDSSATY   180
RRSDYLLVVA MGDETGRLLR YERRTGRVGV LQAGLSYPNG VAVSADGTHV VVAHTALCEL   240
RRYWIRGARA GTSDTFAELP GYPDNLRADG RGGYWVALSS GVAADEAAAA PTVAVRVSRD   300
GNVTEALDGF SFVSVSEVAQ RGGALWVGSV DTPYAGQLKR RAS                     343

SEQ ID NO: 107        moltype = AA   length = 364
FEATURE               Location/Qualifiers
REGION                1..364
                      note = gi[50]899872
source                1..364
                      mol_type = protein
                      note = Oryza sativa subsp. japonica
                      organism = Oryza sativa
SEQUENCE: 107
MRKGAAGMAC TCSAAAAASA LVKLLVLVAA VAATTSAGGG DEPTYETKSI DPSLAVMTLP    60
APVTGPESLA FDGRGDGPYT GGSDGRILRW RGGRLGWTEF AYNSRHKSVG VCSPEKKLVV   120
PESVCGRPLG LQFHHASGDL YVADAYLGLL RVPARGGLAE VVATEAAGVP FNFLNGLDVD   180
QRTGDVYFTD SSTTYRRSQY LLVVAMGDET GRLLRYDARR RVTVLHSGL PYPNGVAVSD    240
DGTHVVVAHT GLCELRRYWL RGPRAGKSET FAEVPGYPDN VRRDGDGGYW VALSRGADND   300
DVAPTVAVRV TAAGKKKGGG AAVVAEALAG FSFVTVSEVA EQNGTLWIGS VDTPYAGAAV   360
RGRR                                                                364

SEQ ID NO: 108        moltype = AA   length = 351
FEATURE               Location/Qualifiers
REGION                1..351
                      note = gi[13]928598
source                1..351
                      mol_type = protein
                      organism = Ophiorrhiza pumila
SEQUENCE: 108
MHSSEAMVVS ILCALFLSSL SLVSSSPEFF EFIEAPSYGP NAYAFDSDGE LYASVEDGRI    60
IKYDKPSNKF LTHAVASPIW NNALCENNTN QDLKPLCGRV YDFGFHYETQ RLYIADCYFG   120
LGFVGPDGGH AIQLATSGDG VEFKWLYALA IDQQAGFVYV TDVSTKYDDR GVQDIIRIND   180
TTGRLIKYDP STEEVTVLMK GLNIPGGTEV SKDGSFVLVG EFASHRILKY WLKGPKANTS   240
EFLLKVRGPG NIKRTKDGDF WVASSDNNGI TVTPRGIRFD EFGNILEVVA IPLPYKGEHI   300
EQVQEHDGAL FVGSLFHEFV GILHNYKSSV DHHQEKNSGG LNASFKEFSS F            351

SEQ ID NO: 109        moltype = AA   length = 342
FEATURE               Location/Qualifiers
REGION                1..342
                      note = gi[21]097
source                1..342
                      mol_type = protein
                      organism = Rauvolfia mannii
SEQUENCE: 109
KLSDSQTMAL FTVFLLFLSS SLALSSPILK EILIEAPSYA PNSFTFDSTN KGFYTSVQDG    60
RVIKYEGPNS GFVDFAYASP YWNKAFCENS TDAEKRPLCG RTYDISYNLQ NNQLYIVDCY   120
YHLSVVGSEG GHATQLATSV DGVPFKWLYA VTVDQRTGIV YFTDVSTLYD DRGVQQIMDT   180
SDKTGRLIKY DPSTKETTLL LKELHVPGGA EVSADSSFVL VAEFLSHQIV KYWLEGPKKG   240
TAEVLVKIPN PGNIKRNADG HFWVSSSEEL DGNMHGRVDP KGIKFDEFGN ILEVIPLPPP   300
FAGEHFEQIQ EHDGLLYIGT LFHGSVGILV YDKKGNSFVS SH                      342

SEQ ID NO: 110        moltype = DNA   length = 1954
FEATURE               Location/Qualifiers
misc_feature          1..1954
                      note = PROMOTER: 326 REPORT: 56
source                1..1954
                      mol_type = other DNA
                      organism = Arabidopsis thaliana
```

```
SEQUENCE: 110
gtgggtaaaa gtatccttct ttgtgcattt ggtatttta agcatgtaat aagaaaaacc    60
aaaatagacg gctggtattt aataaaagga gactaatgta tgtatagtat atgatttgtg   120
tggaatataa taaagttgta aaatatagat gtgaagcgag tatctatctt ttgactttca   180
aaggtgatcg atcgtgttct ttgtgatagt ttttggtcgtc ggtctacaag tcaacaacca   240
ccttgaagtt ttcgcgtctc ggtttcctct tcgcatctgg tatccaatag catacatata   300
ccagtgcgga aaatggcgaa gactagtggg cttgaaccat aaggtttggc cccaatacgg   360
attccaaaca acaagcctag cgcagtcttt tgggatgcat aagactaaac tgtcgcagtg   420
atagacgtaa gatatatcga cttgattgga atcgtctaag ctaataagtt taccttgacc   480
gtttatagtt gcgtcaacgt cctatggag attgatgccc atcaaataaa cctgaaaatc   540
catcaccatg accaccataa actcccttgc tgccgctgct ttggcttgag caaggtgttt   600
ccttgtaaag ctccgatctt tggataaagt gttccacttt tgcaagtag ctctgacccc   660
tctcagagat gtcaccggaa tcttagacag aacctcctct gccaaatcac ttggaagatc   720
ggacaatgtc atcatttttg caggtaattt ctccttcgtt gctgctttgg cttgagcacg   780
gtgcttcttt gtaaagctcc gatctttgga taagagcgga tcggaatcct ctaggagtg   840
ccagtccctt gacctattaa tttatagaag gttttagtgt atttgttcc aatttcttct   900
ctaacttaac aaataacaac tgcctcatag tcatgggctt caaattttat cgcttggtgt   960
atttcgttat ttgcaaggcc ttggcccatt ttgagcccaa taactaaatc tagccttc    1020
agaccggaca tgaacttcgc atattggcgt aactgtgcag ttttacctt ttcggatcag   1080
acaagatcag atttagacca cccaacaata gtcagtcata tttgacaacc taagctagcc   1140
gacactacta aaaagcaaac aaaagaagaa ttctatgttg tcatttacc ggtggcaagt   1200
ggacccttct ataaaagagt aaagagacag cctgtgtgta taatctct aattatgttc   1260
accgacacaa tcacacaaac ccttctctaa tcacacaact tcttcatgat ttacgacatt   1320
aattatcatt aactcttta attcacttta catgctcaaa aatatctaat ttgcagcatt   1380
aatttgagta ccgataacta ttattataat cgtcgtgatt cgcaatcttc ttcattagat   1440
gctgtcaagt tgtactcgca cgcggtggtc cagtgaagca aatccaacgg tttaaaacct   1500
tcttacattt ctagatctaa tctgaaccgt cagatatcta gatctcattg tctgaacaca   1560
gttagatgaa actgggaatg aatctggacg aaattacgat cttacaccaa ccccctcgac   1620
gagctcgtat atataaagct tatacgctcc tccttcacct tcgtactact actaccacca   1680
catttcttta gctcaacctt cattactaat ctccttttaa ggtatgttca cttttcttcg   1740
attcatactt tctcaagatt cctgcatttc tgtagaattt gaaccaagtg tcgattttt   1800
tttgagagaa gtgttgattt atagatcggg ttattgaatc tagattccaa tttttaattg   1860
attcgagttt gttatgtgtg tttatactac ttctcattga tcttgtttga tttctctgct   1920
ctgtattagg tttctttcgt gaatcagatc ggaa                              1954

SEQ ID NO: 111        moltype = DNA  length = 2016
FEATURE               Location/Qualifiers
misc_feature          1..2016
                      note = PROMOTER: 32449; REPORT: 92
source                1..2016
                      mol_type = other DNA
                      organism = Arabidopsis thaliana
SEQUENCE: 111
gatcggcctt cttcaggtct tctctgtagc tctgttactt ctatcacagt tatcgggtat    60
ttgagaaaaa agagttagct aaaatgaatt tctccatata atcatggttt actacaggtt   120
tacttgattc gcgttagctt tatctgcatc caaagttttt tccatgatgt tatgtcatat   180
gtgataccgt tactatgttt ataactttat acagtctggt tcactggagt ttctgtgatt   240
atgttgagta catactcatt catccctttg taactctcaa gtttaggttg tttgaattgc   300
ctctgttgtg atacttattg tctattgcat caatcttcta atgcaccacc ctagactatt   360
tgaacaaaga gctgtttcat tcttaaacct ctgtgtctcc ttgctaaatg gtcatgcttt   420
aatgtcttca cctgtctttc tcttctatag atatgtagtc ttgctagata gttagttcta   480
cagctctctt ttgtagtctt gttagagagt tagttgagat attacctctt aaaagtatcc   540
ttgaacgctt tccggttatg accaatttgt tgtagctcct tgtaagtaga acttactggg   600
accagcgaga cagtttatgt gaatgttcat gcttaagtgt cgaacgtatc tatctctact   660
atagctctgt agtcttgtta gacagttagt tttatatctc catttttttg tagtcttgt    720
agttgagata ttacctcttc tcttcaaagt atccttgaac gctcaccggt tatgaaatct   780
ctacactata gctctgtagt cttgctagat agttagttct ttagctctct ttttgtagcc   840
tagttctttta gctctccttt tgtagccttg ctacagagta agatgggata ttacctcctt   900
gaacgctctc cggttatgac caatttgttg tagctccttg taagtagaac ttaggataga   960
gtgagtcaac tttaagaaag aacctagtat gtggcataac cagattgcag gctctgtctc  1020
ggctacagta acgtaactct atagctcttt gtttttgttca gaaagaacca gtgattggat  1080
gattcgtcct tagaaactgg acctaacaac agtcattggc tttgaaatca agccacaaca  1140
atgcctatat gaaccgtcca tttcatttat ccgtttcaaa ccagcccatt acatttcgtc  1200
ccattgataa ccaaaagcgg ttcaatcaga ttatgtttta attttaccaa attcttatg   1260
aagtttaaat tatactcaca ttaaaaggat tattggataa tgtaaaaatt ctgaacaatt  1320
actgattttg gaaaattaac aaatattctt gaaatagaa gaaaaagcct ttttcctttt  1380
gacaacaaca tataaaatca tactcccatt aaaaagattt taatgtaaaa ttctgaatat  1440
aagatatttt ttacaacaac aaccaaaaat attttatttt ttcctttttt acagcaacaa  1500
gaaggaaaaa cttttttttt tgtcaagaaa agggagatt atgtaaacag ataaaacagg  1560
gaaaataact aaccgaactc tcttaattaa catcttcaaa taaggaaaat tatgatccgc  1620
atatttagga agatcaatgc attaaaacaa cttgcacgtg gaaagagaga ctatacgctc  1680
cacacaagtt gcactaatgg tacctctcac aaaccaatca aaatactgaa taatgccaac  1740
gtgtacaaat tagggtttta cctcacaacc atcgaacatt ctcgaaacat tttaaacagc  1800
ctggcgccat agatctaaac tctcatcgac caattttga ctgccgatg gaaactctag  1860
cctcaaccca aaactctata taagaaatc ttttccttcg ttattgctta ccaaatacaa  1920
accctagccg ccttattcgt cttcttcgtt ctctagtttt ttcctcagtc tctgttctta  1980
gatcccttgt agtttccaaa tcttccgata aggcct                           2016

SEQ ID NO: 112        moltype = AA   length = 5
```

```
FEATURE              Location/Qualifiers
REGION               1..5
                     note = Fragment of consensus sequence of Table 1-4
source               1..5
                     mol_type = protein
                     organism = synthetic construct
SEQUENCE: 112
QWCVA                                                                     5

SEQ ID NO: 113       moltype = AA  length = 5
FEATURE              Location/Qualifiers
REGION               1..5
                     note = Fragment of consensus sequence of Table 1-4
source               1..5
                     mol_type = protein
                     organism = synthetic construct
SEQUENCE: 113
EQTTD                                                                     5

SEQ ID NO: 114       moltype = AA  length = 4
FEATURE              Location/Qualifiers
REGION               1..4
                     note = Fragment of consensus sequence of Table 1-4
source               1..4
                     mol_type = protein
                     organism = synthetic construct
SEQUENCE: 114
ELQA                                                                      4

SEQ ID NO: 115       moltype = AA  length = 5
FEATURE              Location/Qualifiers
REGION               1..5
                     note = Fragment of consensus sequence of Table 1-4
source               1..5
                     mol_type = protein
                     organism = synthetic construct
SEQUENCE: 115
DCSKI                                                                     5

SEQ ID NO: 116       moltype = AA  length = 17
FEATURE              Location/Qualifiers
REGION               1..17
                     note = Fragment of consensus sequence of Table 1-4
source               1..17
                     mol_type = protein
                     organism = synthetic construct
SEQUENCE: 116
NQPCFLPNTI RDHASYA                                                       17

SEQ ID NO: 117       moltype = AA  length = 6
FEATURE              Location/Qualifiers
REGION               1..6
                     note = Fragment of consensus sequence of Table 1-4
source               1..6
                     mol_type = protein
                     organism = synthetic construct
SEQUENCE: 117
NSYYQT                                                                    6

SEQ ID NO: 118       moltype = AA  length = 4
FEATURE              Location/Qualifiers
REGION               1..4
                     note = Fragment of consensus sequence of Table 1-4
source               1..4
                     mol_type = protein
                     organism = synthetic construct
SEQUENCE: 118
FKGA                                                                      4

SEQ ID NO: 119       moltype = AA  length = 4
FEATURE              Location/Qualifiers
REGION               1..4
                     note = Fragment of consensus sequence of Table 1-4
source               1..4
                     mol_type = protein
                     organism = synthetic construct
SEQUENCE: 119
IITE                                                                      4
```

```
SEQ ID NO: 120        moltype = AA  length = 7
FEATURE               Location/Qualifiers
REGION                1..7
                      note = Fragment of consensus sequence of Table 1-4
source                1..7
                      mol_type = protein
                      organism = synthetic construct
SEQUENCE: 120
DPSHGSC                                                                    7

SEQ ID NO: 121        moltype = AA  length = 5
FEATURE               Location/Qualifiers
REGION                1..5
                      note = Fragment of consensus sequence of Table 2-8
source                1..5
                      mol_type = protein
                      organism = synthetic construct
SEQUENCE: 121
MQMLR                                                                      5

SEQ ID NO: 122        moltype = AA  length = 15
FEATURE               Location/Qualifiers
REGION                1..15
                      note = Fragment of consensus sequence of Table 2-8
source                1..15
                      mol_type = protein
                      organism = synthetic construct
SEQUENCE: 122
LSTRTRSRRG GYERV                                                          15

SEQ ID NO: 123        moltype = AA  length = 25
FEATURE               Location/Qualifiers
REGION                1..25
                      note = Fragment of consensus sequence of Table 2-8
source                1..25
                      mol_type = protein
                      organism = synthetic construct
SEQUENCE: 123
SDDSTFSLLG AKLRRSTSVP YYAPS                                               25

SEQ ID NO: 124        moltype = AA  length = 4
FEATURE               Location/Qualifiers
REGION                1..4
                      note = Fragment of consensus sequence of Table 2-8
source                1..4
                      mol_type = protein
                      organism = synthetic construct
SEQUENCE: 124
IRLG                                                                       4

SEQ ID NO: 125        moltype = AA  length = 30
FEATURE               Location/Qualifiers
REGION                1..14
                      note = Fragment of consensus sequence of Table 2-8
source                1..30
                      mol_type = protein
                      organism = synthetic construct
SEQUENCE: 125
GDFPVILEKL PRQKPTKTVV TSKLSHPIFS                                           30

SEQ ID NO: 126        moltype = AA  length = 6
FEATURE               Location/Qualifiers
REGION                1..6
                      note = Fragment of consensus sequence of Table 2-8
source                1..6
                      mol_type = protein
                      organism = synthetic construct
SEQUENCE: 126
DGYRRR                                                                     6

SEQ ID NO: 127        moltype = AA  length = 9
FEATURE               Location/Qualifiers
REGION                1..9
                      note = Fragment of consensus sequence of Table 2-8
source                1..9
                      mol_type = protein
                      organism = synthetic construct
SEQUENCE: 127
TAKPEFSRY                                                                  9
```

```
SEQ ID NO: 128          moltype = AA  length = 5
FEATURE                 Location/Qualifiers
REGION                  1..5
                        note = Fragment of consensus sequence of Table 2-8
source                  1..5
                        mol_type = protein
                        organism = synthetic construct
SEQUENCE: 128
EYLKE                                                                    5

SEQ ID NO: 129          moltype = AA  length = 15
FEATURE                 Location/Qualifiers
REGION                  1..15
                        note = Fragment of consensus sequence of Table 2-8
source                  1..15
                        mol_type = protein
                        organism = synthetic construct
SEQUENCE: 129
GMWDLRSNSP VIYFK                                                        15

SEQ ID NO: 130          moltype = AA  length = 19
FEATURE                 Location/Qualifiers
REGION                  1..19
                        note = Fragment of consensus sequence of Table 3-9
source                  1..19
                        mol_type = protein
                        organism = synthetic construct
SEQUENCE: 130
KKHFVLVHGA CHGAWCWYK                                                    19

SEQ ID NO: 131          moltype = AA  length = 6
FEATURE                 Location/Qualifiers
REGION                  1..6
                        note = Fragment of consensus sequence of Table 3-9
source                  1..6
                        mol_type = protein
                        organism = synthetic construct
SEQUENCE: 131
KPLLEA                                                                   6

SEQ ID NO: 132          moltype = AA  length = 13
FEATURE                 Location/Qualifiers
REGION                  1..13
                        note = Fragment of consensus sequence of Table 3-9
source                  1..13
                        mol_type = protein
                        organism = synthetic construct
SEQUENCE: 132
GHRVTALDLA ASG                                                          13

SEQ ID NO: 133          moltype = AA  length = 4
FEATURE                 Location/Qualifiers
REGION                  1..4
                        note = Fragment of consensus sequence of Table 3-9
source                  1..4
                        mol_type = protein
                        organism = synthetic construct
SEQUENCE: 133
PRQI                                                                     4

SEQ ID NO: 134          moltype = AA  length = 9
FEATURE                 Location/Qualifiers
REGION                  1..9
                        note = Fragment of consensus sequence of Table 3-9
source                  1..9
                        mol_type = protein
                        organism = synthetic construct
SEQUENCE: 134
YSEPLMELM                                                                9

SEQ ID NO: 135          moltype = AA  length = 9
FEATURE                 Location/Qualifiers
REGION                  1..9
                        note = Fragment of consensus sequence of Table 3-9
source                  1..9
                        mol_type = protein
                        organism = synthetic construct
```

```
SEQUENCE: 135
EKVVLVGHS                                                                               9

SEQ ID NO: 136          moltype = AA  length = 22
FEATURE                 Location/Qualifiers
REGION                  1..22
                        note = Fragment of consensus sequence of Table 3-9
source                  1..22
                        mol_type = protein
                        organism = synthetic construct
SEQUENCE: 136
GGLNIALAME KFPEKISVAV FL                                                               22

SEQ ID NO: 137          moltype = AA  length = 6
FEATURE                 Location/Qualifiers
REGION                  1..6
                        note = Fragment of consensus sequence of Table 3-9
source                  1..6
                        mol_type = protein
                        organism = synthetic construct
SEQUENCE: 137
MPDTEH                                                                                  6

SEQ ID NO: 138          moltype = AA  length = 4
FEATURE                 Location/Qualifiers
REGION                  1..4
                        note = Fragment of consensus sequence of Table 3-9
source                  1..4
                        mol_type = protein
                        organism = synthetic construct
SEQUENCE: 138
VLEK                                                                                    4

SEQ ID NO: 139          moltype = AA  length = 6
FEATURE                 Location/Qualifiers
REGION                  1..6
                        note = Fragment of consensus sequence of Table 3-9
source                  1..6
                        mol_type = protein
                        organism = synthetic construct
SEQUENCE: 139
WMDTEF                                                                                  6

SEQ ID NO: 140          moltype = AA  length = 4
FEATURE                 Location/Qualifiers
REGION                  1..4
                        note = Fragment of consensus sequence of Table 3-9
source                  1..4
                        mol_type = protein
                        organism = synthetic construct
SEQUENCE: 140
TSMI                                                                                    4

SEQ ID NO: 141          moltype = AA  length = 6
FEATURE                 Location/Qualifiers
REGION                  1..6
                        note = Fragment of consensus sequence of Table 3-9
source                  1..6
                        mol_type = protein
                        organism = synthetic construct
SEQUENCE: 141
LYQLSP                                                                                  6

SEQ ID NO: 142          moltype = AA  length = 10
FEATURE                 Location/Qualifiers
REGION                  1..10
                        note = Fragment of consensus sequence of Table 3-9
source                  1..10
                        mol_type = protein
                        organism = synthetic construct
SEQUENCE: 142
MLVRPGSLFI                                                                             10

SEQ ID NO: 143          moltype = AA  length = 10
FEATURE                 Location/Qualifiers
REGION                  1..10
                        note = Fragment of consensus sequence of Table 3-9
```

```
source                      1..10
                            mol_type = protein
                            organism = synthetic construct
SEQUENCE: 143
YGSVKRVYIY                                                              10

SEQ ID NO: 144              moltype = AA   length = 10
FEATURE                     Location/Qualifiers
REGION                      1..10
                            note = Fragment of consensus sequence of Table 3-9
source                      1..10
                            mol_type = protein
                            organism = synthetic construct
SEQUENCE: 144
FQRWMIENYP                                                              10

SEQ ID NO: 145              moltype = AA   length = 4
FEATURE                     Location/Qualifiers
REGION                      1..4
                            note = Fragment of consensus sequence of Table 3-9
source                      1..4
                            mol_type = protein
                            organism = synthetic construct
SEQUENCE: 145
EIEG                                                                     4

SEQ ID NO: 146              moltype = AA   length = 7
FEATURE                     Location/Qualifiers
REGION                      1..7
                            note = Fragment of consensus sequence of Table 3-9
source                      1..7
                            mol_type = protein
                            organism = synthetic construct
SEQUENCE: 146
SKPQELS                                                                  7

SEQ ID NO: 147              moltype = AA   length = 5
FEATURE                     Location/Qualifiers
REGION                      1..5
                            note = Fragment of consensus sequence of Table 5-8
source                      1..5
                            mol_type = protein
                            organism = synthetic construct
SEQUENCE: 147
FIQCL                                                                    5

SEQ ID NO: 148              moltype = AA   length = 6
FEATURE                     Location/Qualifiers
REGION                      1..6
                            note = Fragment of consensus sequence of Table 5-8
source                      1..6
                            mol_type = protein
                            organism = synthetic construct
SEQUENCE: 148
KLVYTP                                                                   6

SEQ ID NO: 149              moltype = AA   length = 9
FEATURE                     Location/Qualifiers
REGION                      1..9
                            note = Fragment of consensus sequence of Table 5-8
source                      1..9
                            mol_type = protein
                            organism = synthetic construct
SEQUENCE: 149
STYQNLRFL                                                                9

SEQ ID NO: 150              moltype = AA   length = 10
FEATURE                     Location/Qualifiers
REGION                      1..10
                            note = Fragment of consensus sequence of Table 5-8
source                      1..10
                            mol_type = protein
                            organism = synthetic construct
SEQUENCE: 150
TPKPLVIITP                                                              10
```

```
SEQ ID NO: 151           moltype = AA   length = 16
FEATURE                  Location/Qualifiers
REGION                   1..16
                         note = Fragment of consensus sequence of Table 5-8
source                   1..16
                         mol_type = protein
                         organism = synthetic construct
SEQUENCE: 151
SHIQAAVVCS KKHGLQ                                                         16

SEQ ID NO: 152           moltype = AA   length = 16
FEATURE                  Location/Qualifiers
REGION                   1..16
                         note = Fragment of consensus sequence of Table 5-8
source                   1..16
                         mol_type = protein
                         organism = synthetic construct
SEQUENCE: 152
RVRSGGHDYE GLSYVS                                                         16

SEQ ID NO: 153           moltype = AA   length = 7
FEATURE                  Location/Qualifiers
REGION                   1..7
                         note = Fragment of consensus sequence of Table 5-8
source                   1..7
                         mol_type = protein
                         organism = synthetic construct
SEQUENCE: 153
PFVVVDL                                                                    7

SEQ ID NO: 154           moltype = AA   length = 17
FEATURE                  Location/Qualifiers
REGION                   1..17
                         note = Fragment of consensus sequence of Table 5-8
source                   1..17
                         mol_type = protein
                         organism = synthetic construct
SEQUENCE: 154
TAWVQAGATL GELYYRI                                                        17

SEQ ID NO: 155           moltype = AA   length = 4
FEATURE                  Location/Qualifiers
REGION                   1..4
                         note = Fragment of consensus sequence of Table 5-8
source                   1..4
                         mol_type = protein
                         organism = synthetic construct
SEQUENCE: 155
EKSK                                                                       4

SEQ ID NO: 156           moltype = AA   length = 22
FEATURE                  Location/Qualifiers
REGION                   1..22
                         note = Fragment of consensus sequence of Table 5-8
source                   1..22
                         mol_type = protein
                         organism = synthetic construct
SEQUENCE: 156
GFPAGVCPTV GVGGHISGGG YG                                                  22

SEQ ID NO: 157           moltype = AA   length = 15
FEATURE                  Location/Qualifiers
REGION                   1..15
                         note = Fragment of consensus sequence of Table 5-8
source                   1..15
                         mol_type = protein
                         organism = synthetic construct
SEQUENCE: 157
LMRKYGLAAD NVIDA                                                          15

SEQ ID NO: 158           moltype = AA   length = 25
FEATURE                  Location/Qualifiers
REGION                   1..25
                         note = Fragment of consensus sequence of Table 5-8
source                   1..25
                         mol_type = protein
                         organism = synthetic construct
```

```
SEQUENCE: 158
VDNGKLLDRK SMGEDLFWAI RGGGG                                        25

SEQ ID NO: 159          moltype = AA  length = 4
FEATURE                 Location/Qualifiers
REGION                  1..4
                        note = Fragment of consensus sequence of Table 5-8
source                  1..4
                        mol_type = protein
                        organism = synthetic construct
SEQUENCE: 159
SFGV                                                               4

SEQ ID NO: 160          moltype = AA  length = 17
FEATURE                 Location/Qualifiers
REGION                  1..17
                        note = Fragment of consensus sequence of Table 5-8
source                  1..17
                        mol_type = protein
                        organism = synthetic construct
SEQUENCE: 160
LAWKIKLVPV PETVTVF                                                 17

SEQ ID NO: 161          moltype = AA  length = 6
FEATURE                 Location/Qualifiers
REGION                  1..6
                        note = Fragment of consensus sequence of Table 5-8
source                  1..6
                        mol_type = protein
                        organism = synthetic construct
SEQUENCE: 161
RTLEQN                                                             6

SEQ ID NO: 162          moltype = AA  length = 6
FEATURE                 Location/Qualifiers
REGION                  1..6
                        note = Fragment of consensus sequence of Table 5-8
source                  1..6
                        mol_type = protein
                        organism = synthetic construct
SEQUENCE: 162
KWQQVA                                                             6

SEQ ID NO: 163          moltype = AA  length = 4
FEATURE                 Location/Qualifiers
REGION                  1..4
                        note = Fragment of consensus sequence of Table 5-8
source                  1..4
                        mol_type = protein
                        organism = synthetic construct
SEQUENCE: 163
TVRA                                                               4

SEQ ID NO: 164          moltype = AA  length = 5
FEATURE                 Location/Qualifiers
REGION                  1..5
                        note = Fragment of consensus sequence of Table 5-8
source                  1..5
                        mol_type = protein
                        organism = synthetic construct
SEQUENCE: 164
LFLGG                                                              5

SEQ ID NO: 165          moltype = AA  length = 4
FEATURE                 Location/Qualifiers
REGION                  1..4
                        note = Fragment of consensus sequence of Table 5-8
source                  1..4
                        mol_type = protein
                        organism = synthetic construct
SEQUENCE: 165
LMNK                                                               4

SEQ ID NO: 166          moltype = AA  length = 6
FEATURE                 Location/Qualifiers
REGION                  1..6
                        note = Fragment of consensus sequence of Table 5-8
```

```
source                   1..6
                         mol_type = protein
                         organism = synthetic construct
SEQUENCE: 166
FPELGL                                                                    6

SEQ ID NO: 167           moltype = AA  length = 11
FEATURE                  Location/Qualifiers
REGION                   1..11
                         note = Fragment of consensus sequence of Table 5-8
source                   1..11
                         mol_type = protein
                         organism = synthetic construct
SEQUENCE: 167
EMSWIESVLY Y                                                             11

SEQ ID NO: 168           moltype = AA  length = 5
FEATURE                  Location/Qualifiers
REGION                   1..5
                         note = Fragment of consensus sequence of Table 5-8
source                   1..5
                         mol_type = protein
                         organism = synthetic construct
SEQUENCE: 168
EVLLN                                                                     5

SEQ ID NO: 169           moltype = AA  length = 15
FEATURE                  Location/Qualifiers
REGION                   1..15
                         note = Fragment of consensus sequence of Table 5-8
source                   1..15
                         mol_type = protein
                         organism = synthetic construct
SEQUENCE: 169
KSDYVKEPIP KSGLE                                                         15

SEQ ID NO: 170           moltype = AA  length = 4
FEATURE                  Location/Qualifiers
REGION                   1..4
                         note = Fragment of consensus sequence of Table 5-8
source                   1..4
                         mol_type = protein
                         organism = synthetic construct
SEQUENCE: 170
PYGG                                                                      4

SEQ ID NO: 171           moltype = AA  length = 26
FEATURE                  Location/Qualifiers
REGION                   1..26
                         note = Fragment of consensus sequence of Table 5-8
source                   1..26
                         mol_type = protein
                         organism = synthetic construct
SEQUENCE: 171
EISESAIPFP HRSGVLYKIQ YVVNWE                                             26

SEQ ID NO: 172           moltype = AA  length = 4
FEATURE                  Location/Qualifiers
REGION                   1..4
                         note = Fragment of consensus sequence of Table 5-8
source                   1..4
                         mol_type = protein
                         organism = synthetic construct
SEQUENCE: 172
GDEA                                                                      4

SEQ ID NO: 173           moltype = AA  length = 5
FEATURE                  Location/Qualifiers
REGION                   1..5
                         note = Fragment of consensus sequence of Table 5-8
source                   1..5
                         mol_type = protein
                         organism = synthetic construct
SEQUENCE: 173
RHLNW                                                                     5
```

```
SEQ ID NO: 174          moltype = AA   length = 26
FEATURE                 Location/Qualifiers
REGION                  1..26
                        note = Fragment of consensus sequence of Table 5-8
source                  1..26
                        mol_type = protein
                        organism = synthetic construct
SEQUENCE: 174
YMTPYVSKNP REAYVNYRDL DLGVNS                                            26

SEQ ID NO: 175          moltype = AA   length = 8
FEATURE                 Location/Qualifiers
REGION                  1..8
                        note = Fragment of consensus sequence of Table 5-8
source                  1..8
                        mol_type = protein
                        organism = synthetic construct
SEQUENCE: 175
VWGEKYFK                                                                 8

SEQ ID NO: 176          moltype = AA   length = 13
FEATURE                 Location/Qualifiers
REGION                  1..13
                        note = Fragment of consensus sequence of Table 5-8
source                  1..13
                        mol_type = protein
                        organism = synthetic construct
SEQUENCE: 176
NFKRLVVKTK VDP                                                          13

SEQ ID NO: 177          moltype = AA   length = 10
FEATURE                 Location/Qualifiers
REGION                  1..10
                        note = Fragment of consensus sequence of Table 5-8
source                  1..10
                        mol_type = protein
                        organism = synthetic construct
SEQUENCE: 177
NFFRNEQSIP                                                              10

SEQ ID NO: 178          moltype = AA   length = 9
FEATURE                 Location/Qualifiers
REGION                  1..9
                        note = Fragment of consensus sequence of Table 6-8
source                  1..9
                        mol_type = protein
                        organism = synthetic construct
SEQUENCE: 178
MPVVGMGTA                                                                9

SEQ ID NO: 179          moltype = AA   length = 7
FEATURE                 Location/Qualifiers
REGION                  1..7
                        note = Fragment of consensus sequence of Table 6-8
source                  1..7
                        mol_type = protein
                        organism = synthetic construct
SEQUENCE: 179
AILEAIK                                                                  7

SEQ ID NO: 180          moltype = AA   length = 9
FEATURE                 Location/Qualifiers
REGION                  1..9
                        note = Fragment of consensus sequence of Table 6-8
source                  1..9
                        mol_type = protein
                        organism = synthetic construct
SEQUENCE: 180
GYRHFDTAA                                                                9

SEQ ID NO: 181          moltype = AA   length = 9
FEATURE                 Location/Qualifiers
REGION                  1..9
                        note = Fragment of consensus sequence of Table 6-8
source                  1..9
                        mol_type = protein
                        organism = synthetic construct
```

```
SEQUENCE: 181
LGEALAEAI                                                                        9

SEQ ID NO: 182         moltype = AA  length = 9
FEATURE                Location/Qualifiers
REGION                 1..9
                       note = Fragment of consensus sequence of Table 6-8
source                 1..9
                       mol_type = protein
                       organism = synthetic construct
SEQUENCE: 182
DLFVTSKLW                                                                        9

SEQ ID NO: 183         moltype = AA  length = 6
FEATURE                Location/Qualifiers
REGION                 1..6
                       note = Fragment of consensus sequence of Table 6-8
source                 1..6
                       mol_type = protein
                       organism = synthetic construct
SEQUENCE: 183
LVVPAL                                                                           6

SEQ ID NO: 184         moltype = AA  length = 25
FEATURE                Location/Qualifiers
REGION                 1..25
                       note = Fragment of consensus sequence of Table 6-8
source                 1..25
                       mol_type = protein
                       organism = synthetic construct
SEQUENCE: 184
KSLKNLQLDY IDLYLIHWPI SLKPG                                                     25

SEQ ID NO: 185         moltype = AA  length = 5
FEATURE                Location/Qualifiers
REGION                 1..5
                       note = Fragment of consensus sequence of Table 6-8
source                 1..5
                       mol_type = protein
                       organism = synthetic construct
SEQUENCE: 185
EDLLP                                                                            5

SEQ ID NO: 186         moltype = AA  length = 4
FEATURE                Location/Qualifiers
REGION                 1..4
                       note = Fragment of consensus sequence of Table 6-8
source                 1..4
                       mol_type = protein
                       organism = synthetic construct
SEQUENCE: 186
KGVW                                                                             4

SEQ ID NO: 187         moltype = AA  length = 5
FEATURE                Location/Qualifiers
REGION                 1..5
                       note = Fragment of consensus sequence of Table 6-8
source                 1..5
                       mol_type = protein
                       organism = synthetic construct
SEQUENCE: 187
AMEEC                                                                            5

SEQ ID NO: 188         moltype = AA  length = 14
FEATURE                Location/Qualifiers
REGION                 1..14
                       note = Fragment of consensus sequence of Table 6-8
source                 1..14
                       mol_type = protein
                       organism = synthetic construct
SEQUENCE: 188
KLGLAKAIGV SNFS                                                                 14

SEQ ID NO: 189         moltype = AA  length = 4
FEATURE                Location/Qualifiers
REGION                 1..4
                       note = Fragment of consensus sequence of Table 6-8
```

```
                            -continued source                  1..4
                        mol_type = protein
                        organism = synthetic construct
SEQUENCE: 189
KKLE                                                                    4

SEQ ID NO: 190          moltype = AA   length = 18
FEATURE                 Location/Qualifiers
REGION                  1..18
                        note = Fragment of consensus sequence of Table 6-8
source                  1..18
                        mol_type = protein
                        organism = synthetic construct
SEQUENCE: 190
LLSVATIPPA VNQVEMNP                                                    18

SEQ ID NO: 191          moltype = AA   length = 11
FEATURE                 Location/Qualifiers
REGION                  1..11
                        note = Fragment of consensus sequence of Table 6-8
source                  1..11
                        mol_type = protein
                        organism = synthetic construct
SEQUENCE: 191
WQQKKLREFC K                                                           11

SEQ ID NO: 192          moltype = AA   length = 11
FEATURE                 Location/Qualifiers
REGION                  1..11
                        note = Fragment of consensus sequence of Table 6-8
source                  1..11
                        mol_type = protein
                        organism = synthetic construct
SEQUENCE: 192
VTAYSPLGAK G                                                           11

SEQ ID NO: 193          moltype = AA   length = 15
FEATURE                 Location/Qualifiers
REGION                  1..15
                        note = Fragment of consensus sequence of Table 6-8
source                  1..15
                        mol_type = protein
                        organism = synthetic construct
SEQUENCE: 193
VLKEIAEAKG KTVAQ                                                       15

SEQ ID NO: 194          moltype = AA   length = 14
FEATURE                 Location/Qualifiers
REGION                  1..14
                        note = Fragment of consensus sequence of Table 6-8
source                  1..14
                        mol_type = protein
                        organism = synthetic construct
SEQUENCE: 194
VSLRWVYEQG VTLI                                                        14

SEQ ID NO: 195          moltype = AA   length = 8
FEATURE                 Location/Qualifiers
REGION                  1..8
                        note = Fragment of consensus sequence of Table 6-8
source                  1..8
                        mol_type = protein
                        organism = synthetic construct
SEQUENCE: 195
KERMKQNL                                                                8

SEQ ID NO: 196          moltype = AA   length = 10
FEATURE                 Location/Qualifiers
REGION                  1..10
                        note = Fragment of consensus sequence of Table 6-8
source                  1..10
                        mol_type = protein
                        organism = synthetic construct
SEQUENCE: 196
IFDWELTEED                                                             10
```

```
SEQ ID NO: 197          moltype = AA   length = 4
FEATURE                 Location/Qualifiers
REGION                  1..4
                        note = Fragment of consensus sequence of Table 6-8
source                  1..4
                        mol_type = protein
                        organism = synthetic construct
SEQUENCE: 197
QIPQ                                                                     4

SEQ ID NO: 198          moltype = AA   length = 4
FEATURE                 Location/Qualifiers
REGION                  1..4
                        note = Fragment of consensus sequence of Table 6-8
source                  1..4
                        mol_type = protein
                        organism = synthetic construct
SEQUENCE: 198
RRLI                                                                     4

SEQ ID NO: 199          moltype = AA   length = 5
FEATURE                 Location/Qualifiers
REGION                  1..5
                        note = Fragment of consensus sequence of Table 6-8
source                  1..5
                        mol_type = protein
                        organism = synthetic construct
SEQUENCE: 199
GPYKS                                                                    5

SEQ ID NO: 200          moltype = AA   length = 4
FEATURE                 Location/Qualifiers
REGION                  1..4
                        note = Fragment of consensus sequence of Table 6-8
source                  1..4
                        mol_type = protein
                        organism = synthetic construct
SEQUENCE: 200
DLWD                                                                     4

SEQ ID NO: 201          moltype = AA   length = 5
FEATURE                 Location/Qualifiers
REGION                  1..5
                        note = Fragment of consensus sequence of Table 7-6
source                  1..5
                        mol_type = protein
                        organism = synthetic construct
SEQUENCE: 201
VSPAF                                                                    5

SEQ ID NO: 202          moltype = AA   length = 4
FEATURE                 Location/Qualifiers
REGION                  1..4
                        note = Fragment of consensus sequence of Table 7-6
source                  1..4
                        mol_type = protein
                        organism = synthetic construct
SEQUENCE: 202
AGSS                                                                     4

SEQ ID NO: 203          moltype = AA   length = 5
FEATURE                 Location/Qualifiers
REGION                  1..5
                        note = Fragment of consensus sequence of Table 7-6
source                  1..5
                        mol_type = protein
                        organism = synthetic construct
SEQUENCE: 203
SDSSI                                                                    5

SEQ ID NO: 204          moltype = AA   length = 7
FEATURE                 Location/Qualifiers
REGION                  1..7
                        note = Fragment of consensus sequence of Table 7-6
source                  1..7
                        mol_type = protein
                        organism = synthetic construct
```

```
SEQUENCE: 204
VGKSTNI                                                                         7

SEQ ID NO: 205          moltype = AA  length = 44
FEATURE                 Location/Qualifiers
REGION                  1..44
                        note = Fragment of consensus sequence of Table 7-6
source                  1..44
                        mol_type = protein
                        organism = synthetic construct
SEQUENCE: 205
WHDCAVSKSD RQELLKQKGC VIWITGLSGS GKSTLACALS RALH                                44

SEQ ID NO: 206          moltype = AA  length = 4
FEATURE                 Location/Qualifiers
REGION                  1..4
                        note = Fragment of consensus sequence of Table 7-6
source                  1..4
                        mol_type = protein
                        organism = synthetic construct
SEQUENCE: 206
RGKL                                                                            4

SEQ ID NO: 207          moltype = AA  length = 18
FEATURE                 Location/Qualifiers
REGION                  1..18
                        note = Fragment of consensus sequence of Table 7-6
source                  1..18
                        mol_type = protein
                        organism = synthetic construct
SEQUENCE: 207
YILDGDNVRH GLNSDLSF                                                             18

SEQ ID NO: 208          moltype = AA  length = 6
FEATURE                 Location/Qualifiers
REGION                  1..6
                        note = Fragment of consensus sequence of Table 7-6
source                  1..6
                        mol_type = protein
                        organism = synthetic construct
SEQUENCE: 208
AEDRAE                                                                          6

SEQ ID NO: 209          moltype = AA  length = 16
FEATURE                 Location/Qualifiers
REGION                  1..16
                        note = Fragment of consensus sequence of Table 7-6
source                  1..16
                        mol_type = protein
                        organism = synthetic construct
SEQUENCE: 209
NIRRVGEVAK LFADAG                                                               16

SEQ ID NO: 210          moltype = AA  length = 11
FEATURE                 Location/Qualifiers
REGION                  1..11
                        note = Fragment of consensus sequence of Table 7-6
source                  1..11
                        mol_type = protein
                        organism = synthetic construct
SEQUENCE: 210
VCIASLISPY R                                                                    11

SEQ ID NO: 211          moltype = AA  length = 7
FEATURE                 Location/Qualifiers
REGION                  1..7
                        note = Fragment of consensus sequence of Table 7-6
source                  1..7
                        mol_type = protein
                        organism = synthetic construct
SEQUENCE: 211
ACRALLP                                                                         7

SEQ ID NO: 212          moltype = AA  length = 25
FEATURE                 Location/Qualifiers
REGION                  1..25
                        note = Fragment of consensus sequence of Table 7-6
```

```
                                  -continued source                 1..25
                       mol_type = protein
                       organism = synthetic construct
SEQUENCE: 212
GDFIEVFMDV PLEVCEARDP KGLYK                                           25

SEQ ID NO: 213         moltype = AA   length = 27
FEATURE                Location/Qualifiers
REGION                 1..27
                       note = Fragment of consensus sequence of Table 7-6
source                 1..27
                       mol_type = protein
                       organism = synthetic construct
SEQUENCE: 213
ARAGKIKGFT GIDDPYEAPL DCEIVIQ                                         27

SEQ ID NO: 214         moltype = AA   length = 10
FEATURE                Location/Qualifiers
REGION                 1..10
                       note = Fragment of consensus sequence of Table 7-6
source                 1..10
                       mol_type = protein
                       organism = synthetic construct
SEQUENCE: 214
MADIVVSYLE                                                            10

SEQ ID NO: 215         moltype = AA   length = 23
FEATURE                Location/Qualifiers
REGION                 1..23
                       note = Fragment of consensus sequence of Table 8-7
source                 1..23
                       mol_type = protein
                       organism = synthetic construct
SEQUENCE: 215
MFRAMSTRKV HGGYEKLGDE EAR                                             23

SEQ ID NO: 216         moltype = AA   length = 4
FEATURE                Location/Qualifiers
REGION                 1..4
                       note = Fragment of consensus sequence of Table 8-7
source                 1..4
                       mol_type = protein
                       organism = synthetic construct
SEQUENCE: 216
LKRV                                                                   4

SEQ ID NO: 217         moltype = AA   length = 14
FEATURE                Location/Qualifiers
REGION                 1..14
                       note = Fragment of consensus sequence of Table 8-7
source                 1..14
                       mol_type = protein
                       organism = synthetic construct
SEQUENCE: 217
SVPASVYGHS RNPV                                                       14

SEQ ID NO: 218         moltype = AA   length = 15
FEATURE                Location/Qualifiers
REGION                 1..15
                       note = Fragment of consensus sequence of Table 8-7
source                 1..15
                       mol_type = protein
                       organism = synthetic construct
SEQUENCE: 218
QEVKKTPTAK PTGGS                                                      15

SEQ ID NO: 219         moltype = AA   length = 18
FEATURE                Location/Qualifiers
REGION                 1..18
                       note = Fragment of consensus sequence of Table 8-7
source                 1..18
                       mol_type = protein
                       organism = synthetic construct
SEQUENCE: 219
VHPLSFFDVH FQRKKKKT                                                   18
```

```
SEQ ID NO: 220          moltype = AA   length = 19
FEATURE                 Location/Qualifiers
REGION                  1..19
                        note = Fragment of consensus sequence of Table 8-7
source                  1..19
                        mol_type = protein
                        organism = synthetic construct
SEQUENCE: 220
KKKSLATAKP EFARYMEYV                                                  19

SEQ ID NO: 221          moltype = AA   length = 7
FEATURE                 Location/Qualifiers
REGION                  1..7
                        note = Fragment of consensus sequence of Table 8-7
source                  1..7
                        mol_type = protein
                        organism = synthetic construct
SEQUENCE: 221
EGGVWDP                                                               7

SEQ ID NO: 222          moltype = AA   length = 9
FEATURE                 Location/Qualifiers
REGION                  1..9
                        note = Fragment of consensus sequence of Table 8-7
source                  1..9
                        mol_type = protein
                        organism = synthetic construct
SEQUENCE: 222
SNAPVIHYR                                                             9

SEQ ID NO: 223          moltype = AA   length = 11
FEATURE                 Location/Qualifiers
REGION                  1..11
                        note = Fragment of consensus sequence of Table 10-6
source                  1..11
                        mol_type = protein
                        organism = synthetic construct
SEQUENCE: 223
LLLLLSASSA V                                                          11

SEQ ID NO: 224          moltype = AA   length = 6
FEATURE                 Location/Qualifiers
REGION                  1..6
                        note = Fragment of consensus sequence of Table 10-6
source                  1..6
                        mol_type = protein
                        organism = synthetic construct
SEQUENCE: 224
DPSFQK                                                                6

SEQ ID NO: 225          moltype = AA   length = 27
FEATURE                 Location/Qualifiers
REGION                  1..27
                        note = Fragment of consensus sequence of Table 10-6
source                  1..27
                        mol_type = protein
                        organism = synthetic construct
SEQUENCE: 225
SGPEAFAFDS TGKGFYTGVS DGRILKY                                         27

SEQ ID NO: 226          moltype = AA   length = 4
FEATURE                 Location/Qualifiers
REGION                  1..4
                        note = Fragment of consensus sequence of Table 10-6
source                  1..4
                        mol_type = protein
                        organism = synthetic construct
SEQUENCE: 226
VDFA                                                                  4

SEQ ID NO: 227          moltype = AA   length = 5
FEATURE                 Location/Qualifiers
REGION                  1..5
                        note = Fragment of consensus sequence of Table 10-6
source                  1..5
                        mol_type = protein
                        organism = synthetic construct
```

```
SEQUENCE: 227
LCGRP                                                                        5

SEQ ID NO: 228          moltype = AA  length = 19
FEATURE                 Location/Qualifiers
REGION                  1..19
                        note = Fragment of consensus sequence of Table 10-6
source                  1..19
                        mol_type = protein
                        organism = synthetic construct
SEQUENCE: 228
GIAFNKTGDL YVADAYLGL                                                        19

SEQ ID NO: 229          moltype = AA  length = 35
FEATURE                 Location/Qualifiers
REGION                  1..35
                        note = Fragment of consensus sequence of Table 10-6
source                  1..35
                        mol_type = protein
                        organism = synthetic construct
SEQUENCE: 229
GGLATQLATS VDGVPFKWLD GLDVDQRTGV VYFTD                                       35

SEQ ID NO: 230          moltype = AA  length = 4
FEATURE                 Location/Qualifiers
REGION                  1..4
                        note = Fragment of consensus sequence of Table 10-6
source                  1..4
                        mol_type = protein
                        organism = synthetic construct
SEQUENCE: 230
VLIV                                                                         4

SEQ ID NO: 231          moltype = AA  length = 12
FEATURE                 Location/Qualifiers
REGION                  1..12
                        note = Fragment of consensus sequence of Table 10-6
source                  1..12
                        mol_type = protein
                        organism = synthetic construct
SEQUENCE: 231
TGRLLKYDPS TK                                                               12

SEQ ID NO: 232          moltype = AA  length = 8
FEATURE                 Location/Qualifiers
REGION                  1..8
                        note = Fragment of consensus sequence of Table 10-6
source                  1..8
                        mol_type = protein
                        organism = synthetic construct
SEQUENCE: 232
VTVLMKGL                                                                     8

SEQ ID NO: 233          moltype = AA  length = 10
FEATURE                 Location/Qualifiers
REGION                  1..10
                        note = Fragment of consensus sequence of Table 10-6
source                  1..10
                        mol_type = protein
                        organism = synthetic construct
SEQUENCE: 233
DGSFVLVAEF                                                                  10

SEQ ID NO: 234          moltype = AA  length = 5
FEATURE                 Location/Qualifiers
REGION                  1..5
                        note = Fragment of consensus sequence of Table 10-6
source                  1..5
                        mol_type = protein
                        organism = synthetic construct
SEQUENCE: 234
IKKYW                                                                        5

SEQ ID NO: 235          moltype = AA  length = 8
FEATURE                 Location/Qualifiers
REGION                  1..8
                        note = Fragment of consensus sequence of Table 10-6
```

```
source                  1..8
                        mol_type = protein
                        organism = synthetic construct
SEQUENCE: 235
KGPKAGSS                                                               8

SEQ ID NO: 236          moltype = AA   length = 7
FEATURE                 Location/Qualifiers
REGION                  1..7
                        note = Fragment of consensus sequence of Table 10-6
source                  1..7
                        mol_type = protein
                        organism = synthetic construct
SEQUENCE: 236
NPDNIKR                                                                7

SEQ ID NO: 237          moltype = AA   length = 8
FEATURE                 Location/Qualifiers
REGION                  1..8
                        note = Fragment of consensus sequence of Table 10-6
source                  1..8
                        mol_type = protein
                        organism = synthetic construct
SEQUENCE: 237
GNFWVASS                                                               8

SEQ ID NO: 238          moltype = AA   length = 4
FEATURE                 Location/Qualifiers
REGION                  1..4
                        note = Fragment of consensus sequence of Table 10-6
source                  1..4
                        mol_type = protein
                        organism = synthetic construct
SEQUENCE: 238
LSEV                                                                   4

SEQ ID NO: 239          moltype = AA   length = 6
FEATURE                 Location/Qualifiers
REGION                  1..6
                        note = Fragment of consensus sequence of Table 10-6
source                  1..6
                        mol_type = protein
                        organism = synthetic construct
SEQUENCE: 239
LYIGTL                                                                 6

SEQ ID NO: 240          moltype = AA   length = 6
FEATURE                 Location/Qualifiers
REGION                  1..6
                        note = Fragment of consensus sequence of Table 10-6
source                  1..6
                        mol_type = protein
                        organism = synthetic construct
SEQUENCE: 240
PFAGIL                                                                 6

SEQ ID NO: 241          moltype = AA   length = 10
FEATURE                 Location/Qualifiers
REGION                  1..10
                        note = Fragment of consensus sequence of Table 11-6
source                  1..10
                        mol_type = protein
                        organism = synthetic construct
SEQUENCE: 241
ALVSLLLLLS                                                            10

SEQ ID NO: 242          moltype = AA   length = 6
FEATURE                 Location/Qualifiers
REGION                  1..6
                        note = Fragment of consensus sequence of Table 11-6
source                  1..6
                        mol_type = protein
                        organism = synthetic construct
SEQUENCE: 242
PSFQKL                                                                 6
```

```
SEQ ID NO: 243          moltype = AA  length = 27
FEATURE                 Location/Qualifiers
REGION                  1..27
                        note = Fragment of consensus sequence of Table 11-6
source                  1..27
                        mol_type = protein
                        organism = synthetic construct
SEQUENCE: 243
SGPESFAFDS TGKGFYTGVS DGRILKY                                         27

SEQ ID NO: 244          moltype = AA  length = 4
FEATURE                 Location/Qualifiers
REGION                  1..4
                        note = Fragment of consensus sequence of Table 11-6
source                  1..4
                        mol_type = protein
                        organism = synthetic construct
SEQUENCE: 244
VDFA                                                                   4

SEQ ID NO: 245          moltype = AA  length = 5
FEATURE                 Location/Qualifiers
REGION                  1..5
                        note = Fragment of consensus sequence of Table 11-6
source                  1..5
                        mol_type = protein
                        organism = synthetic construct
SEQUENCE: 245
LCGRP                                                                  5

SEQ ID NO: 246          moltype = AA  length = 5
FEATURE                 Location/Qualifiers
REGION                  1..5
                        note = Fragment of consensus sequence of Table 11-6
source                  1..5
                        mol_type = protein
                        organism = synthetic construct
SEQUENCE: 246
GISFN                                                                  5

SEQ ID NO: 247          moltype = AA  length = 14
FEATURE                 Location/Qualifiers
REGION                  1..14
                        note = Fragment of consensus sequence of Table 11-6
source                  1..14
                        mol_type = protein
                        organism = synthetic construct
SEQUENCE: 247
KTGDLYVADA YLGL                                                       14

SEQ ID NO: 248          moltype = AA  length = 11
FEATURE                 Location/Qualifiers
REGION                  1..11
                        note = Fragment of consensus sequence of Table 11-6
source                  1..11
                        mol_type = protein
                        organism = synthetic construct
SEQUENCE: 248
GGLATQLATS V                                                          11

SEQ ID NO: 249          moltype = AA  length = 23
FEATURE                 Location/Qualifiers
REGION                  1..23
                        note = Fragment of consensus sequence of Table 11-6
source                  1..23
                        mol_type = protein
                        organism = synthetic construct
SEQUENCE: 249
GVPFKWLDGL DVDQRTGVVY FTD                                             23

SEQ ID NO: 250          moltype = AA  length = 4
FEATURE                 Location/Qualifiers
REGION                  1..4
                        note = Fragment of consensus sequence of Table 11-6
source                  1..4
                        mol_type = protein
                        organism = synthetic construct
```

```
SEQUENCE: 250
TGRL                                                                         4

SEQ ID NO: 251          moltype = AA  length = 7
FEATURE                 Location/Qualifiers
REGION                  1..7
                        note = Fragment of consensus sequence of Table 11-6
source                  1..7
                        mol_type = protein
                        organism = synthetic construct
SEQUENCE: 251
KYDPSTK                                                                      7

SEQ ID NO: 252          moltype = AA  length = 8
FEATURE                 Location/Qualifiers
REGION                  1..8
                        note = Fragment of consensus sequence of Table 11-6
source                  1..8
                        mol_type = protein
                        organism = synthetic construct
SEQUENCE: 252
VTVLMKGL                                                                     8

SEQ ID NO: 253          moltype = AA  length = 10
FEATURE                 Location/Qualifiers
REGION                  1..10
                        note = Fragment of consensus sequence of Table 11-6
source                  1..10
                        mol_type = protein
                        organism = synthetic construct
SEQUENCE: 253
DGSFVLVAEF                                                                  10

SEQ ID NO: 254          moltype = AA  length = 5
FEATURE                 Location/Qualifiers
REGION                  1..5
                        note = Fragment of consensus sequence of Table 11-6
source                  1..5
                        mol_type = protein
                        organism = synthetic construct
SEQUENCE: 254
IKKYW                                                                        5

SEQ ID NO: 255          moltype = AA  length = 8
FEATURE                 Location/Qualifiers
REGION                  1..8
                        note = Fragment of consensus sequence of Table 11-6
source                  1..8
                        mol_type = protein
                        organism = synthetic construct
SEQUENCE: 255
KGPKAGTS                                                                     8

SEQ ID NO: 256          moltype = AA  length = 9
FEATURE                 Location/Qualifiers
REGION                  1..9
                        note = Fragment of consensus sequence of Table 11-6
source                  1..9
                        mol_type = protein
                        organism = synthetic construct
SEQUENCE: 256
NPDNIKRNG                                                                    9

SEQ ID NO: 257          moltype = AA  length = 8
FEATURE                 Location/Qualifiers
REGION                  1..8
                        note = Fragment of consensus sequence of Table 11-6
source                  1..8
                        mol_type = protein
                        organism = synthetic construct
SEQUENCE: 257
GNFWVASS                                                                     8

SEQ ID NO: 258          moltype = AA  length = 8
FEATURE                 Location/Qualifiers
REGION                  1..8
                        note = Fragment of consensus sequence of Table 11-6
```

```
source                  1..8
                        mol_type = protein
                        organism = synthetic construct
SEQUENCE: 258
DPRAVKVD                                                                    8

SEQ ID NO: 259          moltype = AA  length = 7
FEATURE                 Location/Qualifiers
REGION                  1..7
                        note = Fragment of consensus sequence of Table 11-6
source                  1..7
                        mol_type = protein
                        organism = synthetic construct
SEQUENCE: 259
VLQVIPL                                                                     7

SEQ ID NO: 260          moltype = AA  length = 4
FEATURE                 Location/Qualifiers
REGION                  1..4
                        note = Fragment of consensus sequence of Table 11-6
source                  1..4
                        mol_type = protein
                        organism = synthetic construct
SEQUENCE: 260
ISEV                                                                        4

SEQ ID NO: 261          moltype = AA  length = 6
FEATURE                 Location/Qualifiers
REGION                  1..6
                        note = Fragment of consensus sequence of Table 11-6
source                  1..6
                        mol_type = protein
                        organism = synthetic construct
SEQUENCE: 261
LYIGSL                                                                      6

SEQ ID NO: 262          moltype = AA  length = 6
FEATURE                 Location/Qualifiers
REGION                  1..6
                        note = Fragment of consensus sequence of Table 11-6
source                  1..6
                        mol_type = protein
                        organism = synthetic construct
SEQUENCE: 262
PFAGIL                                                                      6
```

What is claimed is:

1. A transgenic plant transformed with an exogenous a nucleic acid molecule, wherein the exogenous nucleic acid molecule comprises:
   a) a first nucleic acid having a regulatory sequence capable of causing transcription in a plant; and
   b) a second nucleic acid comprising a polynucleotide sequence encoding a polypeptide, wherein the polypeptide comprises an amino acid sequence that exhibits at least 95% amino acid sequence identity to the amino acid sequence of SEQ ID NO: 44;
   wherein said first and second nucleic acids are operably linked,
   wherein said second nucleic acid is heterologous to said first nucleic acid, and
   wherein said second nucleic acid comprising said polynucleotide sequence encoding said polypeptide is overexpressed in the transgenic plant; and
   wherein the transgenic plant exhibits increased drought tolerance, increased thermo-tolerance, increased osmotic stress tolerance, and/or increased water use efficiency as compared to a control plant of the same plant species lacking said exogenous nucleic acid molecule and grown under identical growth conditions.

2. The transgenic plant of claim 1, wherein the second nucleic acid comprising said polynucleotide sequence encodes a polypeptide comprising an amino acid sequence that exhibits at least 98% amino acid sequence identity to the amino acid sequence of SEQ ID NO: 44.

3. The transgenic plant of claim 1, wherein the second nucleic acid comprising said polynucleotide sequence exhibits at least 96% nucleic acid sequence identity to the polynucleotide sequence of SEQ ID NO: 43,
   wherein the second nucleic acid comprising said polynucleotide sequence exhibits at least 97% nucleic acid sequence identity to the polynucleotide sequence of SEQ ID NO: 43, or
   wherein the second nucleic acid comprising said polynucleotide sequence comprises the polynucleotide sequence of SEQ ID NO: 43.

4. The transgenic plant of claim 1, wherein the second nucleic acid comprising said polynucleotide sequence encodes a polypeptide comprising an amino acid sequence that exhibits at least 97% amino acid sequence identity to the amino acid sequence of SEQ ID NO: 44, or
   wherein the second nucleic acid comprising said polynucleotide sequence encodes a polypeptide comprising the amino acid sequence of SEQ ID NO: 44.

5. A transgenic plant cell or a transgenic plant material of the transgenic plant of claim 1, and wherein said transgenic plant cell or transgenic plant material comprise said exogenous nucleic acid molecule.

6. A transgenic seed obtained from the transgenic plant of claim 1, and wherein said transgenic seed comprises said exogenous nucleic acid molecule.

7. The transgenic plant of claim 1, wherein the second nucleic acid comprising said polynucleotide sequence encodes a polypeptide comprising the amino acid sequence of SEQ ID NO: 44.

8. A transgenic progeny plant of the transgenic plant of claim 1, wherein the transgenic progeny comprises said exogenous nucleic acid molecule.

\* \* \* \* \*